US008557842B2

(12) United States Patent
Davis et al.

(10) Patent No.: US 8,557,842 B2
(45) Date of Patent: Oct. 15, 2013

(54) COCAINE ANALOGS AND METHODS OF PREPARATION AND USES THEREOF

(75) Inventors: Franklin A. Davis, Wynnewood, PA (US); Naresh Theddu, Andhra Pardesh (IN); Maarten E. A. Reith, New York, NY (US)

(73) Assignee: Temple University—Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 13/475,292

(22) Filed: May 18, 2012

(65) Prior Publication Data
US 2012/0329828 A1    Dec. 27, 2012

Related U.S. Application Data

(63) Continuation-in-part of application No. PCT/US2011/043531, filed on Jul. 11, 2011.

(60) Provisional application No. 61/365,930, filed on Jul. 20, 2010, provisional application No. 61/363,364, filed on Jul. 12, 2010.

(51) Int. Cl.
*C07D 451/12*    (2006.01)
*A61K 31/46*    (2006.01)
*A61P 23/00*    (2006.01)
*A61P 25/24*    (2006.01)

(52) U.S. Cl.
USPC .......................................... 514/304; 546/130

(58) Field of Classification Search
None
See application file for complete search history.

(56) References Cited

U.S. PATENT DOCUMENTS

| 5,268,480 | A | 12/1993 | Kozikowski | 546/23 |
| 5,391,744 | A | 2/1995 | Kozikowski | 546/23 |
| 5,834,484 | A | 11/1998 | Trudell et al. | 514/304 |
| 6,180,648 | B1 | 1/2001 | Kozikowski et al. | 514/317 |
| 6,472,422 | B2 | 10/2002 | Kozikowski et al. | 514/451 |
| 6,596,868 | B2 | 7/2003 | Okano et al. | 546/124 |
| 2005/0014848 | A1 | 1/2005 | Marek et al. | 514/657 |
| 2005/0238733 | A1 | 10/2005 | Henry | 424/717 |
| 2009/0105248 | A1 | 4/2009 | Ho et al. | 514/235.2 |

FOREIGN PATENT DOCUMENTS

| GB | 1012622 | 12/1965 | | |
| WO | WO 2008/042926 | 4/2008 | ......... | C07D 211/22 |
| WO | WO 2009/111607 | 9/2009 | ......... | C07D 211/26 |

OTHER PUBLICATIONS

Beddoes et al., Synthesis of the tricyclic nucleus of the alkaloid stemofoline: X-ray Crystal Structure of (4RS,5RS,7SR,10RS)-10-butyl-5-hydroxy-1-azatricyclo[5.3.0.04,10]decan-2-one, 63(47) Tetrahedron 11666-11671 (2007) (CAS Abstract).*
Mahaney et al., Structure-Activity Relationships of the 1-amino-3-(1H-indol-1-yl)-3-phenylpropan-2-ol Series of Monoamine Reuptake Inhibitors, 19 Bioorg. Med. Chem. Lett. 5807-5810 (2009).*
Airaksinen, et al., "Nuclear Magnetic Resonance and Molecular Orbital Study of Some Cocaine Analogues", *Tetrahedron* 55 (1999) 10537-10546.
Carroll, et al., "Synthesis and Ligand Binding of Cocaine Isomers at the Cocaine Receptor", *J. Med. Chem.* 1991, 34, 883-886.
Davis, et al., "Asymmetric Synthesis of Substituted Tropinones Using the Intramolecular Mannich Cyclization Reaction and Acyclic N-Sulfinyl β-Amino Ketone Ketals", *Organic Letters* 2009, vol. 11, No. 7, 1647-1650.
Davis, et al., "Asymmetric Total Synthesis of (S)-(+)-Cocaine and the First Synthesis of Cocaine C-1 Analogs from N-Sulfinyl β-Amino Ester Ketals", *Organic Letters* 2010, vol. 12, No. 18, 4118-4121.
Davis, et al., "Enantioselective Synthesis of Cocaine C-1 Analogues using Sulfinimines (N-Sulfinyl Imines)", *J. Org. Chem* 2012, 77, 2345-2359.
Emond, et al., Synthesis of Tropane and Nortropane Analogues with Phenyl Substitutions as Serotonin Transporter Ligands, *Bioorganic & Medical Chemistry* 9 (2001), 1849-1855.
Lin et al., "Enantiospecific Synthesis of Natural (−)-Cocaine and Unnatural (+)-Cocaine from D- L-Glutamic Acid", *J. Org. Chem.* 1998, 63, 4069-4078.
Singh, "Chemistry, Design and Structure-Activity Relationship of Cocaine Antagonists", *Chem Rev.* 2000, 100, 925-1024.
Tufariello, et al., "Synthesis in the Tropane Class of Alkaloids, Pseudotropine and dlCocaine", *Journal of the American Chemical Society*, 101:9, Apr. 25, 1979.
Wilson, et al., "Synthesis of Two Radiofluorinated Cocaine Analogues using Distilled 2[$^{18}$F]Fluoroethyl Bromide", *Appl. Radiat. Isot.*, vol. 46, No. 8, pp. 765-770, 1995.
Search Report and Written Opinion dated Dec. 6, 2011.
Beddoes, et al., Synthesis of the Tricyclic Nucleus of the Alkaloid Stemofoline: X-Ray Crystal Structure of (4RS,5RS,7SR,10RS)-10-Butyl-5-hydroxy-1-azatricyclo[5.3.0.0$^{4,10}$]decan-2-one, *J. Chem. Soc. Chem. Commun.*, (7), 538-540, 1992.

* cited by examiner

*Primary Examiner* — Janet Andres
*Assistant Examiner* — Timothy R Rozof
(74) *Attorney, Agent, or Firm* — Drinker Biddle & Reath LLP

(57) ABSTRACT

The invention provides novel cocaine analogs. The invention also provides a method of preparing cocaine analogs with control over the substituents installed at the C-1, C-2, C-3, C-4 and N-8 positions of the tropane bicyclic scaffold. The invention further provides methods of providing anesthesia, blocking reuptake of a monoamine neurotransmitter, and treating depression, by administering to a subject in need of such treatment a pharmaceutical composition comprising a compound of the invention.

48 Claims, 1 Drawing Sheet

COCAINE ANALOGS AND METHODS OF PREPARATION AND USES THEREOF

CROSS-REFERENCE TO RELATED APPLICATIONS

This is a continuation-in-part of International Application PCT/US2011/043531, filed Jul. 11, 2011 which claims the benefit of the filing dates of U.S. Provisional Patent Applications Nos. 61/363,364, filed Jul. 12, 2010, and 61/365,930, filed Jul. 20, 2010. The entire disclosures of the aforesaid applications are incorporated herein by reference.

REFERENCE TO GOVERNMENT GRANT

The invention described herein was supported in part by the Government grant No. GM 57870 awarded by the National Institute of General Medical Sciences (NIH). The Federal Government may have certain rights in the invention.

FIELD OF INVENTION

The invention relates to novel cocaine analogs, synthetic methods for their preparation, and use of these compounds in providing anesthesia and/or inhibiting reuptake of a monoamine neurotransmitter.

BACKGROUND OF THE INVENTION (1R,2R,3S,5S)-(−)-cocaine (1), also known as benzoylmethylecgonine or methyl-(1R,2R,3S,5S)-3-(benzoyloxy)-8-methyl-8-azabicyclo[3.2.1]octane-2-carboxylate (hereafter referred to as "cocaine"), is a crystalline tropane alkaloid obtained from the leaves of the coca plant. (1R,2R,3S,5S)-(−)-cocaine is the only stereoisomer of this molecule that is addictive (Carrol et al., 1991, J. Med. Chem. 31:883-886).

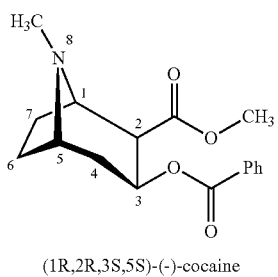

(1R,2R,3S,5S)-(−)-cocaine (1)

Cocaine is a stimulant of the central nervous system and an appetite suppressant. Specifically, it is a serotonin-norepinephrine-dopamine reuptake inhibitor (SNDRI)—also referred to as a triple reuptake inhibitor (TRI)—acting as an exogenous catecholamine transporter ligand. As a SNDRI/TRI, cocaine acts simultaneously as a reuptake inhibitor for the monoamine neurotransmitters—serotonin, norepinephrine (noradrenaline) and dopamine—by blocking the action of the serotonin transporter (SERT), norepinephrine transporter (NET) and dopamine transporter (DAT), respectively. This, in turn, leads to increased extracellular concentrations of these neurotransmitters and an increase in serotonergic, noradrenergic or adrenergic, and dopaminergic neurotransmission.

The pharmacodynamics of cocaine involves various neurotransmitter systems. The most extensively studied effect of cocaine on the central nervous system is the blockade of the dopamine transporter protein. Dopamine transmitter released during neural signaling is normally recycled via the transporter—the transporter binds dopamine and pumps it out of extracellular space back into the presynaptic neuron, where it is taken up into storage vesicles. There is a great deal of evidence that dopamine transmission is volume transmission. DATs are mostly extrasynaptic, and dopamine is cleared from the synapse by diffusion (Rice & Cragg, 2008, Brain. Res. Rev. 58:303-13). Cocaine binds tightly at the dopamine transporter, forming a complex that blocks the transporter's function. The dopamine transporter can no longer perform its reuptake function, and thus dopamine accumulates outside dopamine cells. This results in an enhanced and prolonged post-synaptic effect of dopaminergic signaling at dopamine receptors on the receiving neuron. Prolonged exposure to cocaine, as derived from habitual use, leads to homeostatic dysregulation of normal (i.e. without cocaine) dopaminergic signaling via down-regulation of dopamine receptors and enhanced signal transduction. The decreased dopaminergic signaling after chronic cocaine use may contribute to depressive mood disorders and sensitize this important brain reward circuit to the reinforcing effects of cocaine (e.g. enhanced dopaminergic signaling only when cocaine is self-administered). This sensitization contributes to the intractable nature of addiction and relapse.

Cocaine has also been shown to directly stabilize the dopamine transporter on the open outward-facing conformation, whereas other stimulants (such as phenethylamines) stabilize the closed conformation. Further, cocaine binds in such a way to the dopamine transporter as to inhibit a hydrogen bond innate to transporter, whereas binding of amphetamine and similar molecules to the dopamine receptor does not inhibit formation of such bond (Kniazeff et al., 2008, Nature Neuroscience 11(7):780).

Cocaine binding affects multiple serotonin (5-hydroxytryptamine, or 5-HT) receptors, and inhibition of the reuptake of 5-HT is thought to be an important contributor to the effects of cocaine (Carta et al., 2003, Eur. J. Pharmacol. 459(2-3):167-69). The 5-HT$_2$ receptor (particularly the subtypes 5-HT$_2$AR, 5-HT$_2$BR and 5-HT$_2$CR) show influence in the evocation of hyperactivity displayed in cocaine use (Filip et al., 2004, J. Pharmacol. Exp. Ther. 310(3):1246-54).

Cocaine functions as a sigma ligand agonist, and examples of sigma receptors affected are NMDA and the D$_1$ dopamine receptor (Liuch et al., 2005, Pharmacol. Biochem. Behav. 82(3):478-87). Cocaine also blocks sodium channels, thereby interfering with the propagation of action potentials. Because of this effect, cocaine, similarly to lignocaine and novocaine, acts as a local anesthetic. Cocaine has some target binding to the site of the kappa-opioid receptor as well, and enhances dopaminergic transmission from the substantia nigra.

Cocaine is thus a highly potent bioactive molecule, acting in various receptor and reward systems. Because of the way it affects the mesolimbic reward pathway, cocaine is highly addictive. Cocaine abuse and addiction is now a worldwide problem, and approximately 4.5 million people in the United States are thought to be chronic abusers of this drug. The cocaine market in the United States has been estimated to exceed $35 billion and has an enormous impact socio-economically. Unfortunately, there are no medications currently available for the treatment of cocaine addiction.

A compound that acts as an antagonist or agonist of cocaine in its binding to various receptors could in principle be used in the treatment of cocaine addiction, as long as it is not addictive or cause the same degree of euphoria in individuals. In another aspect, such compound could be used as an anesthetic agent, mimicking the anesthesia provided by cocaine without its well-known addictive properties.

A starting point for the identification of a cocaine analog could be the preparation and characterization of compounds that share the general structure of the natural product. The synthetic efforts targeting cocaine analogs has been concentrated on partially degrading cocaine itself and derivatizing the resulting scaffold to obtain novel tropane analogs. For example, the ester groups at the C-2 and C-3 centers of cocaine may be hydrolyzed, or the N-8 center of cocaine may be demethylated, and the corresponding compound may then be derivatized using standard chemical procedures.

However, systematic exploration of structure-activity relationships (SAR) around the cocaine molecule is currently hampered by the lack of a synthetic methodology that allows one to introduce substituents in the cocaine-tropane skeleton in a regiospecific and stereospecific manner. In one aspect, it is challenging to stereospecifically prepare a cocaine analog with C-2 and C-3 substituents in the cis orientation, an arrangement that is thought to be necessary for bioactivity. For example, Tufariello and coworkers disclosed a non-stereoselective synthesis of racemic cocaine (J. Am. Chem. Soc. 1978, 101:2435-2442). This synthesis comprised a nitrone intermediate, which the authors could not prepare as a pure enantiomer, and therefore this methodology did not allow the development of an asymmetric synthesis of cocaine.

In another aspect, the synthetic approaches disclosed so far do not allow the introduction of substituents at the C-1 and C-4 positions of the cocaine-tropane skeleton (Singh, 2000, Chem. Rev. 100, 925-1024). These synthetic limitations must be overcome to open the way to the synthesis and biological characterization of cocaine analogs with diverse substitutions at those positions.

There is thus a need for the identification and characterization of novel cocaine analogs. These analogs may be useful in understanding the biological activities of cocaine. These analogs may have novel receptor selectivities and find use as pharmaceutical tools in the treatment of drug addiction. These analogs may find further use as inhibitors of reuptake of one or more monoamine neurotransmitters. These analogs may also find use as non-addictive anesthetic agents. Currently there is no synthetic method that allows the chiral synthesis of cocaine analogs wherein substitution may be systematically and stereoselectively introduced at the C-1, C-2, C-3, C-4 and N-8 positions. Such synthetic method would allow the exploration of the chemical diversity around the cocaine scaffold and the preparation of novel cocaine analogs that are not synthetically accessible currently. The present invention addresses and meets these needs.

SUMMARY OF THE INVENTION

The present invention relates to the unexpected discovery of a synthetic method that allows the chiral synthesis of a cocaine analog wherein substituents at the C-1, C-2, C-3, C-4 and N-8 positions of the tropane bicyclic scaffold are introduced stereospecifically.

The compounds of the invention were not accessible by the synthetic methods previously disclosed in the literature. The cocaine analogs of the invention may be used to study cocaine pharmacology, treat cocaine addiction, inhibit reuptake of one or more monoamine neurotransmitters, and/or provide anesthesia to a subject in need thereof.

The invention includes a compound of Formula (I):

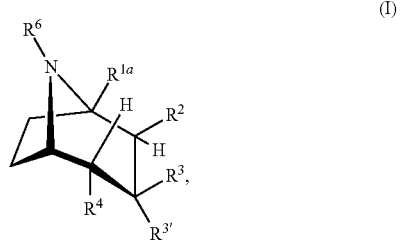

wherein:
$R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^3$ is acyloxy, substituted acyloxy, aroyloxy, substituted aroyloxy, heteroaroyloxy, substituted heteroaroyloxy, —OC(=O)—NR$^7$R$^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

$R^{3'}$ is H;

$R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

In one embodiment, $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, or substituted $(C_{2-6})$ alkynyl. In another embodiment, $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, or substituted $(C_{2-6})$ alkenyl. In yet another embodiment, $R^{1a}$ is $(C_{1-6})$ alkyl, substituted $(C_{1-6})$ alkyl, $(C_{3-6})$ cycloalkyl, or substituted $(C_{3-6})$ cycloalkyl. In yet another embodiment, $R^{1a}$ is $(C_{1-6})$ alkyl or substituted $(C_{1-6})$ alkyl. In yet another embodiment, $R^{1a}$ is methyl. In another embodiment, $R^{1a}$ is methyl which is mono-, di- or tri-substituted with halogen. In another embodiment, $R^{1a}$ is mono-, di- or tri-substituted with fluorine.

In one embodiment, R² is cyano, —C(=O)H, alkoxycarbonyl, aroxycarbonyl, heterocyclyloxycarbonyl, acyl, aroyl, heterocycloyl, —C(=NR⁹)R⁷, —C(=O)NR⁷R⁸, —C(=S)NR⁷R⁸, —C(=O)N(OMe)Me, or —C(=S)N(OMe)Me. In another embodiment, R² is cyano, —C(=O)H, alkoxycarbonyl, aroxycarbonyl, heterocyclyloxycarbonyl, —C(=NR⁹)R⁷, —C(=O)NR⁷R⁸, —C(=S)NR⁷R⁸, —C(=O)N(OMe)Me, or —C(=S)N(OMe)Me. In yet another embodiment, R² is alkoxycarbonyl, aroxycarbonyl, heterocyclyloxycarbonyl, —C(=O)NR⁷R⁸, —C(=S)NR⁷R⁸, —C(=O)N(OMe)Me, or —C(=S)N(OMe)Me.

In one embodiment, R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, aroxy, substituted aroxy, heterocycloxy, substituted heterocycloxy, (alkoxycarbonyl)oxy, (aroxycarbonyl)oxy, or (heterocyclyloxycarbonyl)oxy. In another embodiment, R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, (alkoxycarbonyl)oxy, (aroxycarbonyl)oxy, or (heterocyclyloxycarbonyl)oxy. In yet another embodiment, R³ is acyloxy, substituted acyloxy, aroyloxy, substituted aroyloxy, heteroaroyloxy, substituted heteroaroyloxy, —OC(=O)—NR⁷R⁸, (alkoxycarbonyl)oxy, (aroxycarbonyl)oxy, or (heterocyclyloxycarbonyl)oxy. In yet another embodiment, R³ is acyloxy, substituted acyloxy, aroyloxy, substituted aroyloxy, heteroaroyloxy, substituted heteroaroyloxy, or —OC(=O)—NR⁷R⁸. In yet another embodiment, R³ is acyloxy, substituted acyloxy, aroyloxy, or substituted aroyloxy.

In one embodiment, R⁴ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, substituted heterocyclyl, (C₁₋₆) alkoxy, aroxy, or heteroaroxy. In another embodiment, R⁴ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl. In yet another embodiment, R⁴ is H, (C₁₋₆) alkyl, substituted (C₁₋₆) alkyl, (C₃₋₆) cycloalkyl, or substituted (C₃₋₆) cycloalkyl.

In one embodiment, R⁶ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, substituted heterocyclyl, —C(=O)NR⁷R⁸, —SO₂R⁹, —SO₂NR⁷R⁸, —P(=O)(OR⁹)₂, alkoxycarbonyl, aroxycarbonyl, heterocyclyloxycarbonyl, acyl, aroyl, or heterocycloyl. In another embodiment, R⁶ is H, (C₁₋₆) alkyl, substituted (C₁₋₆) alkyl, (C₃₋₆) cycloalkyl, substituted (C₃₋₆) cycloalkyl, C(=O)NR⁷R⁸, —SO₂R⁹, —SO₂NR⁷R⁸, —P(=O)(OR⁹)₂, alkoxycarbonyl, aroxycarbonyl, heterocyclyloxycarbonyl, acyl, aroyl, or heterocycloyl. In yet another embodiment, R⁶ is H, (C₁₋₆) alkyl, substituted (C₁₋₆) alkyl, (C₃₋₆) cycloalkyl, substituted (C₃₋₆) cycloalkyl, —C(=O)NR⁷R⁸, —SO₂R⁹, —SO₂NR⁷R⁸, alkoxycarbonyl, aroxycarbonyl, heterocyclyloxycarbonyl, acyl, aroyl, or heterocycloyl.

In one embodiment, the compound of Formula (I) is methyl (1R,2R,3S,5S)-(−)-3-(benzoyloxy)-1,8-dimethyl-8-azabicyclo [3.2.1]octane-2-carboxylate, or a salt thereof. In another embodiment, the compound is methyl (1R,2R,3S,5S)-(−)-1-propyl-3-(benzoyloxy)-8-methyl-8-azabicyclo[3.2.1]octane-2-carboxylate, or a salt thereof. In another embodiment, the compound is methyl (1R, 2R, 3S, 5S)-(−)-1-ethyl-3-(benzoyloxy)-8-methyl-8-azabicyclo[3.2.1]octane-2-carboxylate, or a salt thereof. In another embodiment, the compound is methyl (1R,2R,3S,5S)-(−)-1-pentyl-3-(benzoyloxy)-8-methyl-8-azabicyclo[3.2.1]octane-2-carboxylate, or a salt thereof. In another embodiment, the compound is methyl (1R,2R,3S,5)-(−)-3-(benzoyloxy)-1-phenyl-8-methyl-8-azabicyclo[3.2.1]octane-2-carboxylate, or a salt thereof.

The invention also includes a process for preparing a compound of formula (XIII):

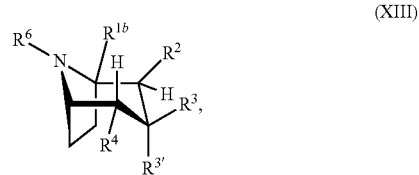

wherein:

R¹ᵇ is H, (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, or substituted heterocyclyl;

R² is cyano, —C(=O)H, alkoxycarbonyl, aroxycarbonyl, heterocyclyloxycarbonyl, acyl, aroyl, heterocycloyl, —C(=NR⁹)R⁷, —C(=O)NR⁷R⁸, —C(=S)NR⁷R⁸, —C(=O)N(OMe)Me, —C(=S)N(OMe)Me, —SO₂R⁹, —SO₂NR⁷R⁸, or —P(=O)(OR⁹)₂;

R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, aroxy, substituted aroxy, heterocycloxy, substituted heterocycloxy, (alkoxycarbonyl)oxy, (aroxycarbonyl)oxy, or (heterocyclyloxycarbonyl)oxy;

R³' is H;

R⁴ is H, (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, substituted heterocyclyl, (C₁₋₆) alkoxy, aroxy, or heteroaroxy;

R⁶ is H, (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, substituted heterocyclyl, —C(=O)NR⁷R⁸, —SO₂R⁹, —SO₂NR⁷R⁸, —P(=O)(OR⁹)₂, alkoxycarbonyl, aroxycarbonyl, heterocyclyloxycarbonyl, acyl, aroyl, or heterocycloyl;

R⁷ and R⁸ are independently H, (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl; and, each occurrence of R⁹ is independently (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl;

with the proviso that if R² is methoxycarbonyl, R³ is benzoyl, R⁴ is H and R⁶ is methyl, then R¹ᵇ is not H;

or a salt thereof;

comprising the step of:
(i) reacting a compound of Formula (XII):

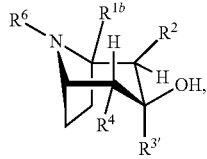

(XII)

wherein $R^{1b}$, $R^2$, $R^{3'}$, $R^4$, $R^6$, $R^7$, $R^8$ and $R^9$ are as defined above; or a salt thereof;
with a second nucleophilic reagent,
to form the compound of Formula (XIII), or a salt thereof.

In one embodiment, in step (i) the second nucleophilic reagent is selected from the group consisting of:
(a) $R^6Y$;
(b) p-nitrophenyl chloroformate, wherein the resulting p-nitrophenoxy derivative is further reacted with the amine of Formula $HNR^7R^8$;
(c) Cl—C(=O)$NR^7R^8$;
(d) O=C=N—$R^8$;
(e) Cl—C(=O)$OR^{11}$;
(f) phosgene, wherein the resulting chloroformate derivative is further reacted with a compound of formula $R^{11}OH$; and,
(g) $R^{11}C$(=O)Cl;
wherein $R^6$, $R^7$, $R^8$, $R^9$ are defined as above; $R^1$ is alkyl, aryl, or heterocyclyl; and Y is a leaving group.

In one embodiment, $R^{1b}$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, or substituted ($C_{2-6}$) alkynyl. In another embodiment, $R^{1b}$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, or substituted ($C_{2-6}$) alkenyl. In yet another embodiment, $R^{1b}$ is H, ($C_{1-6}$) alkyl, substituted ($C_{1-6}$) alkyl, ($C_{3-6}$) cycloalkyl, or substituted ($C_{3-6}$) cycloalkyl. In yet another embodiment, $R^{1b}$ is H, ($C_{1-6}$) alkyl or substituted ($C_{1-6}$) alkyl. In yet another embodiment, $R^{1b}$ is methyl.

In one embodiment, $R^2$ is cyano, —C(=O)H, alkoxycarbonyl, aroxycarbonyl, heterocycloxycarbonyl, acyl, aroyl, heterocycloyl, —C(=$NR^9$)$R^7$, —C(=O)$NR^7R^8$, —C(=S)$NR^7R^8$, —C(=O)N(OMe)Me, or —C(=S)N(OMe)Me. In another embodiment, $R^2$ is cyano, —C(=O)H, alkoxycarbonyl, aroxycarbonyl, heterocycloxycarbonyl, —C(=$NR^9$)$R^7$, —C(=O)$NR^7R^8$, —C(=S)$NR^7R^8$, —C(=O)N(OMe)Me, or —C(=S)N(OMe)Me. In yet another embodiment, $R^2$ is alkoxycarbonyl, aroxycarbonyl, heterocycloxycarbonyl, —C(=O)$NR^7R^8$, —C(=S)$NR^7R^8$, —C(=O)N(OMe)Me, or —C(=S)N(OMe)Me.

In one embodiment, $R^3$ is acyloxy, substituted acyloxy, aroyloxy, substituted aroyloxy, heteroaroyloxy, substituted heteroaroyloxy, —OC(=O)—$NR^7R^8$, ($C_{1-6}$) alkoxy, substituted ($C_{1-6}$) alkoxy, ($C_{3-6}$) cycloalkoxy, substituted ($C_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy. In another embodiment, $R^3$ is acyloxy, substituted acyloxy, aroyloxy, substituted aroyloxy, heteroaroyloxy, substituted heteroaroyloxy, —OC(=O)—$NR^7R^8$, ($C_{1-6}$) alkoxy, substituted ($C_{1-6}$) alkoxy, ($C_{3-6}$) cycloalkoxy, substituted ($C_{3-6}$) cycloalkoxy, (alkoxycarbonyl)oxy, (aroxycarbonyl)oxy, or (heterocycloxycarbonyl)oxy. In yet another embodiment, $R^3$ is acyloxy, substituted acyloxy, aroyloxy, substituted aroyloxy, heteroaroyloxy, substituted heteroaroyloxy, —OC(=O)—$NR^7R^8$, (alkoxycarbonyl)oxy, (aroxycarbonyl)oxy, or (heterocycloxycarbonyl)oxy. In yet another embodiment, $R^3$ is acyloxy, substituted acyloxy, aroyloxy, substituted aroyloxy, heteroaroyloxy, substituted heteroaroyloxy, or —OC(=O)—$NR^7R^8$. In yet another embodiment, $R^3$ is acyloxy, substituted acyloxy, aroyloxy, or substituted aroyloxy.

In one embodiment, $R^4$ is H, ($C_{1-6}$) alkyl, substituted ($C_{1-6}$) alkyl, ($C_{3-4}$ cycloalkyl, substituted ($C_{3-6}$) cycloalkyl, aryl, substituted aryl, heterocyclyl, substituted heterocyclyl, ($C_{1-6}$) alkoxy, aroxy, or heteroaroxy. In another embodiment, $R^4$ is H, ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl. In yet another embodiment, $R^4$ is H, ($C_{1-6}$) alkyl, substituted ($C_{1-6}$) alkyl, ($C_{3-6}$) cycloalkyl, or substituted ($C_{3-6}$) cycloalkyl.

In one embodiment, $R^6$ is H, ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, substituted heterocyclyl, —C(=O)$NR^7R^8$, —$SO_2R^9$, —$SO_2NR^7R^8$, —P(=O)(OR^9)_2$, alkoxycarbonyl, aroxycarbonyl, heterocycloxycarbonyl, acyl, aroyl, or heterocycloyl. In another embodiment, $R^6$ is H, ($C_{1-6}$) alkyl, substituted ($C_{1-6}$) alkyl, ($C_{3-6}$) cycloalkyl, substituted ($C_{3-6}$) cycloalkyl, —C(=O)$NR^7R^8$, —$SO_2R^9$, —$SO_2NR^7R^8$, —P(=O)(OR^9)_2$, alkoxycarbonyl, aroxycarbonyl, heterocycloxycarbonyl, acyl, aroyl, or heterocycloyl. In yet another embodiment, $R^6$ is H, ($C_{1-6}$) alkyl, substituted ($C_{1-6}$) alkyl, ($C_{3-6}$) cycloalkyl, substituted ($C_{3-6}$) cycloalkyl, —C(=O)$NR^7R^8$, —$SO_2R^9$, —$SO_2NR^7R^8$, alkoxycarbonyl, aroxycarbonyl, heterocycloxycarbonyl, acyl, aroyl, or heterocycloyl.

In one embodiment, the compound of Formula (XII) or a salt thereof is prepared by:
(ii) reducing a compound of Formula (XI):

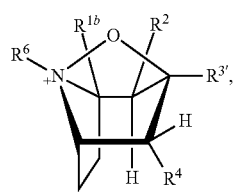

(XI)

wherein $R^{1b}$, $R^2$, $R^{3'}$, $R^4$, $R^6$, $R^7$, $R^8$ and $R^9$ are as defined above; or a salt thereof.

In one embodiment, in step (ii) the compound of Formula (XI) is reduced by treatment with hydrogen gas over Pd—C.

In another embodiment, the compound of Formula (XI) or a salt thereof is prepared by:
(iii) reacting a compound of Formula (X):

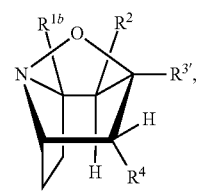

(X)

wherein $R^{1b}$, $R^2$, $R^{3'}$, $R^4$, $R^7$, $R^8$ and $R^9$ are as above; or a salt thereof;

with a first nucleophilic reagent.

In one embodiment, in step (iii) the first nucleophilic reagent is selected from the group consisting of:

(a) an inorganic or organic acid;
(b) $R^6Y$;
(c) $R^9SO_2Cl$;
(d) p-nitrophenyl chloroformate, wherein the resulting p-nitrophenoxy derivative is further reacted with the amine of Formula $HNR^7R^8$;
(e) $Cl-C(=O)NR^7R^8$;
(f) $O=C=N-R^8$;
(g) $Cl-C(=O)OR^{11}$;
(h) phosgene, wherein the resulting chloroformate derivative is further reacted with a compound of formula $R^{11}OH$;
(i) $R^{11}C(=O)Cl$; and,
(j) $Cl-P(=O)(OR_9)_2$;

wherein $R^6$, $R^7$, $R^8$, $R^9$ are defined as above; $R^{11}$ is alkyl, aryl, or heterocyclyl; and Y is a leaving group.

In one embodiment, the compound of Formula (X) or a salt thereof is prepared by:

(iv) promoting rearrangement of a compound of Formula (IX)

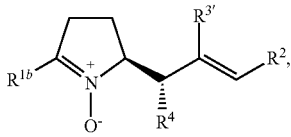

(IX)

wherein $R^{1b}$, $R^2$, $R^{3'}$, $R^4$, $R^7$, $R^8$ and $R^9$ are as above; or a salt thereof.

In one embodiment, in step (iv) the rearrangement is performed at a temperature ranging from about 25° C. to about 200° C. In another embodiment, in step (iv) the rearrangement is performed at a temperature ranging from about 75° C. to about 150° C. In yet another embodiment, in step (iv) the rearrangement is performed under microwave irradiation conditions. In yet another embodiment, in step (iv) the rearrangement is performed at a temperature ranging from about 25° C. to about 200° C. and in the presence of a Lewis acid. In yet another embodiment, the Lewis acid is selected from a group consisting of an aluminum (III) compound, a titanium (IV) compound, a tin (IV) compound, and boron trifluoride. In yet another embodiment, the Lewis acid is an aluminum (III) compound. In yet another embodiment, the Lewis acid is selected from the group consisting of aluminum trichloride, aluminum tribromide, aluminum trifluoride, aluminum trimethoxide, aluminum tri-isopropoxide and aluminum tri-tert-butoxide. In yet another embodiment, the Lewis acid is aluminum tri-tert-butoxide.

In one embodiment, the compound of Formula (IX) or a salt thereof is prepared by:

(v) oxidizing a compound of Formula (VIII),

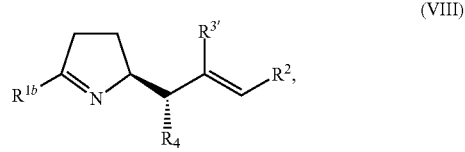

(VIII)

wherein $R^{1b}$, $R^2$, $R^{3'}$, $R^4$, $R^7$, $R^8$ and $R^9$ are as defined above; or a salt thereof.

In one embodiment, in step (v) the compound of Formula (VIII) is oxidized with urea hydrogen peroxide in the presence of methyltrioxorhenium(VII).

In one embodiment, the compound of Formula (VIII) or a salt thereof is prepared by:

(vi) hydrolyzing a compound of Formula (VII):

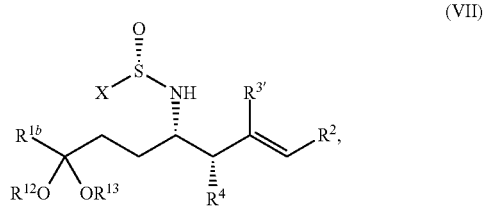

(VII)

wherein:

$R^{1b}$, $R^2$, $R^{3'}$, $R^4$, $R^7$, $R^8$, and $R^9$ are defined as above;

X is para-tolyl, para-tert-butylphenyl, 2,4,6-trimethylphenyl, 2,4,6-triisopropylphenyl, or tert-butyl; and, $R^{12}$ and $R^{13}$ are independently $(C_{1-6})$ alkyl, substituted $(C_{1-6})$ alkyl, benzyl, or substituted benzyl, or $R^{12}$ and $R^{13}$ combine to form an alkylene group selected from the group consisting of $-CH_2CH_2-$, $-CH_2CH_2CH_2-$ and $-CH_2C(CH_3)_2CH_2-$;

or a salt thereof.

In one embodiment, in step (vi) the compound of Formula (VII) is hydrolyzed in the presence of an acid.

In one embodiment, the compound of Formula (VII) is prepared by:

(vii) reacting a compound of Formula (V):

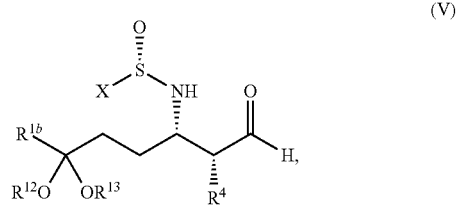

(V)

wherein:

$R^{1b}$, $R^4$, $R^{12}$, $R^{13}$ and X are defined as above; and, or a salt thereof;

with a compound of Formula (VI):

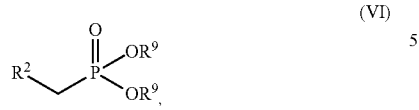

(VI)

wherein $R^2$ and $R^9$ are defined as above, or a salt thereof.

In one embodiment, in step (vii) the compound of Formula (V) and the compound of Formula (VI) are reacted in the presence of a base selected from the group consisting of sodium disilazane, potassium disilazane, lithium disilazane, sodium hydride, potassium hydride, 1,8-bis(dimethylamino) naphthalene, 1,8-diaza-bicycloundec-7-ene, 1,4-diazabicyclo[2.2.2]octane, and 1,5-diaza-bicyclo[4.3.0]non-5-ene.

In one embodiment, in step (vii) the compound of Formula (V) and the compound of Formula (VI) are reacted at a temperature of about −78° C.

In one embodiment, the compound of Formula (V) is prepared by:

(viii) reducing a compound of Formula (IV):

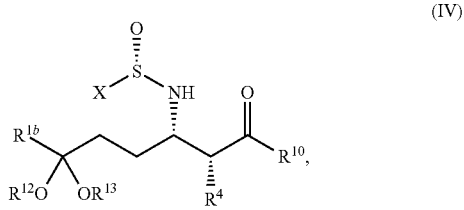

(IV)

wherein
$R^{1b}$, $R^4$, $R^9$, $R^{12}$, $R^{13}$ and X are defined as above; and,
$R^{10}$ is —N(CH$_3$)OCH$_3$ or —OR$^9$,
or a salt thereof.

In one embodiment, in the compound of Formula (IV):
$R^{10}$ is —OR$^9$, and
the compound of Formula (IV) is reduced with a reagent selected from the group consisting of diisobutylaluminum hydride, bis-(4-morpholinyl)aluminum hydride, bis-(N-methyl-piperidinyl)aluminum hydride, lithium aluminum tetrahydride, sodium aluminum tetrahydride, lithium tris-tert-butoxy-aluminum hydride, and sodium bis-isobutyl)aluminum hydride.

In one embodiment, in the compound of Formula (IV):
$R^{10}$ is —N(CH$_3$)OCH$_3$; and,
the compound of Formula (IV) is reduced with a reagent selected from the group consisting of lithium aluminum tetrahydride and bis-isobutyl aluminum hydride.

In one embodiment, the compound of Formula (IV) is prepared by:

(ix) reacting a compound of Formula (II):

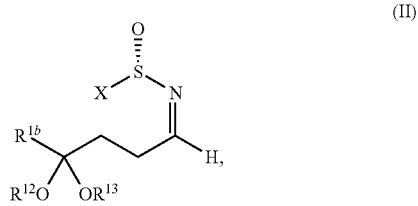

(II)

wherein $R^{1b}$, $R^{12}$, $R^{13}$ and X are defined as above; or a salt thereof;
with a compound of Formula (III):

(III)

wherein $R^4$, $R^9$ and $R^{10}$ are defined as above; or a salt thereof.

In one embodiment, in step (ix) the compound of Formula (II) and the compound of Formula (III) are reacted in the presence of a base selected from the group consisting of sodium disilazane, potassium disilazane, lithium disilazane, sodium hydride, potassium hydride, 1,8-bis(dimethylamino) naphthalene, 1,8-diaza-bicycloundec-7-ene, 1,4-diazabicyclo[2.2.2]octane, and 1,5-diaza-bicyclo[4.3.0]non-5-ene.

In one embodiment, the compound of Formula (XIII) is methyl (1R,2R,3S,5S)-(−)-3-(benzoyloxy)-1,8-dimethyl-8-azabicyclo[3.2.]octane-2-carboxylate, or a salt thereof.

The invention also includes a method of providing anesthesia to a subject in need thereof, wherein the method comprises administering to the subject a therapeutically effective amount of a pharmaceutical formulation comprising a compound of Formula (I):

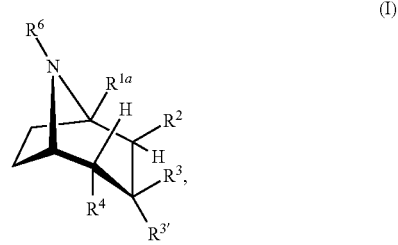

(I)

wherein:
$R^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, or substituted heterocyclyl;
$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;
$R^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-4}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;
$R^{3'}$ is H;
$R^4$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, (C$_{1-6}$) alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

In one embodiment, the pharmaceutical formulation is administered to the subject by parenteral, topical, oral or intranasal route. In another embodiment, the compound of Formula (I) is methyl (1R,2R,3S,5S)-(−)-3-(benzoyloxy)-1,8-dimethyl-8-azabicyclo[3.2.I]octane-2-carboxylate, or a salt thereof. In yet another embodiment, the subject is human.

The invention also includes a method of blocking uptake of a monoamine neurotransmitter in a subject in need thereof, wherein the neurotransmitter is selected from the group consisting of serotonin, norepinephrine and dopamine, wherein the method comprises administering to the subject a therapeutically effective amount of a pharmaceutical formulation comprising a compound of Formula (I):

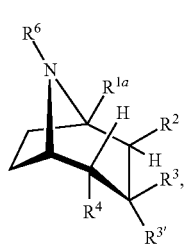

(I)

wherein:
$R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-4}$ alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^3$ is acyloxy, substituted acyloxy, aroyloxy, substituted aroyloxy, heteroaroyloxy, substituted heteroaroyloxy, —OC(=O)—NR$^7$R$^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

$R^{3'}$ is H;

$R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

In one embodiment, the neurotransmitter is serotonin. In another embodiment, the neurotransmitter is norepinephrine. In yet another embodiment, the neurotransmitter is dopamine. In yet another embodiment, the pharmaceutical formulation is administered to the subject by parenteral, topical, oral or intranasal route. In yet another embodiment, the compound of Formula (I) is methyl (1R,2R,3S,5S)-(−)-3-(benzoyloxy)-1,8-dimethyl-8-azabicyclo[3.2.I]octane-2-carboxylate, or a salt thereof. In yet another embodiment, the subject is human.

The invention is also directed to a method of treating depression in a subject in need thereof. The method comprises administering to the subject a therapeutically effective amount of a pharmaceutically formulation comprising a compound of Formula (I), as indicated above. In yet another embodiment, the compound of Formula (I) is methyl (1R,2R,3S,5)-(−)-3-(benzoyloxy)-1,8-dimethyl-8-azabicyclo[3.2.I] octane-2-carboxylate, or a salt thereof. In yet another embodiment, the subject is human.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DEFINITIONS

The definitions used in this application are for illustrative purposes and do not limit the scope used in the practice of the invention.

In the following paragraphs some of the definitions include examples. The examples are intended to be illustrative, and not limiting.

Unless defined otherwise, all technical and scientific terms used herein generally have the same meaning as commonly understood by one of ordinary skill in the art to which this invention belongs. Generally, the nomenclature used herein and the laboratory procedures in analytical, organic and protein chemistries are those well known and commonly employed in the art.

As used in the specification and the appended claims, the singular forms "a," "an," and "the" include plural referents unless the context clearly dictates otherwise.

The term "about" will be understood by persons of ordinary skill in the art and will vary to some extent on the context in which it is used.

As used herein, the term "monoamine neurotransmitter" refers to a neurotransmitter or neuromodulator that contains an amino group that is connected to an aromatic ring by an ethylene linker. Non-limiting examples of monoamine neurotransmitters are histamine, thyronamines, catecholamines (such as, but not limited to, dopamine, norepinephrine and epinephrine), tryptamines (such as, but not limited to, serotonin and melatonin) and trace amines (such as, but not limited, β-phenylethylamine, tyramine, tryptamine, octapamine and 3-iodothyronamine). In one embodiment, the monoamine neurotransmitter is dopamine, norepinephrine or serotonin.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tut-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$) cycloalkyl, particularly cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A functional group representing an alkene is exemplified by —$CH_2$—CH═$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —$NH_2$, —$N(CH_3)_2$, —C(═O)OH, trifluoromethyl, —C(═O)O($C_1$-$C_4$)alkyl, —C(═O)$NH_2$, —$SO_2NH_2$, —C(═NH)$NH_2$, and —$NO_2$, preferably containing one or two substituents selected from halogen, —OH, alkoxy, —$NH_2$, trifluoromethyl, —$N(CH_3)_2$, and —C(═O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(═O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—$CH_3$, —CH═CH—$CH_2$—OH, —$CH_2$—CH═N—$OCH_3$, —CH═CH—$N(CH_3)$—$CH_3$, and —$CH_2$—CH═CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

"Medical intervention," as used herein, means a set of one or more medical procedures or treatments that are required for ameliorating the effects of delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

A "subject," as used therein, may be a human or non-human mammal. Non-human mammals include, for example, livestock and pets, such as ovine, bovine, porcine, canine, feline and murine mammals. Preferably, the subject is human.

The language "effective amount" or "therapeutically effective amount" refers to a non-toxic but sufficient amount of the composition used in the practice of the invention that is effective to provide anesthesia in a subject and/or inhibit reuptake of a monoamine neurotransmitter in a subject. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, a "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

A "pharmaceutically acceptable carrier" refers herein to a composition suitable for delivering an active pharmaceutical ingredient, such as a compound of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed. Mack Publishing Co., 1985, Easton, Pa.), the disclosure of which is incorporated herein by reference.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating obesity in a subject.

As used herein, the term "applicator" is used to identify any device including, but not limited to, a hypodermic syringe, a pipette, and the like, for administering the compounds and compositions used in the practice of the invention.

According to convention, bonds to atoms above the plane of a molecule are shown with a bold wedge: ▬▬. Bonds to atoms below the plane are shown with a wedge of parallel lines: ׀׀׀׀׀. The following bond between sulfur and oxygen is understood to represent a double bond: S⫶⫶⫶O.

DETAILED DESCRIPTION OF THE INVENTION

Figure 1:
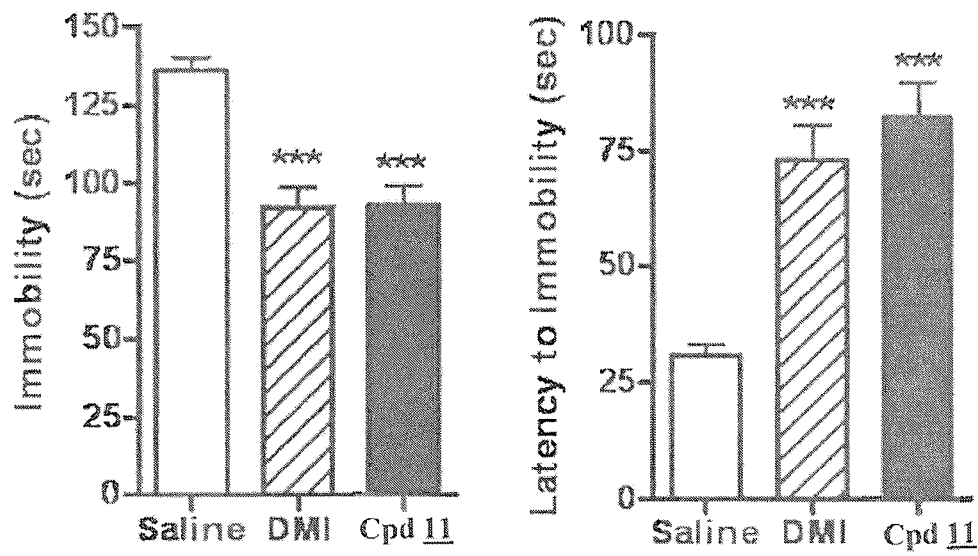
FIG. 1 shows the effect of a forced swim test model of antidepressant-like activity in C57BL/6 male mice. The tricyclic antidepressant desipramine (DMI, 10 mg/kg i.p.) or methyl (1R,2R,3S,5S)-(−)-3-(benzoyloxy)-1,8-dimethyl-8-azabicyclo [3.2.1 ]octane-2-carboxylate (Compound 11; 30 mg/kg i.p.) decreased immobility time (left panel) and increased latency to first episode of immobility (right panel) compared with saline-injected controls. Data are mean ±SEM (vertical bar). ***P<0.001, n=7-9 (One-way ANOVA and Bonferroni post-hoc tests).

The present invention relates to the unexpected discovery of a synthetic methodology that allows the chiral synthesis of a cocaine analog with stereospecific control over the substituents installed at the C-1, C-2, C-3, C-4 and N-8 positions of the tropane bicyclic scaffold. Such cocaine analogs were not accessible by the synthetic methods previously disclosed in the literature, and may be used in studying cocaine pharmacology, treating cocaine addiction, inhibiting reuptake of one or more monoamine neurotransmitters, inhibiting depression and/or inducing anesthesia in a subject.

The compounds provide central effects, such as dopamine transporter (DAT) inhibition and anti-depressant effect, but are essentially devoid of cocaine's locomotor stimulatory activity. The lack of stimulation is not due to poor brain penetration. Pharmacokinetic assay demonstrated that methyl (1R,2R,3S,5S)-(−)-3-(benzoyloxy)-1,8-dimethyl-8-azabicyclo3.2.I]octane-2-carboxylate (compound 11) occupies the brain as readily as cocaine.

The compounds are believed to preferentially interact with an open-to-out (outward-facing) DAT conformation, similar to cocaine, based on in silico molecular modeling of the hDAT protein and flexible ligand docking performed on compounds 11 and 11d. The assay (data not shown) was conducted according to the method of Schmitt et al., (2010) *J Neurochem* 112:1605-1618.

Compounds of the Invention

In one embodiment, the compounds of the invention are prepared using the synthetic methods of the present invention.

The present invention includes a compound of Formula (I):

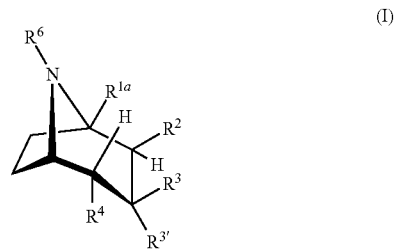

(I)

wherein:
$R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^3$ is acyloxy, substituted acyloxy, aroyloxy, substituted aroyloxy, heteroaroyloxy, substituted heteroaroyloxy, —OC(=O)—NR$^7$R$^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

$R^{3'}$ is H;

$R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

The present invention also includes a compound of Formula (IV):

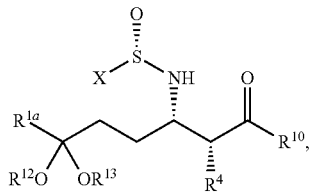

(IV)

wherein:
- $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;
- $R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;
- $R^9$ is $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;
- $R^{10}$ is —N(CH$_3$)OCH$_3$ or —OR$^9$;
- $R^{12}$ and $R^{13}$ are independently $(C_{1-6})$ alkyl, substituted $(C_{1-6})$ alkyl, benzyl, or substituted benzyl, or $R^{12}$ and $R^{13}$ combine to form an alkylene group selected from the group consisting of —CH$_2$CH$_2$—, —CH$_2$CH$_2$CH$_2$— and —CH$_2$C(CH$_3$)$_2$CH$_2$—; and,
- X is para-tolyl, para-tert-butylphenyl, 2,4,6-trimethylphenyl, 2,4,6-triisopropylphenyl, or tert-butyl;

or a salt thereof.

The present invention further includes a compound of Formula (V):

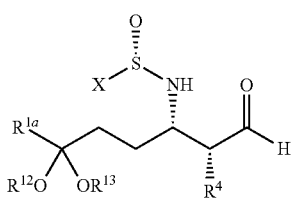

(V)

wherein:
- is $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;
- $R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;
- $R^{12}$ and $R^{13}$ are independently $(C_{1-6})$ alkyl, substituted $(C_{1-6})$ alkyl, benzyl, or substituted benzyl, or $R^{12}$ and $R^{13}$ combine to form an alkylene group selected from the group consisting of —CH$_2$CH$_2$—, —CH$_2$CH$_2$CH$_2$— and —CH$_2$C(CH$_3$)$_2$CH$_2$—; and,
- X is para-tolyl, para-tert-butylphenyl, 2,4,6-trimethylphenyl, 2,4,6-triisopropylphenyl, or tert-butyl;

or a salt thereof

The present invention also includes a compound of Formula (VII):

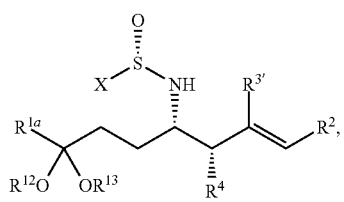

(VII)

wherein:
- $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;
- $R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;
- $R^{3'}$ is H;
- $R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;
- $R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;
- each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;
- $R^{12}$ and $R^{13}$ are independently $(C_{1-6})$ alkyl, substituted $(C_{1-6})$ alkyl, benzyl, or substituted benzyl, or $R^{12}$ and $R^{13}$ combine to form an alkylene group selected from the group consisting of —CH$_2$CH$_2$—, —CH$_2$CH$_2$CH$_2$— and —CH$_2$C(CH$_3$)$_2$CH$_2$—; and
- X is para-tolyl, para-tert-butylphenyl, 2,4,6-trimethylphenyl, 2,4,6-triisopropylphenyl, or tert-butyl;

or a salt thereof.

The present invention also includes a compound of Formula (VIII):

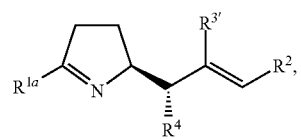

(VIII)

wherein:
- $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted ($C_{2-6}$) alkenyl, ($C_{2-6}$) alkynyl, substituted ($C_{2-6}$) alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^{3'}$ is H;

$R^4$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, substituted heterocyclyl, ($C_{1-6}$) alkoxy, aroxy, or heteroaroxy;

$R^7$ and $R^8$ are independently H, ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl; and, each occurrence of $R^9$ is independently ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl;

or a salt thereof.

The present invention also includes a compound of Formula (IX):

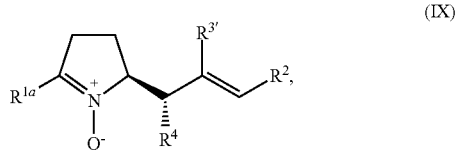

wherein:

$R^{1a}$ is ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^{3'}$ is H;

$R^4$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, substituted heterocyclyl, ($C_{1-6}$) alkoxy, aroxy, or heteroaroxy;

$R^7$ and $R^8$ are independently H, ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl; and, each occurrence of $R^9$ is independently ($C_{1-6}$) alkyl, substituted ($C_{1-6}$) alkyl, ($C_{3-4}$ cycloalkyl, substituted ($C_{3-6}$) cycloalkyl, aryl, substituted aryl, heterocyclyl, or substituted heterocyclyl;

or a salt thereof.

The present invention further includes a compound of Formula (X):

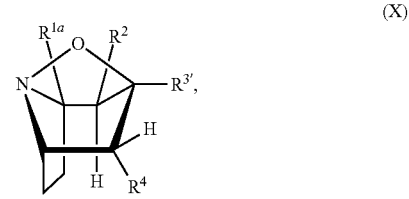

wherein:

$R^{1a}$ is ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^{3'}$ is H;

$R^4$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, substituted heterocyclyl, ($C_{1-6}$) alkoxy, aroxy, or heteroaroxy;

$R^7$ and $R^8$ are independently H, ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl;

each occurrence of $R^9$ is independently ($C_{1-6}$) alkyl, substituted ($C_{1-6}$) alkyl, ($C_{3-6}$) cycloalkyl, substituted ($C_{3-6}$) cycloalkyl, aryl, substituted aryl, heterocyclyl, or substituted heterocyclyl;

or a salt thereof.

The present invention also includes a compound of Formula (XI):

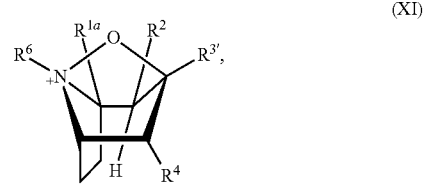

wherein:

$R^{1a}$ is ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, substituted ($C_{2-6}$) alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

$R^{3'}$ is H;

$R^4$ is H, ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, (C$_{1-6}$) alkoxy, aroxy, or heteroaroxy;

R$^6$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

R$^7$ and R$^8$ are independently H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;

each occurrence of R$^9$ is independently (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;

or a salt thereof.

The present invention further includes a compound of Formula (XII):

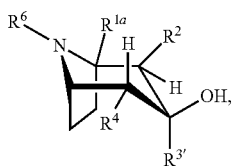

(XII)

wherein:

R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, or substituted heterocyclyl;

R$^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

R$^{3'}$ is H;

R$^4$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, (C$_{1-6}$) alkoxy, aroxy, or heteroaroxy;

R$^6$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

R$^7$ and R$^8$ are independently H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;

each occurrence of R$^9$ is independently (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;

or a salt thereof.

In one embodiment, R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, or substituted (C$_{2-6}$) alkynyl. In another embodiment, R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, or substituted (C$_{2-6}$) alkenyl. In yet another embodiment, R$^{1a}$ is (C$_{1-6}$) alkyl, substituted (C$_{1-6}$) alkyl, (C$_{3-6}$) cycloalkyl, or substituted (C$_{3-6}$) cycloalkyl. In yet another embodiment, R$^{1a}$ is (C$_{1-6}$) alkyl, or substituted (C$_{1-6}$) alkyl. In yet another embodiment, R$^{1a}$ is methyl.

In one embodiment, R$^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, or —C(=S)N(OMe)Me. In another embodiment, R$^2$ is cyano, —C(=O)H, alkoxycarbonyl, aroxycarbonyl, heterocycloxycarbonyl, —C(=NR$^9$)R$^7$, —C(=O)NR$^7$R$^8$, —C(=S)NR$^7$R$^8$, —C(=O)N(OMe)Me, or —C(=S)N(OMe)Me. In yet another embodiment, R$^2$ is alkoxycarbonyl, aroxycarbonyl, heterocycloxycarbonyl, —C(=O)NR$^7$R$^8$, —C(=S)NR$^7$R$^8$, —C(=O)N(OMe)Me or —C(=S)N(OMe)Me.

In one embodiment, R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy. In another embodiment, R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, (alkoxycarbonyl)oxy, (aroxycarbonyl)oxy, or (heterocycloxycarbonyl)oxy. In another embodiment, R$^3$ is acyloxy, substituted acyloxy, aroyloxy, substituted aroyloxy, heteroaroyloxy, substituted heteroaroyloxy, —OC(=O)—NR$^7$R$^8$, (alkoxycarbonyl)oxy, (aroxycarbonyl)oxy, or (heterocycloxycarbonyl)oxy. In yet another embodiment, R$^3$ is acyloxy, substituted acyloxy, aroyloxy, substituted aroyloxy, heteroaroyloxy, substituted heteroaroyloxy, or —OC(=O)—NR$^7$R$^8$. In yet another embodiment, R$^3$ is acyloxy, substituted acyloxy, aroyloxy, or substituted aroyloxy.

In one embodiment, R$^4$ is H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, substituted heterocyclyl, (C$_{1-6}$) alkoxy, aroxy, or heteroaroxy. In another embodiment, R$^4$ is H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl. In yet another embodiment, R$^4$ is H, (C$_{1-6}$) alkyl, substituted (C$_{1-6}$) alkyl, (C$_{3-6}$) cycloalkyl, or substituted (C$_{3-6}$) cycloalkyl.

In one embodiment, R$^6$ is H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl. In another embodiment, R$^6$ is H, (C$_{1-6}$) alkyl, substituted (C$_{1-6}$) alkyl, (C$_{3-6}$) cycloalkyl, substituted (C$_{3-6}$) cycloalkyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl. In another embodiment, R$^6$ is H, (C$_{1-6}$) alkyl, substituted (C$_{1-6}$) alkyl, (C$_{3-6}$) cycloalkyl, substituted (C$_{3-6}$)

or a salt thereof. —C(=O)NR⁷R⁸, —SO₂R⁹, —SO₂NR⁷R⁸, alkoxycarbonyl, aroxycarbonyl, heterocycloxycarbonyl, acyl, aroyl, or heterocycloyl.

In one embodiment, $R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, or substituted aryl. In another embodiment, $R^7$ and $R^8$ are independently H, $(C_{1-6})$ alkyl, substituted $(C_{1-6})$ alkyl, $(C_{3-6})$ cycloalkyl, or substituted $(C_{3-6})$ cycloalkyl.

In one embodiment, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, or substituted aryl. In another embodiment, each occurrence of $R^9$ is independently $(C_{1-6})$ alkyl, substituted $(C_{1-6})$ alkyl, $(C_{3-6})$ cycloalkyl, or substituted $(C_{3-6})$ cycloalkyl.

In one embodiment, $R^{12}$ and $R^{13}$ are independently $(C_{1-6})$ alkyl, substituted $(C_{1-6})$ alkyl, or $R^{12}$ and $R^{13}$ combine to form an alkylene group selected from the group consisting of —CH₂CH₂—, —CH₂CH₂CH₂— and —CH₂C(CH₃)₂CH₂—. In another embodiment, $R^{12}$ and $R^{13}$ are methyl. In another embodiment, $R^{12}$ and $R^{13}$ combine to form an alkylene group selected from the group consisting of —CH₂CH₂—, —CH₂CH₂CH₂— and —CH₂C(CH₃)₂CH₂—. In yet another embodiment, $R^{12}$ and $R^{13}$ combine to form the alkylene group —CH₂CH₂—. In yet another embodiment, $R^{12}$ and $R^{13}$ combine to form the alkylene group —CH₂CH₂CH₂—. In yet another embodiment, $R^{12}$ and $R^{13}$ combine to form the alkylene group —CH₂C(CH₃)₂CH₂—.

Salts of the Compounds of the Invention

The compounds of the invention may form salts with acids or bases, and such salts are included in the present invention. In one embodiment, the salts are pharmaceutically-acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Synthetic Processes of the Invention

In one aspect, compound (XIII) of the invention may be prepared according to the following synthetic scheme:

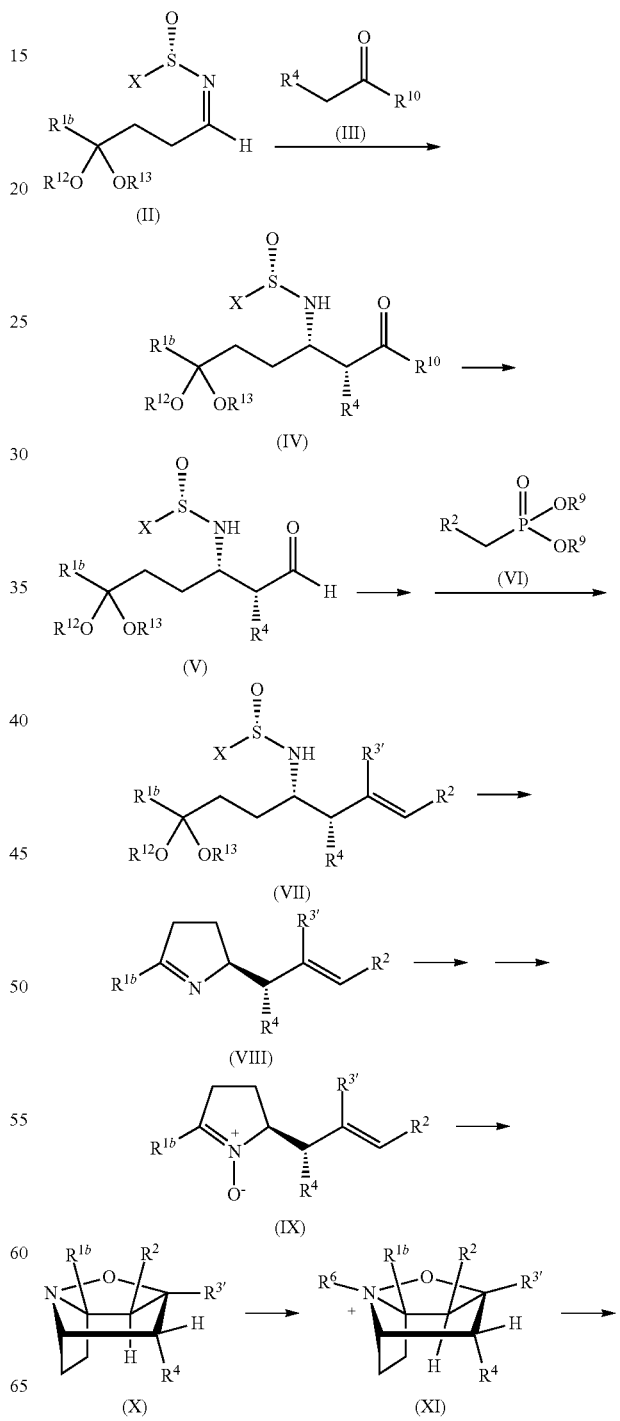

-continued

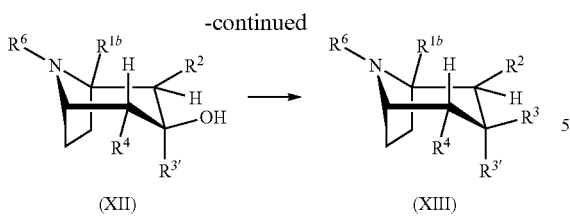

(XII) → (XIII)

The (S)-sulfinimine of Formula (II) is used as the starting material of the processes of the invention:

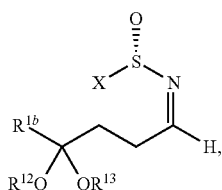

(II)

wherein:

$R^{1b}$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;

$R^{12}$ and $R^{13}$ are independently $(C_{1-6})$ alkyl, substituted $(C_{1-6})$ alkyl, benzyl, or substituted benzyl, or $R^{12}$ and $R^{13}$ combine to form an alkylene group selected from the group consisting of —CH$_2$CH$_2$—, —CH$_2$CH$_2$CH$_2$— and —CH$_2$C(CH$_3$)$_2$CH$_2$—; and X is para-tolyl, para-tert-butylphenyl, 2,4,6-trimethylphenyl, 2,4,6-triisopropylphenyl, or tert-butyl;

or a salt thereof.

The compound of Formula (II) may be prepared by any synthetic method known to those skilled in the art. In a non-limiting example, compound (II) may be prepared according to Davis et al., 2009, Org. Lett. 11:1647-1650.

The compound of Formula (II) may be reacted with a compound of Formula (III):

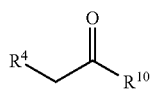

(III)

wherein:

$R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^{10}$ is —N(CH$_3$)OCH$_3$ or —OR$^9$; and, each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; or a salt thereof, to form a compound of Formula (IV):

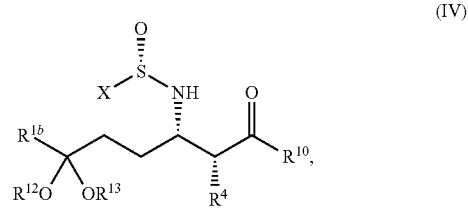

(IV)

wherein $R^{1b}$, $R^4$, $R^9$, $R^{10}$, $R^{12}$, $R^{13}$ and X are as defined above, or a salt thereof.

The reaction may be run in an inert solvent, such as, but not limited to, dichloromethane, ethyl ether, tetrahydrofuran or mixtures thereof, at a temperature ranging from about −100° C. to about 25° C. In one embodiment, the reaction is run at about −78° C. The reaction may be run in the presence of a base, such as, but not limited to, sodium disilazane, potassium disilazane, lithium disilazane, sodium hydride, potassium hydride or 1,8-bis(dimethylamino)naphthalene. The reaction mixture may be worked up using methods known to those skilled in the art, such as quenching with an aqueous solution of ammonium chloride or sodium bisulfate, and the compound of Formula (IV) may be isolated from the resulting mixture by methods such as chromatography, precipitation, or liquid-phase extraction.

The compound of Formula (IV) may be reduced to form a compound of Formula (V):

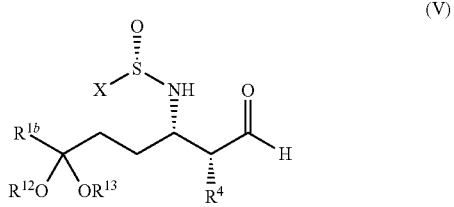

(V)

wherein $R^{1b}$, $R^4$, $R^{12}$, $R^{13}$ and X are defined as above;

or a salt thereof.

The reaction may be run in a solvent such as, but not limited to, ethyl ether, tetrahydrofuran, toluene or mixtures thereof, at a temperature ranging from about −100° C. to about 25° C. In one embodiment, the reaction is run at about −78° C.

If $R^{10}$ is —OR$^9$ in the compound of Formula (IV), the reduction of the compound of Formula (IV) may be performed using a reagent such as, but not limited to, diisobutylaluminum hydride (DIBAL-H), bis-(4-morpholinyl)aluminum hydride, bis-(N-methyl-piperidinyl)aluminum hydride, lithium aluminum tetrahydride, sodium aluminum tetrahydride, lithium tris-tert-butoxy-aluminum hydride, or sodium bis-isobutyl)aluminum hydride.

If $R^{10}$ is —N(CH$_3$)OCH$_3$ in the compound of Formula (IV), the reduction of the compound of Formula (IV) may be performed using a reagent such as, but not limited to, lithium aluminum tetrahydride or bis-isobutyl aluminum hydride.

The compound of Formula (V) may be reacted with a compound of Formula (VI):

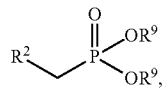

(VI)

wherein:
each occurrence of $R^9$ is independently as defined above;
$R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$; and,
$R^7$ and $R^8$ are independently H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;
or a salt thereof;
to form a compound of Formula (VII):

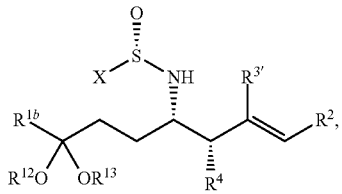

(VII)

wherein $R^{1b}$, $R^2$, $R^4$, $R^7$, $R^8$, $R^9$, $R^{12}$, $R^{13}$ and X are as defined above, and
$R^{3'}$ is H; or a salt thereof.

The reaction may be run in an inert solvent, such as, but not limited to, dichloromethane, acetonitrile, propionitrile, tetrahydrofuran, diethyl ether, dimethylformamide or mixtures thereof, at a temperature ranging from about −50° C. to about 50° C. In an embodiment, the reaction is run at about 25° C. The reaction may be run in the presence of a base, such as, but not limited to, sodium disilazane, potassium disilazane, lithium disilazane, sodium hydride, potassium hydride, 1,8-bis(dimethylamino)naphthalene, DBU (1,8-diaza-bicycloundec-7-ene), DABCO (1,4-diazabicyclo[2.2.2]octane) or DBN (1,5-diaza-bicyclo[4.3.0]non-5-ene). The reaction mixture may be worked up using methods known to those skilled in the art, such as quenching with an aqueous solution of ammonium chloride or sodium bisulfate, and the compound of Formula (VII) may be isolated from the resulting mixture by methods such as chromatography, precipitation, or liquid-phase extraction.

The compound of Formula (VII) may be hydrolyzed to a compound of Formula (VIII):

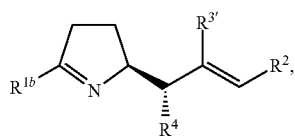

(VIII)

wherein $R^{1b}$, $R^2$, $R^{3'}$, $R^4$, $R^7$, $R^8$ and $R^9$ are as defined above,
or a salt thereof.

The reaction may be run in a solvent such as, but not limited to, methanol, ethanol, water, tetrahydrofuran, ethyl ether, or mixtures thereof. The reaction may be run in the presence of an acid, such as, but not limited to, hydrochloric acid, hydrobromic acid, trifluoroacetic acid or methanesulfonic acid, wherein the acid may be added as an aqueous solution, an anhydrous solution, or neat. The compound of Formula (VIII) may be isolated from the resulting mixture by methods such as chromatography, precipitation, or liquid-phase extraction.

The compound of Formula (VIII) may be oxidized to a compound of Formula (IX):

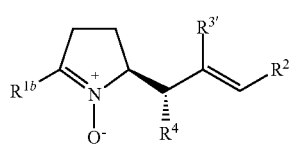

(IX)

wherein $R^{1b}$, $R^2$, R, $R^4$, $R^7$, $R^8$ and $R^9$ are as defined above, or a salt thereof.

The reaction may be performed in a solvent such as, but not limited to, dichloromethane, methanol, tetrahydrofuran, diethyl ether, or mixtures thereof, using a reagent such as, but not limited to, urea hydrogen peroxide in the presence of sodium tungstate, urea hydrogen peroxide in the presence of methyltrioxorhenium(VII), meta-chloroperbenzoic acid (mCPBA), potassium peroxymonosulfate (Oxone™), hydrogen peroxide in the presence of titanium silicalite molecular sieves, hydrogen peroxide in the presence of sodium tungstate, or mercury(II) oxide in the presence of para-benzoquinone.

The compound of Formula (IX) may be submitted to a rearrangement reaction to form a compound of Formula (X):

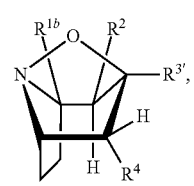

(X)

wherein $R^{1b}$, $R^2$, $R^{3'}$, $R^4$, $R^7$, $R^8$ and $R^9$ are as defined above,
or a salt thereof.

In one embodiment, the rearrangement reaction is performed in a solvent such as, but not limited to, toluene, dimethylsulfoxide, dimethylformamide, tetrahydrofuran, or mixtures thereof. In another embodiment, the rearrangement reaction is performed with the neat compound of Formula (IX). In yet another embodiment, the rearrangement reaction is performed at a temperature ranging from about 25° C. to about 200° C. In yet another embodiment, the rearrangement reaction is performed at a temperature ranging from about 75° C. to about 150° C. In yet another embodiment, the rearrangement reaction is performed at a temperature of about 110° C. In yet another embodiment, the rearrangement reaction is performed under microwave irradiation conditions. In yet another embodiment, the rearrangement reaction is performed at a temperature ranging from about 25° C. to about 200° C. and in the presence of a Lewis acid. In yet another embodiment, the Lewis acid is selected from a group consisting of an aluminum (III) compound, a titanium (IV) compound, a tin (IV) compound, and boron trifluoride. In yet another embodiment, the Lewis acid is an aluminum (III) compound. In yet another embodiment, the Lewis acid is selected from the group consisting of aluminum trichloride, aluminum tribromide, aluminum trifluoride, aluminum trimethoxide, aluminum tri-isopropoxide and aluminum tri-tert-butoxide. In yet another embodiment, the Lewis acid is aluminum tri-tert-butoxide.

The compound of Formula (X) may be reacted with a first nucleophilic reagent to form a compound of formula (XI):

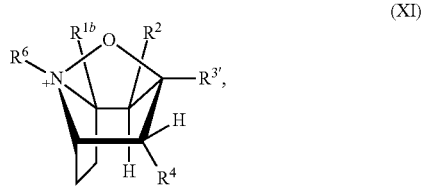

(XI)

wherein:
$R^{1b}$, $R^2$, $R^{3'}$, $R^4$, $R^7$, $R^8$ and $R^9$ are as defined above; and,
$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;
with the proviso that if $R^2$ is methoxycarbonyl, $R^3$ is benzoyl, $R^4$ is H and $R^6$ is methyl, then $R^{1b}$ is not H;
or a salt thereof.

If, in the compound of Formula (XI), $R^6$ is H, the compound of Formula (XI) may be prepared by reacting the compound of Formula (X) with an inorganic or organic acid. The reaction may be run in a solvent such as, but not limited to, dimethylformamide, tetrahydrofuran, dichloromethane, or mixtures thereof.

If, in the compound of Formula (XI), $R^6$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl, the compound of Formula (XI) may be prepared by reacting the compound of Formula (X) with a first nucleophilic reagent of formula R$_6$Y, wherein Y is a leaving group, such as, not limited to, halide, tosylate, mesylate or triflate. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XI), $R^6$ is —SO$_2$R$^9$, the compound of Formula (XI) may be prepared by reacting the compound of Formula (X) with a first nucleophilic reagent of formula R$^9$SO$_2$Cl, wherein R$^9$ is as defined above. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XI), $R^6$ is —C(=O)NR$^7$R$^8$, the compound of Formula (XI) may be prepared by reacting the compound of Formula (X) with the first nucleophilic reagent para-nitrophenyl-chloroformate, wherein the resulting para-nitrophenoxy derivative is treated with the amine of formula HNR$^7$R$^8$. If, in the compound of Formula (XI), $R^6$ is —C(=O)NR$^7$R$^8$, wherein R$^7$ and R$^8$ are not H, the compound of Formula (XI) may be prepared by reacting the compound of Formula (X) with a first nucleophilic reagent of formula Cl—C(=O)NR$^7$R$^8$. If, in the compound of Formula (XI), $R^6$ is —C(=O)NR$^7$R$^8$, wherein R$^7$ is H and R$^8$ is not H, the compound of Formula (XI) may be prepared by reacting the compound of Formula (X) with a first nucleophilic reagent of formula O=C=N—R$^8$. The reactions may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XI), $R^6$ is alkoxycarbonyl, aroxycarbonyl, or heterocycloxycarbonyl, the compound of Formula (XI) may be prepared by reacting the compound of Formula (X) with a first nucleophilic reagent of formula Cl—C(=O)OR$^{11}$, wherein R$^{11}$ is alkyl, aryl or heterocyclyl. Alternatively, the compound of Formula (XI) may be prepared by reacting the compound of Formula (X) with the nucleophilic reagent phosgene, and then treating the product with R$^{11}$OH, wherein R$^{11}$ is alkyl, aryl or heterocyclyl. Phosgene equivalents, such as diphosgene, triphosgene or diimidazolylcarbonyl, may also be used in this reaction. The reactions may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XI), $R^6$ is acyl, aroyl, or heterocycloyl, the compound of Formula (XI) may be prepared by reacting the compound of Formula (X) with a first nucleophilic reagent of formula R$^{11}$C(=O)Cl, wherein R$^{11}$ is alkyl, aryl or heterocyclyl. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XI), $R^6$ is —P(=O)(OR$^9$)$_2$, the compound of Formula (XI) may be prepared by reacting the compound of Formula (X) with a first nucleophilic reagent of formula Cl—P(=O)(OR$^9$)$_2$. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof The compound of Formula (XI) may be reduced to a compound of Formula (XII):

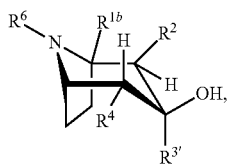

(XII)

wherein $R^{1b}$, $R^2$, $R^{3'}$, $R^4$, $R^6$, $R^7$, $R^8$ and $R^9$ are as defined above;

with the proviso that if $R^2$ is methoxycarbonyl, $R^3$ is benzoyl, $R^4$ is H and $R^6$ is methyl, then $R^{1b}$ is not H;

or a salt thereof.

In one embodiment, the compound of Formula (XI) is reduced with hydrogen gas over Pd—C, in a solvent such as, but not limited to, methanol, ethanol, tetrahydrofuran or mixtures thereof, to form the compound of Formula (XII). In another embodiment, the compound of Formula (XI) is reduced with ammonium formate in the presence of Pd—C. In yet another embodiment, the compound of Formula (XI) is reduced with $Mo(CO)_6$. In yet another embodiment, the compound of Formula (XI) is reduced with metallic zinc and acetic acid. In yet another embodiment, the compound of Formula (XI) is reduced with samarium iodide.

The compound of Formula (XII) may be reacted with a second nucleophilic reagent to form a compound of formula (XIII):

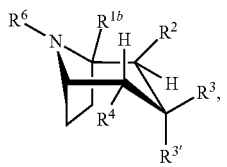

(XIII)

wherein:

$R^{1b}$, $R^2$, $R^{3'}$, $R^4$, $R^6$, $R^7$, $R^8$ and $R^9$ are as defined above; and, $R^3$ is acyloxy, substituted acyloxy, aroyloxy, substituted aroyloxy, heteroaroyloxy, substituted heteroaroyloxy, —OC(=O)—$NR^7R^8$, ($C_{1-6}$) alkoxy, substituted ($C_{1-6}$) alkoxy, ($C_{3-6}$) cycloalkoxy, substituted ($C_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

with the proviso that if $R^2$ is methoxycarbonyl, $R^3$ is benzoyl, $R^4$ is H and $R^6$ is methyl, then $R^{1b}$ is not H;

or a salt thereof.

If, in the compound of Formula (XIII), $R^3$ is acyloxy, substituted acyloxy, aroyloxy, substituted aroyloxy, heteroaroyloxy, or substituted heteroaroyloxy, the compound of Formula (XIII) may be prepared by reacting the compound of Formula (XII) with a second nucleophilic reagent of formula $R^{11}C(=O)Cl$, wherein $R^{11}$ is alkyl, aryl or heterocyclyl. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XIII), $R^3$ is —OC(=O)$NR^7R^8$, the compound of Formula (XIII) may be prepared by reacting the compound of Formula (XII) with the second nucleophilic reagent para-nitrophenyl-chloroformate, wherein the resulting para-nitrophenoxy derivative is treated with the amine of formula $HNR^7R^8$. If, in the compound of Formula (XIII), $R^3$ is —OC(=O)$NR^7R^8$, wherein $R^7$ and $R^8$ are not H, the compound of Formula (XIII) may be prepared by reacting the compound of Formula (XII) with a second nucleophilic reagent of formula Cl—C(=O)$NR^7R^8$. If, in the compound of Formula (XIII), $R^3$ is —OC(=O)$NR^7R^8$, wherein $R^7$ is H and $R^8$ is not H, the compound of Formula (XIII) may be prepared by reacting the compound of Formula (XII) with a second nucleophilic reagent of formula O=C=N—$R^8$. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XIII), $R^3$ is ($C_{1-6}$) alkoxy, substituted ($C_{1-6}$) alkoxy, ($C_{3-6}$) cycloalkoxy, and substituted ($C_{3-6}$) cycloalkoxy, aroxy, substituted aroxy, heterocycloxy, or substituted heterocycloxy, the compound of Formula (XIII) may be prepared by reacting the compound of Formula (XII) with a second nucleophilic reagent of formula $R_6Y$, wherein Y is a leaving group, such as, not limited to, halide, tosylate, mesylate or triflate. The reaction may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

If, in the compound of Formula (XIII), $R^3$ is (alkoxycarbonyl)oxy, (aroxycarbonyl)oxy, or (heterocycloxycarbonyl)oxy, the compound of Formula (XIII) may be prepared by reacting the compound of Formula (XII) with a second nucleophilic reagent of formula Cl—C(=O)$OR^{11}$, wherein $R^{11}$ is alkyl, aryl or heterocyclyl. Alternatively, the compound of Formula (XIII) may be prepared by reacting the compound of Formula (XII) with the second nucleophilic reagent phosgene, and then treating the product with $R^{11}OH$, wherein $R^{11}$ is alkyl, aryl or heterocyclyl. Phosgene equivalents, such as diphosgene, triphosgene or diimidazolylcarbonyl, may also be used in this reaction. The reactions may be run in a solvent such as, but not limited to, dimethylformamide, tetrahydrofuran, dichloromethane, or mixtures thereof, and may be run in the presence of a base, such as, but not limited to, triethylamine, diisopropylethylamine, pyridine, or mixtures thereof.

In one embodiment, $R^{1b}$ is ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, substituted ($C_{2-6}$) alkenyl, ($C_{2-6}$) alkynyl, or substituted ($C_{2-6}$) alkynyl. In another embodiment, $R^{1b}$ is ($C_{1-6}$) alkyl, substituted ($C_{1-6}$) alkyl, ($C_{3-6}$) cycloalkyl, substituted ($C_{3-6}$) cycloalkyl, ($C_{2-6}$) alkenyl, or substituted ($C_{2-6}$) alkenyl. In yet another embodiment, $R^{1b}$ is ($C_{1-6}$) alkyl, substituted ($C_{1-6}$) alkyl, ($C_{3-6}$) cycloalkyl, or substituted ($C_{3-6}$) cycloalkyl. In yet another embodiment, $R^{1b}$ is ($C_{1-6}$) alkyl or substituted ($C_{1-6}$) alkyl. In yet another embodiment, $R^{1b}$ is methyl.

In one embodiment, $R^2$ is cyano, —C(=O)H, alkoxycarbonyl, aroxycarbonyl, heterocycloxycarbonyl, acyl, aroyl, heterocycloyl, —C(=$NR^9$)$R^7$, —C(=O)$NR^7R^8$, —C(=S)$NR^7R^8$, —C(=O)N(OMe)Me, or —C(=S)N(OMe)Me. In another embodiment, $R^2$ is cyano, —C(=O)H, alkoxycarbonyl, aroxycarbonyl, heterocycloxycarbonyl, —C(=$NR^9$)$R^7$, —C(=O)$NR^7R^8$, —C(=S)$NR^7R^8$, —C(=O)N(OMe)Me, or —C(=S)N(OMe)Me. In yet another embodiment, $R^2$ is alkoxycarbonyl, aroxycarbonyl, heterocycloxycarbonyl, —C(=O)NR⁷R⁸, —C(=S)NR⁷R⁸, —C(=O)N(OMe)Me, or —C(=S)N(OMe)Me.

In one embodiment, R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy. In another embodiment, R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, (alkoxycarbonyl)oxy, (aroxycarbonyl)oxy, or (heterocycloxycarbonyl)oxy. In another embodiment, R³ is acyloxy, substituted acyloxy, aroyloxy, substituted aroyloxy, heteroaroyloxy, substituted heteroaroyloxy, —OC(=O)—NR⁷R⁸, (alkoxycarbonyl)oxy, (aroxycarbonyl)oxy, or (heterocycloxycarbonyl)oxy. In yet another embodiment, R³ is acyloxy, substituted acyloxy, aroyloxy, substituted aroyloxy, heteroaroyloxy, substituted heteroaroyloxy, or —OC(=O)—NR⁷R⁸.

In one embodiment, R⁴ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, substituted heterocyclyl, (C₁₋₆) alkoxy, aroxy, or heteroaroxy. In another embodiment, R⁴ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl. In yet another embodiment, R⁴ is H, (C₁₋₆) alkyl, substituted (C₁₋₆) alkyl, (C₃₋₆) cycloalkyl, or substituted (C₃₋₆) cycloalkyl.

In one embodiment, R⁶ is H, (C₁₋₆) alkyl, substituted (C₁₋₆) alkyl, (C₃₋₆) cycloalkyl, substituted (C₃₋₆) cycloalkyl, aryl, substituted aryl, heterocyclyl, substituted heterocyclyl, —C(=O)NR⁷R⁸, —SO₂R⁹, —SO₂NR⁷R⁸, —P(=O)(OR⁹)₂, alkoxycarbonyl, aroxycarbonyl, heterocycloxycarbonyl, acyl, aroyl, or heterocycloyl. In another embodiment, R⁶ is H, (C₁₋₆) alkyl, substituted (C₁₋₆) alkyl, (C₃₋₆) cycloalkyl, substituted (C₃₋₆) cycloalkyl, —C(=O)NR⁷R⁸, —SO₂R⁹, —SO₂NR⁷R⁸, —P(=O)(OR⁹)₂, alkoxycarbonyl, aroxycarbonyl, heterocycloxycarbonyl, acyl, aroyl, or heterocycloyl. In yet another embodiment, R⁶ is H, (C₁₋₆) alkyl, substituted (C₁₋₆) alkyl, (C₃₋₆) cycloalkyl, substituted (C₃₋₆) cycloalkyl, —C(=O)NR⁷R⁸, —SO₂R⁹, —SO₂NR⁷R⁸, alkoxycarbonyl, aroxycarbonyl, heterocycloxycarbonyl, acyl, aroyl, or heterocycloyl.

Treatment Methods of the Invention

In one aspect, the invention includes a method of providing anesthesia in a subject in need thereof, comprising administering to the subject a therapeutically effective amount of a pharmaceutical formulation comprising a compound of Formula (I):

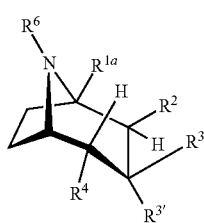

(I)

wherein:

R¹ᵃ is (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, or substituted heterocyclyl;

R² is cyano, —C(=O)H, alkoxycarbonyl, aroxycarbonyl, heterocycloxycarbonyl, acyl, aroyl, heterocycloyl, —C(=NR⁹)R⁷, —C(=O)NR⁷R⁸, —C(=S)NR⁷R⁸, —C(=O)N(OMe)Me, —C(=S)N(OMe)Me, —SO₂R⁹, —SO₂NR⁷R⁸, or —P(=O)(OR⁹)₂;

R³ is acyloxy, substituted acyloxy, aroyloxy, substituted aroyloxy, heteroaroyloxy, substituted heteroaroyloxy, —OC(=O)—NR⁷R⁸, (C₁₋₆) alkoxy, substituted (C₁₋₆) alkoxy, (C₃₋₆) cycloalkoxy, substituted (C₃₋₆) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

R³' is H;

R⁴ is H, (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, substituted heterocyclyl, (C₁₋₆) alkoxy, aroxy, or heteroaroxy;

R⁶ is H, (C₁₋₆) alkyl, substituted (C₁₋₆) alkyl, (C₃₋₆) cycloalkyl, substituted (C₃₋₆) cycloalkyl, (C₂₋₆) alkenyl, substituted (C₂₋₆) alkenyl, (C₂₋₆) alkynyl, substituted (C₂₋₆) alkynyl, aryl, substituted aryl, heterocyclyl, substituted heterocyclyl, —C(=O)NR⁷R⁸, —SO₂R⁹, —SO₂NR⁷R⁸, —P(=O)(OR⁹)₂, alkoxycarbonyl, aroxycarbonyl, heterocycloxycarbonyl, acyl, aroyl, or heterocycloyl;

R⁷ and R⁸ are independently H, (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl; and, each occurrence of R⁹ is independently (C₁₋₆) alkyl, substituted (C₁₋₆) alkyl, (C₃₋₆) cycloalkyl, substituted (C₃₋₆) cycloalkyl, aryl, substituted aryl, heterocyclyl, or substituted heterocyclyl;

or a salt thereof.

In one embodiment, the pharmaceutical formulation is administered to the subject by parenteral, topical, oral or intranasal route. In embodiments, the compound of Formula (I) is methyl (1R,2R,3S,5S)-(−)-3-(benzoyloxy)-1,8-dimethyl-8-azabicyclo[3.2.1]octane-2-carboxylate, methyl (1R,2R,3S,5S)-(−)-1-propyl-3-(benzoyloxy)-8-methyl-8-azabicyclo[3.2.1]octane-2-carboxylate, methyl (1R,2R,3S,5S)-(−)-1-ethyl-3-(benzoyloxy)-8-methyl-8-azabicyclo[3.2.1]octane-2-carboxylate, methyl (1R,2R,3S,5S)-(+)-1-pentyl-3-(benzoyloxy)-8-methyl-8-azabicyclo[3.2.1]octane-2-carboxylate, methyl (1R,2R,3S,5S)-(−)-3-(benzoyloxy)-1-phenyl-8-methyl-8-azabicyclo[3.2.1]octane-2-carboxylate, or a salt thereof. In yet another embodiment, the subject is human.

In another aspect, the invention provides a method of blocking uptake of a monoamine neurotransmitter in a subject in need thereof, wherein the neurotransmitter is selected from the group consisting of serotonin, norepinephrine and dopamine, wherein the method comprises administering to the subject a therapeutically effective amount of a pharmaceutical formulation comprising a compound of Formula (I):

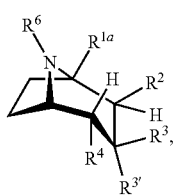

(I)

wherein:

R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, or substituted heterocyclyl;

R$^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;

R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

R$^{3'}$ is H;

R$^4$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, (C$_{1-6}$) alkoxy, aroxy, or heteroaroxy;

R$^6$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

R$^7$ and R$^8$ are independently H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl; and, each occurrence of R$^9$ is independently (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;

or a salt thereof.

In one embodiment, the neurotransmitter is serotonin. In another embodiment, the neurotransmitter is norepinephrine. In yet another embodiment, the neurotransmitter is dopamine. In yet another embodiment, the pharmaceutical formulation is administered to the subject by parenteral, topical, oral or intranasal route. In yet another embodiment, the compound of Formula (I) is methyl (1R,2R,3S,5S)-(+)-3-(benzoyloxy)-1,8-dimethyl-8-azabicyclo[3.2.I]octane-2-carboxylate, methyl (1R,2R,3S,5S)-(−)-1-propyl-3-(benzoyloxy)-8-methyl-8-azabicyclo [3.2.1]octane-2-carboxylate, methyl (1R, 2R,3S,5S)-(−)-1-ethyl-3-(benzoyloxy)-8-methyl-8-azabicyclo[3.2.1]octane-2-carboxylate, methyl (1R,2R,3S,5S)-(+)-1-pentyl-3-(benzoyloxy)-8-methyl-8-azabicyclo[3.2.1] octane-2-carboxylate, methyl (1R,2R,3S,5S)-(−) -3-(benzoyloxy)-1-phenyl-8-methyl-8-azabicyclo[3.2.1] octane-2-carboxylate, or a salt thereof. In yet another embodiment, the subject is human.

The invention is also directed to a method of treating depression in a subject in need thereof. The method comprises administering to the subject a therapeutically effective amount of a pharmaceutically formulation comprising a compound of Formula (I), as indicated above. In yet another embodiment, the compound of Formula (I) is methyl (1R,2R, 3S,5S)-(−)-3-(benzoyloxy)-1,8-dimethyl-8-azabicyclo[3.2.I] octane-2-carboxylate, or a salt thereof. In yet another embodiment, the subject is human. In yet another embodiment, the pharmaceutical formulation for treatment of depression is administered to the subject by parenteral, topical, oral or intranasal route. In yet another embodiment, the compound of Formula (I) is methyl (1R,2R,3S,5S)-(−)-3-(benzoyloxy)-1,8-dimethyl-8-azabicyclo[3.2.I]octane-2-carboxylate, methyl (1R,2R,3S,5S)-(−)-1-propyl-3-(benzoyloxy)-8-methyl-8-azabicyclo[3.2.1]octane-2-carboxylate, methyl (1R,2R,3S, 5S)-(−)-1-ethyl-3-(benzoyloxy)-8-methyl-8-azabicyclo[3.2.1]octane-2-carboxylate, methyl (1R, 2R,3S,5S)-(−)-1-pentyl-3-(benzoyloxy)-8-methyl-8-azabicyclo [3.2.1]octane-2-carboxylate, methyl (1R,2R,3S,5S)-(−)-3-(benzoyloxy)-1-phenyl-8-methyl-8-azabicyclo[3.2.1 [octane-2-carboxylate, or a salt thereof. In yet another embodiment, the subject is human.

Administration of the Compounds of the Invention

The compound of the invention may be administered in the form of a pharmaceutical composition, in combination with a pharmaceutically acceptable carrier. The active ingredient in such formulations may comprise from 0.1 to 99.99 weight percent.

The compound of the invention is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18$^{th}$ Edition (1990), Mack Publishing Co., Easton, Pa. Suitable dosage forms may comprise, for example, tablets, capsules, solutions, parenteral solutions, troches, suppositories, or suspensions.

The compositions are preferably formulated in a unit dosage form, each dosage containing from about 1 mg to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

Parenteral Administration:

Parenteral administration includes, for example, intraperitioneal, intravenous, intramuscular, intra-arterial, intravesical (e.g., to the bladder), intrathecal, intradermal, or subcutaneous administration.

For parenteral administration, the compounds of the invention may be formulated for injection or infusion, for example, intravenous, intramuscular or subcutaneous injection or infusion, or for administration in a bolus dose and/or continuous infusion.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non aqueous solution, dispersion, suspension or emulsion, optionally containing other formulatory agents such as suspending, stabilizing and/or dispersing agents.

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication may then be administered directly to cells in the spinal cord.

The term "intravesical administration" is used herein in its conventional sense to mean delivery of a drug directly into the bladder. Suitable methods for intravesical administration can be found, for example, in U.S. Pat. Nos. 6,207,180 and 6,039,967.

Oral Administration:

For oral administration, the active agent may be combined with one or more solid inactive ingredients for the preparation of tablets, capsules, pills, powders, granules or other suitable oral dosage forms. For example, the active agent may be combined with at least one excipient, such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

Intranasal/Inhalation Administration:

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents that may be used instead of propylene glycol include glycerol and polyethylene glycol.

Capsules, blisters and cartridges (made, for example, from gelatin or HPMC) for use in an inhaler or insufflator may be formulated to contain a powder mix of the compound of Formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release may be obtained by using for example poly(D,L-lactic-co-glycolic acid).

Topical Administration:

Topical administration comprises administering a compound of the invention to a body surface, such as, but not limited to, the skin or a mucous membrane. Non-limiting examples of mucous membranes contemplated within the invention are the membranes in the throat, eyes, ears, vagina, and anus.

Topical formulations may be in any form suitable for application to the body surface, and may comprise, for example, an ointment, cream, gel, lotion, solution, paste or the like, and/or may be prepared so as to contain liposomes, micelles, and/or microspheres.

Formulations suitable for topical administration include, but are not limited to, liquid or semi liquid preparations such as liniments, lotions, oil-in-water or water-in-oil emulsions, such as creams, ointments or pastes, and solutions or suspensions. In certain embodiments, topical formulations herein are ointments, creams and gels.

As non-limiting examples, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, a non-aerosol liquid formulation, or a dry powder, placed within or near the rectum ("transrectal" formulations), or administered to the urethra as a suppository, ointment, or the like.

Topical administration may also involve the use of transdermal administration such as transdermal patches or iontophoresis devices. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Other components may be incorporated into the transdermal patches as well. For example, compositions and/or transdermal patches may be formulated with one or more preservatives or bacteriostatic agents including, but not limited to, methyl hydroxyl-benzoate, propyl hydroxy-benzoate, chlorocresol, benzalkonium chloride, and the like. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

In the dosage form contemplated within the invention, the compositions of the invention may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water ands orbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citricacid, propylene glycol). Woven pads orrolls of bandaging material, e.g., gauze, may be impregnated with the compositions in solution, lotion, cream, ointment or other such form may also be used for topical application. The compositions may also be applied topically using a transdermal system, as described above.

With respect to the ophthalmic administration of the compounds of the invention, a pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmologically-administrable formulations that are useful include those which comprise the active ingredient in microcrystalline form or in a liposomal preparation.

With respect to the intravesical administration (i.e., delivery of a drug directly into the bladder) of the compounds of the invention, suitable methods for intravesical administration can be found, for example, in U.S. Pat. Nos. 6,207,180 and 6,039,967.

With regard to transurethal administration of the compounds of the invention, the formulation may comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials. A transurethral permeation enhancer may be included in the dosage from. Examples of suitable permeation enhancers include dimethylsulfoxide ("DMSO"), dimethylformamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecyl-cyclazacycloheptan-2-one (available under the trademark Azone™ from Nelson Research & Development Co., Irvine, Calif.), SEPA™ (available from Macrochem Co., Lexington, Mass.), surfactants as discussed above, including, for example, Tergitol™, Nonoxynol-9™ and TWEEN-80™, and lower alkanols such as ethanol.

With respect to the transrectal administration of the compounds of the invention, dosage forms may include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention may be manufactured using conventional processes. The transrectal dosage unit may be fabricated to disintegrate rapidly or over a period of several hours. The time period for complete disintegration may be in the range of from about 10 minutes to about 6 hours, e.g., less than about 3 hours.

With respect to the vaginal or perivaginal administration of the compounds of the invention, dosage forms may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Controlled Release Formulations

The pharmaceutical compositions of the present invention may also be formulated so as to provide slow or controlled release of the active ingredient therein, using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

In accordance with the present invention, as described above or as discussed in the Examples below, there may be employed conventional chemical and biochemical techniques that are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is described hereafter with reference to the following examples. The examples are provided for the purpose of illustration only and the invention should in no way be construed as being limited to these examples, but rather should be construed to encompass any and all variations that become evident as a result of the teaching provided herein.

Materials & Methods

All reagents were used as received unless otherwise noted. Tetrahydrofuran (THF), diethyl ether (Et$_2$O), dichloromethane (DCM), and toluene were purified by filtration on a Glass Contour Seca solvent purification system. Unless otherwise mentioned, all reactions were carried under argon atmosphere. Column chromatography was performed on silica gel, Merck grade 60 (230-400 mesh). Thin layer chromatography (TLC) plates were visualized with UV, in an iodine chamber, or with phosphomolybdic acid, unless otherwise noted. $^1$H NMR and $^{13}$C NMR spectra were recorded on a Bruker 500, a Bruker 400 and Varian 300 MHz NMR spectrometers.

Preparative Example A (S)-(+)-3-(2-methyl-1,3-dioxolan-2-yl)-propylidene-p-toluenesulfmamide (2)

was prepared as previously described (Davis et al., 2009, Org. Lett. 11:1647-1650).

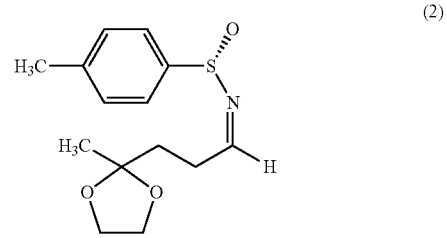

(2)

Preparative Example B (S)-(+)-3-(2-Propyl-1,3-dioxalan-2-yl)propylidene-p-toluenesulfinamide (2b)

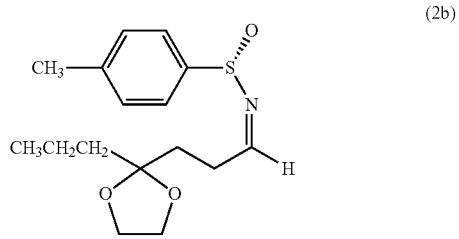

(2b)

To a 500 mL round-bottomed flask equipped with magnetic stirring bar and argon inlet was placed 4,4-ethylenedioxy-4-propylbutanol (2.22 g, 12.88 mmol) in dry CH$_2$Cl$_2$ (100 mL). (S)-(+)-p-Toluenesulfinamide (1.99 g, 12.88 mmol) was added followed by Ti(OEt)$_4$ (14.71 g, 64.45 mmol) and the reaction was stirred at room temperature ("rt") for 48 hours. At this time, the reaction mixture was cooled to 0° C. and then quenched with H$_2$O (6 mL). After stirring for 5 min., the solids were filtered, the filter cake was washed with DCM (3×50 mL), the combined organic phases was washed with brine (100 mL), dried (MgSO$_4$), and concentrated. Flash chromatography (25% EtOAc/hexanes) gave 2.79 g (70%) of slightly yellow oil; IR (film) 1625 cm$^{-1}$; $[\alpha]_D^{20}$+230.17; (c 0.6, CHCl$_3$); $^1$H NMR (CDCl$_3$) δ 0.89 (t, J=7.3 Hz, 3H), 1.36 (m, 2H), 1.55 (m, 2H), 1.96 (m, 2H), 2.39 (s, 3H), 2.55 (m, 2H), 3.86 (m, 4H), 7.29 (bd, J=7.8 Hz, 2H), 7.56 (bd, J=8.1 Hz, 2H), 8.23 (t, J=4.4 Hz, 1H); $^{13}$C NMR (CDCl$_3$) δ 14.3, 17.1, 30.5, 32.5, 39.7, 64.9, 65.0, 110.8, 124.6, 129.7, 141.6, 141.8, 167.3; HRMS calcd for C$_{16}$H$_{24}$NO$_3$S (M+H) 310.1477. Found 310.1473.159.

Preparative Example C (S)-(+)-3-(2-ethyl-1,3-dioxolan-2-yl)propylidene-(tert)butylsulfinamide (2c)

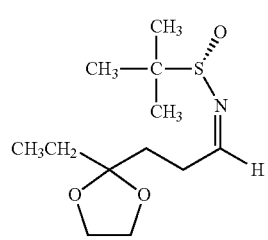

(2c)

In a 250 mL, oven dried, single-necked round bottom flask equipped with a magnetic stirring bar, rubber septum, and argon inlet, was placed 4,4-ethylenedioxy-4-ethylbutanal (1.2 g, 7.59 mmol) in tetrahydrofuran (THF) (76 mL) and (S)-(+)-tert-butylsulfinamide (0.919 g, 7.59 mmol) and Ti(OEt)$_4$ (5.19 g, 22.78 mmol) were added. The reaction mixture was stirred at rt for 24 hours, cooled to 0° C., and quenched by addition of brine solution (75 mL). The solution was filtered through Celite, the filter cake was washed with EtOAc (2×75 mL), the combined organic phases were washed with brine (1×75 mL), dried (MgSO$_4$), and concentrated. Flash chromatography (25% EtOAc/hexanes) gave 1.58 g (80%) of a colorless oil; $[\alpha]^{20}_D$+163.35° (c 2.085, CHCl$_3$); IR (neat) 1623 cm$^{-1}$; $^1$H NMR (CDCl$_3$)™ 0.917 (t, J=7.6 Hz, 3H), 1.18 (s, 9H), 1.64 (m, 3H), 1.97 (m, 2H), 2.57 (m, 2H), 3.94 (s, 4H), 8.08 (t, J=4.4 Hz, 1H); $^{13}$C NMR (CDCl$_3$) δ 8.0, 22.1, 30.0, 30.5, 31.9, 56.3, 64.9, 65.0, 111.0, 169.3. HRMS calcd for C$_{12}$H$_{24}$NO$_3$S (M+H) 262.1477. Found 262.1477.

Preparative Example D (S)-(+)-3-(2-pentyl-1,3-dioxolan-2-yl)propylidene-(terabutylsulfinamide (2d)

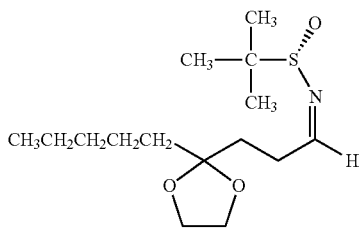

(2d)

The title compound was prepared in manner analogous to the method of Preparative Example C. Flash chromatography (25% EtOAc/hexanes) gave 1.59 g (70%) of a colorless oil; $[\alpha]^{20}_D$+156.6 (c 3.56, CHCl$_3$); IR(neat) 1623 cm$^{-1}$; $^1$H NMR (CDCl$_3$) δ 0.88 (t, J=7.1 Hz, 3H), 1.18 (s, 9H), 1.31 (m, 6H), 1.59 (m, 2H), 1.98 (m, 2H), 2.57 (m, 2H), 3.94 (m, 4H), 8.08 (t, J=4.4 Hz, 1H); $^{13}$C NMR (CDCl$_3$) δ 13.9, 22.2, 22.4, 23.4, 30.6, 31.9, 32.4, 37.2, 56.4, 64.8, 64.9, 110.8, 169.3; HRMS calcd for C$_{15}$H$_{30}$NO$_3$S (M+H) 304.1946. Found 304.1945.

Preparative Example E (S)-(+)-3-(2-Phenyl-1,3-dioxalan-2-yl)propylidene-(tert)butylsulfinamide (2e)

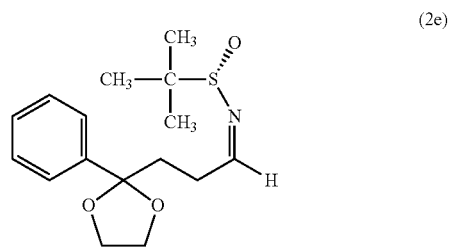

(2e)

(S)-(+)-3-(2-Phenyl-1,3-dioxalan-2-yl)propylidene-t-butylsulfinamide (2e) was prepared was prepared in manner analogous to the method of Preparative Example C. Flash chromatography (40% EtOAc/hexanes) gave 4.0 g (80%) of a white solid mp 60-61° C.; $[\alpha]^{20}_D$+155.49 (c 0.55, CHCl$_3$); $^1$H NMR (CDCl$_3$) δ 1.17 (s, 3H), 2.24 (m, 2H), 2.60 (m, 2H), 3.78 (m, 2H), 4.02 (m, 2H), 7.35 (m, 3H), 7.45 (m, 2H), 8.08 (t, J=4.4 Hz, 1H); $^{13}$C NMR (CDCl$_3$) δ 22.3, 30.7, 35.9, 56.5, 64.5, 64.6, 109.6, 125.6, 128.1, 128.2, 142.1, 169.2. HRMS calcd for C$_{16}$H$_{24}$NO$_3$S (M+H) 310.1477. Found 310.1477.

Preparative Example 1

(S$_S$,3S)-(+)-Methyl N-(p-toluenesulfinyl)-3-amino-5-(2-methyl-1,3-dioxolan-2-yl)-pentanoate

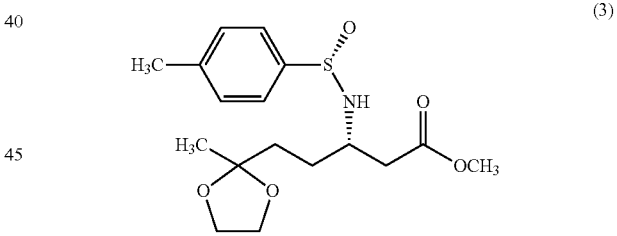

(3)

To a 500 mL round-bottomed flask equipped with magnetic stirring bar and argon inlet was placed NaHMDS (53.63 mL, 53.63 mmol, 1.0 M solution in THF) in anhydrous ether (300 mL). To this solution methyl acetate (3.61 g, 48.75 mmol) was added drop wise at −78° C. slowly via syringe and the reaction mixture was stirred at this temperature for 1 h. At this time (2) (5.48 g, 19.50 mmol) in THF (20 mL) was added to above solution slowly via cannula. After stirring for 2 hours at −78° C., the reaction mixture was quenched by adding sat. NH$_4$Cl solution (30 mL) and H$_2$O (100 mL) was added. The phases were separated and the aqueous phase was extracted with EtOAc (3×100 mL). The combined organic phases were washed with brine (100 mL), dried (MgSO$_4$) and concentrated. Flash chromatography (hexanes:EtOAc, 50:50) gave 6.92 g (75%) of a clear oil (dr>99:1); IR (film) 3230, 1740, cm$^{-1}$; $[\alpha]_D^{20}$+80.40; (c 1.49, CHCl$_3$); $^1$H NMR (CDCl$_3$) δ 1.32 (s, 3H), 1.73 (m, 3H), 1.87 (m, 1H), 2.40 (s, 3H), 2.60 (dq, J=5.4 Hz, J=16.4 Hz, 2H), 3.65 (s, 3H), 3.68 (m, 1H), 3.94 (m, 4H), 4.62 (d, J=8.8 Hz, 1H), 7.28 (bd, J=8.4 Hz, 2H), 7.57 (td, J=1.6 Hz, J=8.0 Hz, 2H); $^{13}$C NMR (CDCl$_3$) 21.3, 23.9, 30.0, 35.4, 40.5, 51.7, 52.6, 64.6, 64.7, 109.7, 125.4, 129.5, 41.3, 142.4, 171.9; HRMS calcd for C$_{17}$H$_{25}$NNaO$_5$S (M+Na) 378.1351. Found 378.1333.

Alternate Preparative Example 1

(S$_S$,3S)-(+)-Methyl N-(p-toluenesulfinyl)-3-amino-5-(2-methyl-1,3-dioxolan-2-yl)-pentanoate (3)

The procedure of Preparative Example 1 was followed, substituting NaCl for NH$_4$Cl. Flash chromatography (hexanes:EtOAc, 50:50) gave 4.16 g (60%) of a clear oil (dr>99:1).
[α]$_d^{25}$+80.40 (c 1.49, CHCl$_3$). $^1$H NMR (CDCl$_3$) δ 1.32 (s, 3H), 1.73 (m, 3H), 1.87 (m, 1H), 2.40 (s, 3H), 2.60 (dq, J=5.4 Hz, J=16.4 Hz, 2H), 3.65 (s, 3H), 3.68 (m, 1H), 3.94 (m, 4H), 4.62 (d, J=8.8 Hz, 1H), 7.28 (bd, J=8.4 Hz, 2H), 7.57 (td, J=1.6 Hz, J=8.0 Hz, 2H). $^{13}$C NMR (CDCl$_3$) δ 21.3, 23.9, 30.0, 35.4, 40.5, 51.7, 52.6, 64.6, 64.7, 109.7, 125.4, 129.5, 141.3, 142.4, 171.9. HRMS calcd for C$_{17}$H$_{25}$NNaO$_5$S (M+Na) 378.1351. Found 378.1333.

Preparative Example 1a (S$_S$,3S)-(+)-Methyl-N-(p-toluenesulfinyl)-3-amino-5-(2-propyl-1,3-dioxolan-2-yl)-pentanoate (3a)

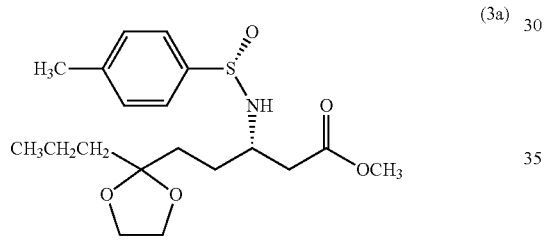

(3a)

The title compound was prepared in a manner analogous to the method of Preparative Example 1. Colorless oil; IR (film) 3226, 1736, cm$^{-1}$; [α]$_D^{20}$+66.77 (c 0.9, CHCl$_3$); $^1$H NMR (CDCl$_3$) δ 0.91 (t, J=7.3 Hz, 3H), 1.38 (m, 2H), 1.58 (m, 2H), 1.69 (m, 3H), 1.83 (m, 1H), 2.40 (s, 3H), 2.60 (dq, J=16.6 Hz, J=5.6 Hz, 2H), 3.65 (s, 3H), 3.68 (m, 1H), 3.92 (bs, 4H), 4.61 (d, J=9.0 Hz, 1H), 7.28 (bd, J=8.1 Hz, 2H), 7.58 (td, J=8.1 Hz, J=1.7 Hz, 2H); $^{13}$C NMR (CDCl$_3$) δ 14.3, 17.1, 21.3, 29.8, 33.3, 39.4, 40.5, 51.6, 52.7, 64.9 (2C), 111.4, 125.4, 129.5, 141.3, 142.4, 171.9; HRMS calcd for C$_{19}$H$_{29}$NNaO$_5$S (M+Na) 406.1664. Found 406.1665.

Preparative Example 1b (S$_S$,S)-(+)-Methyl-N-(tert-butylsulfinyl)-3-amino-5-(2-ethyl-1,3-dioxolan-2-yl)-pentanoate (3b)

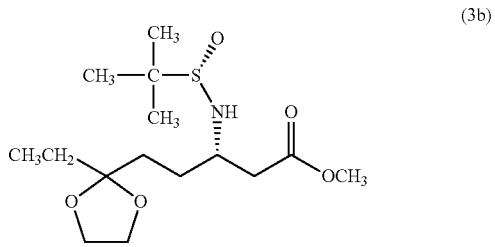

(3b)

In a 500 mL, oven dried, single-necked round-bottom flask equipped with magnetic stirring bar, rubber septum, and argon inlet, was placed sodium bis(trimethylsilyl)amine (NaHMDS) (1.0 M solution in THF, 18.1 mL, 18.16 mmol) in Et$_2$O (242 mL). The solution was cooled to −78° C. and methyl acetate (1.34 g, 18.16 mmol) was slowly added via syringe. After stirring for 1 h, a solution of (S)-(+)-3-(2-ethyl-1,3-dioxalan-2-yl)propylidene-(tert)butylsulfinamide (1.58 g, 6.05 mmol) in THF (7 mL) was added via cannula and the reaction mixture was stirred for 3 hours at −78° C. At this time the reaction mixture was quenched by the addition of sat. NH$_4$Cl solution (50 mL), extracted with EtOAc (3×30 mL), dried (MgSO$_4$), and concentrated. Flash chromatography (80% EtOAc/hexanes) gave 1.84 g (91%) of a colorless oil; [α]$^{20}_D$ (+) 29.22 (c 1.60, CHCl$_3$); IR(neat) 1741 cm$^{-1}$; $^1$H NMR (CDCl$_3$) δ 0.88 (t, J=7.6 Hz, 3H), 1.21 (s, 9H), 1.58 (s, 4H0, 1.62 (t, J=7.6 Hz, 4H), 1.79 (m, 1H), 2.62 (dd, J=16.1, 5.4 Hz, 1H), 2.79 (dd, J=16.1, 5.4 Hz, 1H), 3.53 (b, 1H), 3.68 (s, 3H), 3.92 (s, 4H), 4.17 (d, J=8.6 Hz, 1H); $^{13}$C NMR (CDCl$_3$) δ 8.0, 22.6, 29.7, 32.8, 40.3, 51.6, 54.0, 55.8, 64.8, 64.9, 111.6, 172.2. HRMS calcd for C$_{15}$H$_{30}$NO$_5$S (M+H) 336.1845. Found 336.1837.

Preparative Example 1c (S$_S$,S)-(+)-Methyl-N-(tert-butylsulfinyl)-3-amino-5-(2-pentyl-1,3-dioxolan-2-yl)-pentanoate (3c)

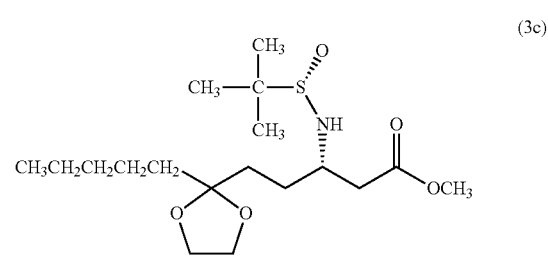

(3c)

The title compound was prepared in manner analogous to the method of Preparative Example 1b. Flash chromatography (70% EtOAc/hexanes) gave 1.75 g (91%) of a colorless oil; [α]$^{20}_D$+34.83 (c 1.375, CHCl$_3$); IR(neat) 1741 cm'$^1$; $^1$H NMR (CDCl$_3$) δ 0.88 (t, J=7.2 Hz, 3H), 1.21 (s, 9H), 1.27 (m, 6H), 1.59 (m, 8H), 1.76 (m, 1H), 2.61 (dd, J=16.1, 5.4 Hz, 1H), 2.79 (dd, J=16.1, 5.4 Hz, 1H), 3.53 (b, 1H), 3.68 (s, 3H), 3.92 (m, 4H), 4.18 (d, J=8.6 Hz, 1H); $^{13}$C NMR (CDCl$_3$) δ 13.9. 22.5, 22.6, 23.4, 29.8, 31.9, 33.2, 37.0, 40.3, 51.6, 54.0, 55.8, 64.8 (2C's), 111.4, 172.2. HRMS calcd for C$_{15}$H$_{36}$NO$_5$S (M+H) 378.2314. Found 378.2314.

Preparative Example 1d (S$_S$,3S)-(+)-Methyl N-(tert-butylsulfinyl)-3-amino-5-(2-phenyl-1,3-dioxolan-2-yl)pentanoate (3d)

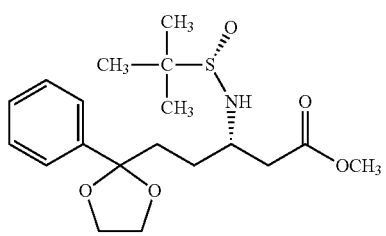

(3d)

The title compound was prepared in manner analogous to the method of Preparative Example 1b. Flash chromatography (hexanes:EtOAc, 50:50) gave 0.60 g (93%) of a clear oil (dr>99:1); $[\alpha]^{20}{}_D$+31.27 (c 2.35, CHCl$_3$); $^1$H NMR (CDCl$_3$) δ 1.19 (s, 9H), 1.62 (m, 2H), 1.94 (m, 1H), 2.03 (m, 1H), 2.65 (dd, J=16.1 Hz, J=5.4 Hz, 2H), 3.55 (m, 1H), 3.65 (s, 3H), 3.75 (m, 2H), 4.00 (m, 2H), 4.09 (d, J=8.8 Hz, 1H), 7.32 (m, 3H), 7.41 (m, 2H); $^{13}$C NMR (CDCl$_3$) δ 22.5, 29.4, 36.5, 40.2, 51.5, 53.7, 55.7, 64.3, 64.4, 109.9, 125.4, 127.7, 128.0, 142.2, 172.1. HRMS calcd for C$_{19}$H$_{30}$NO$_5$S 384.1845. Found 384.1842.

Preparative Example 2

(S$_S$,3S)-(+)-N-(p-Toluenesulfinyl)-3-amino-5-(2-methyl-1,3-dioxolan-2-yl)pentanal (4)

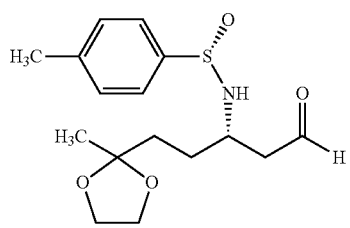

(4)

In a 250 mL, oven-dried, single-neck round-bottomed flask equipped with magnetic stirring bar, and a rubber septum was placed (3) (2.64 g, 7.42 mmol) in toluene (75 mL). The solution was cooled to −78° C. and diisobutylaluminumhydride (13.36 mL, 13.36 mmol, 1.0 M solution in toluene) was added slowly via syringe. After being stirred for 1 h, the reaction mixture was quenched with saturated aqueous NH$_4$Cl (15 mL) at −78° C. and warmed to rt. The reaction mixture was diluted with EtOAc (50 mL) and water (40 mL). This mixture was filtered through a Celite pad and the aqueous phase was extracted with EtOAc (3×60 mL). The combined organic phases were washed with brine (100 mL), dried (MgSO$_4$) and concentrated. Chromatography (80% EtOAc/hexanes) afforded 2.3 g (95%) of clear oil; IR (film) 3424, 1725 cm$^{-1}$; $[\alpha]^{20}{}_D$+78.34 (c 1.68, CHCl$_3$); $^1$H NMR (CDCl$_3$) δ 1.31 (s, 3H), 1.75 (m, 4H), 2.39 (s, 3H), 2.68 (m, 1H), 3.76 (m, 1H), 3.93 (m, 4H), 4.43 (d, J=8.8 Hz, 1H), 7.27 (bd, J=8.0 Hz, 2H), 7.54 (td, J=2.0 Hz, J=8.0 Hz, 2H), 9.61 (t, J=1.2 Hz, 1H); $^{13}$C NMR (CDCl$_3$) δ 21.3, 23.8, 30.5, 35.4, 49.9, 50.6, 64.6, 64.7, 109.6, 125.4, 129.5, 141.5, 141.9, 200.7; HRMS calcd for C$_{16}$H$_{24}$NO$_4$S (M+H) 326.1421. Found 326.1424.

Alternate Preparative Example 2

(S$_S$,3S)-(+)-N-(p-Toluenesulfinyl)-3-amino-5-(2-methyl-1,3-dioxolan-2-yl)pentanal (4)

The procedure of Preparative Example 2 was followed, using NH$_4$Cl to quench the reaction mixture. Chromatography (80% EtOAc-hexanes) afforded 2.2 g (91%) of clear oil. $[\alpha]^{20}{}_D$+78.34 (c 1.68, CHCl$_3$). $^1$H NMR (CDCl$_3$) δ 1.31 (s, 3H), 1.75 (m, 4H), 2.39 (s, 3H), 2.68 (m, 1H), 3.76 (m, 1H), 3.93 (m, 4H), 4.43 (d, J=8.8 Hz, 1H), 7.27 (bd, J=8.0 Hz, 2H), 7.54 (td, J=2.0 Hz, J=8.0 Hz, 2H), 9.61 (t, J=1.2 Hz, 1H). $^{13}$C NMR (CDCl$_3$) δ 21.3, 23.8, 30.5, 35.4, 49.9, 50.6, 64.6, 64.7, 109.6, 125.4, 129.5, 141.5, 141.9, 200.7. HRMS calcd for C$_{16}$H$_{24}$NO$_4$S (M+H) 326.1421. Found 326.1424.

Preparative Example 2a (S$_S$,3S)-(+)-N-(p-Toluenesulfinyl)-3-amino-5-(2-propyl-1,3-dioxolan-2-yl)pentanal (4a)

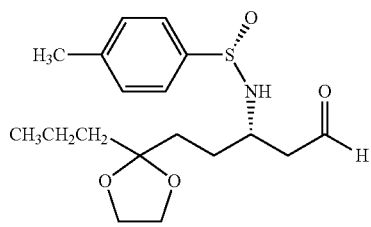

(4a)

The title compound was prepared in manner analogous to the method of Preparative Example 2. Colorless oil; IR (film) 3440, 1721 cm'; $[\alpha]^{20}{}_D$+73.67 (c 1.56, CHCl$_3$); $^1$H NMR (CDCl$_3$) δ 0.91 (t, J=7.3 Hz, 3H), 1.37 (m, 2H), 1.57 (m, 2H), 1.69 (m, 3H), 1.83 (m, 1H), 2.40 (s, 3H), 2.67 (m, 2H), 3.75 (m, 1H), 3.92 (bs, 4H), 4.41 (d, J=8.8 Hz, 1H), 7.28 (bd, J=7.8 Hz, 2H), 7.55 (td, J=8.1 Hz, J=1.7 Hz, 2H); $^{13}$C NMR (CDCl$_3$) δ 14.3, 17.1, 21.3, 30.3, 33.2, 39.4, 49.9, 50.7, 64.9 (2C), 111.3, 125.4, 129.5, 141.4, 142.0, 200.7; HRMS calcd for C$_{18}$H$_{27}$NNaO$_4$S (M+Na) 376.1558. Found 376.1557.

Preparative Example 2b (S$_S$,S)-(+)-N-(tert-butylsulfinyl)-3-amino-5-(2-ethyl-1,3-dioxolan-2yl)pentanal (4b)

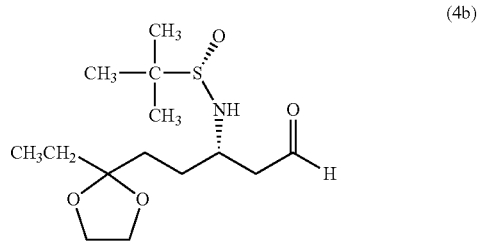

(4b)

In a 100 mL, oven dried, single necked round-bottom flask equipped with magnetic stirring bar and rubber septum was placed ($S_S$,3S)-(+)-methyl-N-(tert-butylsulfinyl)-3-amino-5-(2-ethyl)-1,3-dioxalan-2-yl)-pentanoate (1.84 g, 5.49 mmol) in toluene (55 mL) and the solution was cooled to −78° C. Diisobutylaluminum hydride (DIBAL-H) in toluene (1.0 M solution in toluene, 9.9 mL, 9.88 mmol) was added slowly via syringe, the solution was stirred for 20 min at −78° C., and quenched by the addition of sat. $NH_4Cl$ (30 mL). The solution was extracted with EtOAc (3×30 mL), dried ($MgSO_4$), and concentrated. Flash chromatography (90% EtOAc/hexanes) provided 1.25 g (75%) of colorless oil; $[\alpha]^{20}_D$+35.479 (c 1.46, $CHCl_3$); IR (film) 3435, 1723 $cm^{-1}$; $^1H$ NMR ($CDCl_3$) δ 0.89 (t, J=7.6 Hz, 3H), 1.20 (s, 9H), 1.71 (b, 8H), 2.89 (d, J=5.6 Hz, 2H), 3.62 (b, 1H), 3.75 (d, J=8.8 Hz, 1H), 3.93 (s, 1H), 9.78 (s, 1H); $^{13}C$ NMR ($CDCl_3$) δ 8.0, 22.5, 22.7, 30.0, 32.7, 49.8, 52.8, 55.8, 64.8 (2C's), 111.5, 200.9; HRMS calcd for $C_{14}H_{28}NO_4S$ (M+H) 306.1739. Found 306.1737.

Preparative Example 2c ($S_S$,S)-(+)-N-(tert-butylsulfinyl)-3-amino-5-(2-pentyl-1,3-dioxolan-2yl)pentanal (4c)

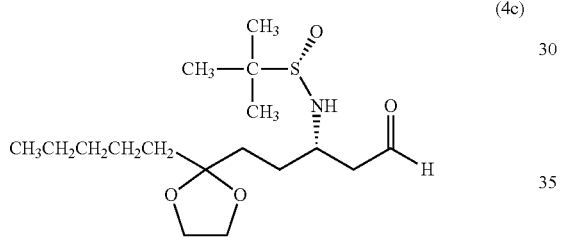

(4c)

The title compound was prepared in manner analogous to the method of Preparative Example 2b. Flash chromatography (90% EtOAc/hexanes) provided 1.15 g (72%) of colorless oil; $[\alpha]^{20}_D$+32.462 (c 1.64, $CHCl_3$); IR (film) 3435, 1723 $cm^{-1}$; $^1H$ NMR ($CDCl_3$) δ 0.88 (t, J=7.1 Hz, 3H), 1.20 (s, 9H), 1.28 (m, 6H), 1.57 (b, 8H), 1.72 (m, 4H), 2.89 (d, J=5.6 Hz, 2H), 3.62 (b, 1H), 3.75 (d, J=8.4 Hz, 1H), 3.92 (m, 4H), 9.78 (s, 1H); $^{13}C$ NMR ($CDCl_3$) δ 13.9. 22.6, 23.5, 30.1, 32.0, 33.3, 37.1, 50.0, 53.0, 56.0, 64.8, 64.9, 111.4, 201.0; HRMS calcd for $C_{17}H_{34}NO_4S$ (M+H) 348.2209. Found 348.2208.

Preparative Example 2d ($S_S$,3S)-(+)-N-(t-Butylsulfinyl)-3-amino-5-(2-phenyl-1,3-dioxolan-2-yl)pentanal (4d)

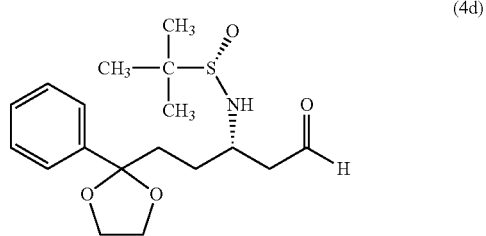

(4d)

The title compound was prepared in manner analogous to the method of Preparative Example 2b. Chromatography (80% EtOAc/hexanes) afforded 3.55 g (85%) of clear oil; $[\alpha]^{20}_D$+32.45 (c 1.77, $CHCl_3$); $^1H$ NMR ($CDCl_3$) δ 1.18 (s, 9H), 1.66 (m, 1H), 1.93 (m, 1H), 2.06 (m, 1H), 2.83 (dd, J=5.4, J=1.0 Hz, 2H), 3.63 (m, 1H), 3.68 (d, J=8.4 Hz, 1H), 3.76 (m, 2H), 3.99 (m, 2H), 7.33 (m, 3H), 7.41 (m, 2H); $^{13}C$ NMR ($CDCl_3$) 22.6, 29.9, 36.7, 49.9, 52.7, 55.9, 64.4, 64.5, 109.9, 125.5, 127.9, 128.1, 142.2, 200.9. This compound decomposed and a satisfactory high resolution mass spectrograph could not be obtained.

Preparative Example 3

($S_S$,5S,2E)-(+)-Methyl-N-(p-toluenesulfinyl)-5-amino-7-(2-methyl-1,3-dioxolan-2-yl)hept-2-enoate (5)

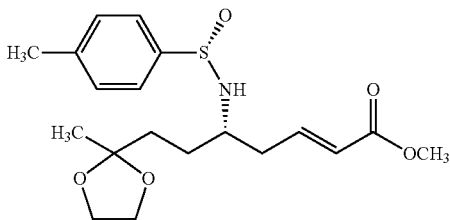

(5)

In a 50 mL, oven-dried, single-neck round-bottomed flask equipped with magnetic stirring bar, and a rubber septum was placed trimethylphosphonoacetate (2.11 g, 11.60 mmol) in anhydrous acetonitrile (20 mL) under argon. To this solution 1,8-diazabicyclo[5.4.0]undec-7-ene (DBU) (1.76 g, 11.60 mmol) was added at room temperature and stirred for 15 minutes. At this time, a solution of (4) (1.89 g, 5.80 mmol) in dry acetonitrile (20 mL) was added to the above reaction mixture via cannula and monitored for completion by checking TLC (typically 2 hours). At this time the reaction mixture was quenched by addition of water (80 mL), the phases were separated, and the aqueous phase was extracted with EtOAc (4×60 mL). Combined organic phases were washed with brine (2×100 mL), dried ($MgSO_4$), and concentrated. Chromatography (80% EtOAc-hexanes) afforded 2.10 g (95%) of a colorless oil. IR (film) 3440, 1720,1660 $cm^{-1}$; $[\alpha]^{20}_D$+34.95 (c 1.07, $CHCl_3$); $^1H$ NMR ($CDCl_3$) δ 1.31 (s, 3H), 1.57 (m, 1H), 1.74 (m, 2H), 1.84 (m, 1H), 2.30 (m, 1H), 2.39 (s, 3H), 3.49 (m, 1H), 3.71 (s, 3H), 3.94 (m, 4H), 4.07 (d, J=8.0 Hz, 1H), 5.80 (td, J=1.6 Hz, J=15.2 Hz, 1H), 6.80 (td, J=7.2 Hz, J=15.6 Hz, 1H), 7.27 (bd, J=8.0 Hz, 2H), 7.56 (td, J=2.0 Hz, J=8.4 Hz, 2H); $^{13}C$ NMR ($CDCl_3$) δ 21.2, 23.8, 29.7, 35.0, 39.0, 51.4, 53.2, 64.5, 64.6, 109.6, 123.9, 125.5, 129.4, 141.2, 141.9, 144.2, 166.4; HRMS calcd for $C_{19}H_{28}NO_5S$ (M+H) 382.1683. Found 382.1695.

Preparative Example 3a (S$_S$,S)-(+)-Methyl-N-(p-toluenesulfinyl)-5-amino-7-(2-propyl-1,3-dioxolan-2yl)-hep-2-enoate (5a)

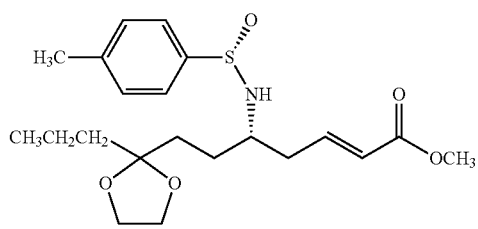

(5a)

The title compound was prepared in manner analogous to the method of Preparative Example 3. Colorless oil; IR (film) 3431, 1722, 1657 cm$^{-1}$. $[\alpha]^{20}_D$+26.64 (c 2.83, CHCl$_3$); $^1$H NMR (CDCl$_3$) δ 0.90 (t, J=7.3 Hz, 3H), 1.40 (m, 2H), 1.56 (m, 3H), 1.66 (m, 2H), 1.84 (m, 1H), 2.26 (m, 1H), 2.36 (m, 1H), 2.39 (s, 3H), 3.48 (m, 1H), 3.71 (s, 3H), 3.92 (bs, 4H), 4.07 (d, J=8.1 Hz, 1H), 5.81 (td, J=15.7 Hz, J=1.2 Hz, 1H), 6.80 (td, J=15.7 Hz, J=7.6 Hz, 1H), 7.27 (bd, J=8.1 Hz, 2H), 7.56 (td, J=8.1 Hz, J=1.7 Hz, 2H); $^{13}$C NMR (CDCl$_3$) δ 14.3, 17.1, 21.3, 29.5, 32.9, 39.1, 39.4, 51.4, 53.3, 64.8 (2C), 111.3, 124.0, 125.5, 129.5, 141.3, 141.9, 144.2, 166.4; HRMS calcd for C$_{21}$H$_{31}$NNaO$_5$S (M+Na) 432.1821. Found 432.1820.

Preparative Example 3b (S$_S$,S)-(+)-Methyl-N-(tert-butylsulfinyl)-5-amino-7-(2-ethyl-1,3-dioxolan-2yl)-hep-2-enoate (5b)

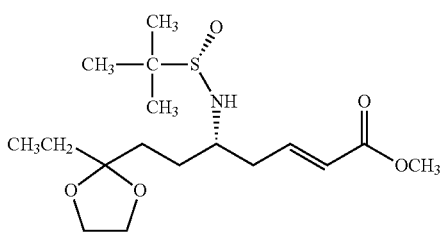

(5b)

In a 100 mL, oven dried, single necked round-bottom flask equipped with magnetic stirring bar and rubber septum was placed trimethyl phosphonoacetate (1.49 g, 8.19 mmol) in acetonitrile (5 mL), DBU (1.24 g, 8.19). A solution of (S$_S$, 3S)-(+)-N-(tert-butylsulfinyl)-3-amino-5-(2-ethyl)-1,3-dioxolan-2-yl)-pentanal (1.25 g, 4.09 mmol) in acetonitrile (5 mL) was added via cannula, the reaction mixture was stirred for 3 hours at rt, and quenched by addition of H$_2$O (40 mL). The solution was extracted with EtOAc (3×20 mL), dried (MgSO$_4$) and concentrated. Flash chromatography (80% EtOAc/hexanes) gave 1.228 g (83%) of a colorless oil; $[\alpha]^{20}_D$+20.0 (c 1.74, CHCl$_3$); IR (film) 3428, 1716, 1651 cm$^{-1}$; $^1$HNMR (CDCl$_3$) δ 0.88 (t, J=7.6 Hz, 3H), 1.20 (s, 9H), 1.61 (m, 10H), 1.70 (b, 1H), 2.57 (m, 2H), 3.16 (d, J=8.1 Hz, 1H), 3.39 (b, 1H), 3.73 (s, 3H), 3.92 (m, 4H), 5.94 (td, J=1.5 Hz, 15.7 Hz, 1H), 6.82 (td, J=7.1 Hz, 15.7 Hz, 1H); $^{13}$CNMR (CDCl$_3$) δ 8.0, 22.5, 29.3, 29.7, 32.4, 39.2, 51.3, 55.8, 55.9, 64.8 (2C's), 111.5, 124.2, 144.0, 166.0; HRMS calcd for C$_{17}$H$_{32}$NO$_5$S (M+H) 362.2001. Found 362.1997.

Preparative Example 3c (S$_S$,S)-(+)-Methyl-N-(tert-butylsulfinyl)-5-amino-7-(2-pentyl-1,3-dioxolan-2yl)-hep-2-enoate (5c)

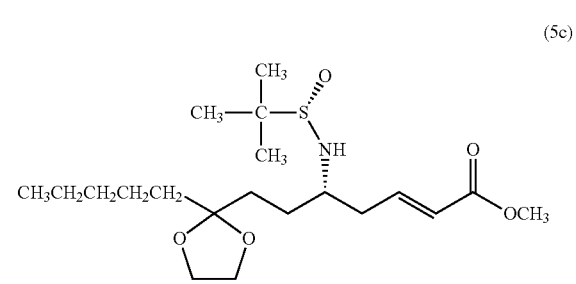

(5c)

The title compound was prepared in manner analogous to the method of Preparative Example 3b. Flash chromatography (75% EtOAc/hexanes) gave 1.13 g (85%) of a colorless oil; $[\alpha]^{20}_D$+16.94 (c 1.31, CHCl$_3$); IR (film) 3428, 1716, 1651 cm$^{-1}$; $^1$HNMR (CDCl$_3$) δ 0.88 (t, J=7.1 Hz, 3H), 1.20 (s, 9H), 1.28 (m, 6H), 1.56 (b, 7H), 1.76 (m, 1H), 2.57 (m, 2H), 3.15 (d, J=7.6 Hz, 1H), 3.38 (m, 1H), 3.73 (s, 3H), 3.92 (m, 4H), 5.94 (td, J=1.5 Hz, 15.7 Hz, 1H), 6.91 (td, J=7.1 Hz, 15.7 Hz, 1H); $^{13}$CNMR (CDCl$_3$) δ 13.9, 22.5, 22.6, 23.4, 29.3, 31.9, 32.9, 37.0, 39.0, 51.4, 55.8, 56.0, 64.8 (2C's), 111.4, 124.4, 144.0, 168.4; HRMS calcd for C$_{20}$H$_{38}$NO$_5$S (M+H) 404.2471. Found 404.2470.

Preparative Example 3d (S$_S$,5S,2E)-(+)-Methyl-N-(t-butylsulfinyl)-5-amino-7-(2-phenyl-1,3-dioxolan-2-yl)hept-2-enoate (5d)

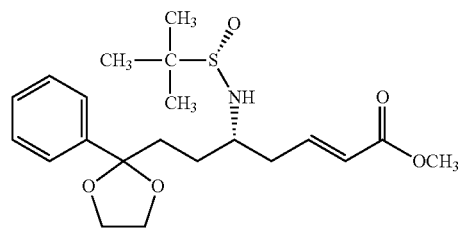

(5d)

The title compound was prepared in manner analogous to the method of Preparative Example 3b. Chromatography (60% EtOAc/Hexanes) afforded 1.53 g (90%) of clear oil as mixture of 95:5 mixture of E:Z isomers; $[\alpha]^{20}_D$+14.41 (c 2.2, CHCl$_3$); $^1$H NMR (CDCl$_3$) δ 1.10 (s, 9H), 1.42 (m, 1H), 1.58 (m, 1H), 1.87 (m, 1H), 1.95 (m, 1H), 2.40 (m, 1H), 2.51 (m, 1H), 3.03 (d, J=7.6 Hz, 1H), 3.29 (m, 1H), 3.65 (s, 3H), 3.68 (m, 2H), 3.92 (m, 2H), 5.82 (td, J=15.6 Hz, J=1.6 Hz, 1H), 6.79 (td, J=15.7 Hz, J=7.1 Hz, 1H), 7.24 (m, 3H), 7.33 (m, 2H); $^{13}$C NMR (CDCl$_3$) δ 22.6, 29.1, 36.3, 39.3, 51.4, 55.6, 56.0, 64.3, 64.4, 110.0, 124.3, 125.5, 127.9, 128.1, 142.2, 144.1, 166.4. HRMS calcd for (M+H)$C_{21}H_{32}NO_5S$ 410.2001. Found 410.1997.

Preparative Example 4

(5S,2E)-(+)-Methyl-(3,4-dihydro-5-methyl-2H-pyrrol-2-yl)-but-2-enoate (6)

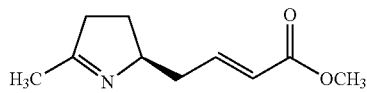

(6)

In a 250 mL, oven-dried, single-neck round-bottomed flask equipped with magnetic stirring bar and a rubber septum was placed (5) (0.12 g, 0.31 mmol) in methanol (MeOH) (15 mL) and THF (15 mL). To this solution was added 3.0 N HCl (1.05 mL) slowly via syringe. This reaction mixture was stirred at room temperature for 16 hours, concentrated, and the residue was dissolved in $CH_2Cl_2$ (50 mL) and washed with saturated aqueous $NaHCO_3$ solution (2×20 mL), brine (30 mL), dried ($MgSO_4$) and concentrated. Chromatography (70% EtOAc/hexanes) gave 0.55 g (100%) of a clear oil; IR (film) 1720, 1655, 1650 cm$^{-1}$; $[\alpha]^{20}_D$+39.67 (c 1.21, CHCl$_3$); $^1$H NMR (CDCl$_3$) δ 1.45 (m, 1H), 2.00 (d, J=1.6 Hz, 3H), 2.02 (m, 1H), 2.33 (m, 1H), 2.45 (m, 2H), 2.58 (m, 1H), 3.69 (s, 3H), 4.05 (m, 1H), 5.87 (td, J=1.6 Hz, J=16.0 Hz, 1H), 6.95 (td, J=7.2 Hz, J=15.6 Hz, 1H); $^{13}$C NMR (CDCl$_3$) δ 19.6, 28.4, 38.9, 39.0, 51.3, 71.2, 122.6, 146.3, 166.8, 175.0. HRMS calcd for $C_{10}H_{16}NO_2$ (M+H) 182.1176. Found 182.1172.

Preparative Example 4a (5S)-(+)-Methyl-(3,4-dihydro-5-propyl-2H-pyrrol-2-yl)-but-2-enoate (6a)

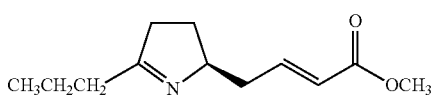

(6a)

The title compound was prepared in manner analogous to the method of Preparative Example 4. Clear oil; IR (film) 1730, 1660, 1653 cm$^{-1}$; $[\alpha]^{20}_D$+39.11 (c 0.9, CHCl$_3$); $^1$H NMR (CDCl$_3$) δ 0.93 (t, J=7.3 Hz, 3H), 1.46 (m, 1H), 1.59 (m, 1H), 2.03 (m, 1H), 2.33 (m, 3H), 2.46 (m, 2H), 2.65 (m, 1H), 3.70 (s, 3H), 4.09 (m, 1H), 5.88 (td, J=15.7 Hz, J=1.5 Hz, 1H), 6.95 (td, J=15.7 Hz, J=7.3 Hz, 1H); $^{13}$C NMR (CDCl$_3$) δ 13.9, 19.8, 27.9, 35.7, 37.1, 39.0, 51.4, 70.9, 122.7, 146.3, 166.8, 178.3. HRMS calcd for $C_{12}H_{20}NO_2$ (M+H) 210.1494. Found 210.1489.

Preparative Example 4b (2E)-(4S)-(+)-Methyl-(3,4-dihydro-5-ethyl-2H-pyrrol-2-yl)-but-2-enoate (6b)

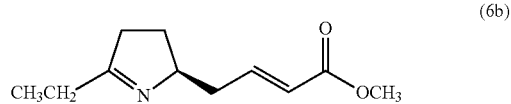

(6b)

The title compound was prepared in manner analogous to the method of Preparative Example 4. Flash chromatography (60% EtOAc/hexanes) gave 0.547 g (82.8%) of an oil; $[\alpha]^{20}_D$+43.36 (c 1.9, CHCl$_3$); IR(neat) 1636, 1698 cm$^{-1}$; $^1$H NMR (CDCl$_3$)™ 1.14 (t, J=7.6 Hz, 3H), 1.46 (m, 1H), 2.04 (m, 1H), 2.33 (m, 3H), 2.49 (m, 2H), 2.65 (m, 1H), 3.72 (s, 3H), 4.09 (m, 1H), 5.89 (td, J=1.6, 15.7 Hz, 1H), 6.96 (td, J=7.6, 15.7 Hz, 1H); $^{13}$C NMR (CDCl$_3$) δ 10.6, 26.7, 27.7, 36.7, 38.8, 51.1, 70.7, 122.5, 146.1, 166.6, 179.2. HRMS calcd for $C_{11}H_{18}NO_2$(M+H) 196.1338. Found 196.1334.

Preparative Example 4c (2E)-(4S)-(+)-Methyl-(3,4-dihydro-5-pentyl-2H-pyrrol-2-yl)-but-2-enoate (6c)

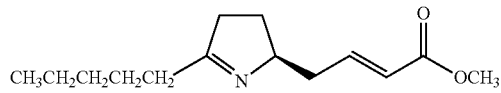

(6c)

The title compound was prepared in manner analogous to the method of Preparative Example 4. Flash chromatography (50% EtOAc/hexanes) gave 0.546 g (83%) of an oil; $[\alpha]^{20}_D$+ 31.06 (c 3.15, CHCl$_3$); IR(neat) 1636, 1698 cm$^{-1}$; $^1$H NMR (CDCl$_3$) δ 0.88 (t, J=6.8 Hz, 3H), 1.31 (m, 4H), 1.50 (m, 3H), 2.03 (m, 1H), 2.40 (m, 5H), 2.63 (m, 1H), 3.72 (s, 3H), 4.09 (m, 1H), 5.88 (td, J=1.5, 15.7 Hz, 1H), 6.96 (td, J=7.3, 15.7 Hz, 11-1); $^{13}$C NMR (CDCl$_3$) δ 13.9, 22.4, 26.2, 27.9, 31.6, 33.8 37.2, 39.0, 51.4, 71.0, 122.7, 146.4, 166.9, 178.6. HRMS calcd for $C_{14}H_{24}NO_2$(M+H) 238.1807. Found 238.1805.

Preparative Example 4d (5S,2E)-(+)-Methyl-(3,4-dihydro-5-phenyl-2H-pyrrol-2-yl)-but-2-enoate (6d)

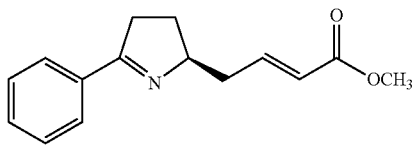

(6d)

The title compound was prepared in manner analogous to the method of Preparative Example 4. Chromatography (30% EtOAc/hexanes) gave 0.620 g (90%) of a clear oil; $[\alpha]^{20}_D$+ 27.53 (c 1.78, CHCl$_3$); $^1$H NMR (CDCl$_3$) δ 1.65 (m, 1H), 2.20 (m, 1H), 2.45 (m, 1H), 2.75 (m, 1H), 2.94 (m, 1H), 3.01 (m, 1H), 3.72 (s, 3H), 4.33 (m, 1H), 5.93 (td, J=15.6 Hz, J=1.6 Hz, 1H), 7.04 (td, J=15.6 Hz, J=7.6 Hz, 1H), 7.41 (m, 3H), 7.83 (m, 2H); $^{13}$C NMR (CDCl$_3$) δ 28.0, 35.1, 39.1, 51.4, 71.7, 122.8, 127.7, 128.4, 130.5, 134.3, 146.3, 166.8, 172.9. HRMS calcd for C$_{15}$H$_{18}$NO$_2$ (M+H) 244.1338. Found 244.1329.

Preparative Example 5

(5S,2E)-Methyl-(3,4-dihydro-5-methyl-2H-pyrrol-2-yl)-but-2-enoate-N-oxide (7)

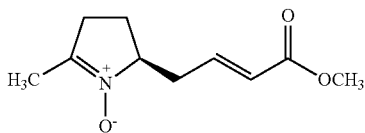

(7)

In a 50 mL, oven-dried, single-neck round-bottomed flask equipped with magnetic stirring bar and a rubber septum was placed urea hydrogen peroxide (0.743 g, 7.898 mmol) in anhydrous MeOH (30 mL) under argon. Methyltrioxorhenium (0.041 g, 0.165 mmol) was added, the solution was stirred for 15 min and (6) (0.440 g, 2.43 mmol) in MeOH (20 mL) was added via cannula. The yellow solution was stirred at room temperature for 15 hours, concentrated, and the residue was dissolved in CH$_2$Cl$_2$ (20 mL). The suspended urea crystals were filtered, the solution concentrated to gave 0.47 g (98%) of a yellow oil, which was taken to the next step without further purification.

$^1$H NMR (CDCl$_3$) δ 1.80 (m, 1H), 2.07 (s, 3H), 2.28 (m, 1H), 2.63 (m, 3H), 2.99 (m, 1H), 3.72 (s, 3H), 4.20 (m, 1H), 5.95 (td, J=1.5 Hz, J=15.7 Hz, 1H), 6.84 (td, J=7.3 Hz, J=15.7 Hz, 1H). HRMS calcd for C$_{10}$H$_{16}$NO$_3$ (M+H) 198.1125. Found 198.1130

Preparative Example 6

(1S,2R,3R,6S)-(−)-Methyl-3-methyl-7-aza-8-oxatricyclo[4,2,1,0]-nonane-2-carboxylate (8)

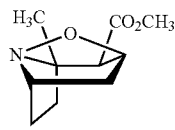

(8)

In a 500 mL, oven-dried, single-neck round-bottomed flask equipped with magnetic stirring bar and a rubber septum was placed (7) (0.400 g, 2.028 mmol) in anhydrous toluene (400 mL) and the solution was refluxed (while maintaining the oil bath temperature at 150° C.) for 48 hours and concentrated. Purification by flash column chromatography gave 0.180 g (45%) of a white solid.

$[\alpha]^{20}_D$-56.47 (c 0.42, CHCl$_3$). $^1$H NMR (CDCl$_3$) δ 1.24 (s, 3H), 1.81 (m, 3H), 2.18 (m, 3H), 2.44 (s, 1H), 3.61 (m, 1H), 3.68 (s, 3H), 4.94 (d, J=4.8 Hz, 1H). $^{13}$C NMR (CDCl$_3$) δ 22.0, 26.0, 33.8, 42.0, 51.5, 61.2, 62.7, 75.7, 81.5, 171.6. HRMS calcd for C$_{10}$H$_{16}$NO) (M+H) 198.1130. Found 198.1124. [Calcd for C$_{10}$H$_{15}$NaNO$_3$ (M+Na) 220.0950. Found 220.0939]

Preparative Example 6a

Methyl (1S,2R,3R,6S)-(−)-3-propyl-7-aza-8-oxatricyclo[4,2,1,0]-nonane-2-carboxylate (8a)

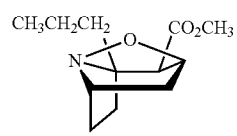

(8a)

The title compound was prepared in manner analogous to the method of Preparative Example 6. Clear oil. IR (film) 1738 cm$^{-1}$; $[\alpha]^{20}_D$-56.62 (c 0.71, CHCl$_3$); $^1$H NMR (CDCl$_3$) δ 0.88 (t, J=7.1 Hz, 3H), 1.25 (dd, J=11.5 Hz, J=2.2 Hz, 1H), 1.31 (m, 1H), 1.49 (m, 3H), 1.80 (m, 1H), 1.99 (m, 2H), 2.15 (m, 2H), 2.46 (s, 1H), 3.60 (m, 1H), 3.68 (s, 3H); $^{13}$C NMR (CDCl$_3$) δ 14.6, 17.7, 25.9, 30.1, 35.9, 42.0, 51.6, 62.3, 62.8, 79.0, 81.6, 171.9. HRMS calcd for C$_{12}$H$_{19}$NNaO$_3$ (M+Na) 248.1263. Found 248.1260.

Preparative Example 6b (1S,2R,3R,6S)-(−)-Methyl-3-ethyl-7-aza-8-oxatricyclo[4,2,1,0]-nonane-2-carboxylate (8b)

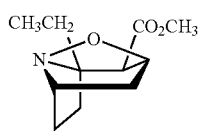

(8b)

The title compound was prepared in manner analogous to the method of Preparative Example 6. Clear oil; $[\alpha]^{20}_D$-27.272 (c 0.495, CHCl$_3$); IR(film) 1738 cm$^{-1}$; $^1$H NMR (CDCl$_3$) δ 0.945 (t, J=7.6 Hz, 3H), 1.26 (dd, J=11.7, 2.4 Hz, 2H), 1.57 (q, J=7.6 Hz, 2H), 1.85 (m, 1H), 1.98 (m, 2H), 2.14 (m, 2H), 2.47 (s, 2H), 3.61 (m, 1H), 3.68 (s, 3H), 3.74 (m, 1H), 4.90 (d, J=4.8 Hz, 1H); $^{13}$C NMR (CDCl$_3$) δ 8.7, 25.8, 26.1, 29.3, 41.9, 51.5, 62.3, 62.8, 81.6, 171.9. HRMS calcd for C$_{11}$H$_{18}$NO$_3$(M+H) 212.1287. Found 212.1282.

Preparative Example 6c (1S,2R,3R,6S)-(−)-Methyl-3-pentyl-7-aza-8-oxatricyclo[4,2,1,0]-nonane-2-carboxylate (8c)

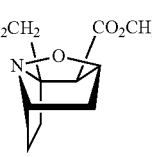

(8c)

The title compound was prepared in manner analogous to the method of Preparative Example 6. Clear oil; $[\alpha]^{20}_D$-45.647 (c 1.275, CHCl$_3$); IR(film) 1738 cm$^{-1}$; $^1$H NMR (CDCl$_3$) δ 0.86 (t, J=7.1 Hz, 3H), 1.25 (b, 7H), 1.49 (b, 4H), 1.81 (m, 1H), 2.0 (m, 2H), 2.18 (m, 2H), 2.48 (s, 1H), 3.65 (m, 1H), 3.69 (s, 3H), 4.91 (d, J=4.8 Hz, 1H); $^{13}$C NMR (CDCl$_3$) δ 14.0, 22.6, 24.2, 25.9, 30.1, 32.4, 33.7, 42.0, 51.5, 62.2, 62.8, 79.1, 81.6, 171.8. HRMS calcd for C$_{14}$H$_{24}$NO$_3$(M+H) 254.1756. Found 254.1752.

Preparative Example 6d (1S,2R,3R,6S)-(−)-Methyl-3-phenyl-7-aza-8-oxatricyclo[4,2,1,0]-nonane-2-carboxylate (8d)

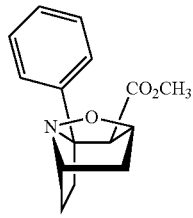

The title compound was prepared in manner analogous to the method of Preparative Example 6. Chromatography (35% EtOAc/hexanes) gave 0.31 g (40%) of a white solid, mp 136-138° C.] and 0.30 g (38%) of the amide; $[\alpha]^{20}_D$-54.69 (c 0.88, CHCl$_3$); $^1$H NMR (CDCl$_3$) δ 1.38 (dd, J=11.7 Hz, J=2.4 Hz, 1H), 1.93 (m, 1H), 2.22 (m, 2H), 2.28 (m, 1H), 2.73 (m, 1H), 2.81 (s, 1H), 3.04 (s, 3H), 3.75 (m, 1H), 4.95 (d, J=4.9 Hz, 1H), 7.14 (m, 1H), 7.23 (m, 2H), 7.45 (m, 2H); $^{13}$C NMR (CDCl$_3$) δ 25.4, 34.1, 42.2, 50.9, 63.0, 64.5, 80.7, 81.2, 126.6, 126.8, 127.3, 141.5, 170.6. HRMS calcd for (M+H) C$_{15}$H$_{18}$NO$_3$ 260.1287. Found 260.1281.

Preparative Example 7

(1S,2R,3R,6S)-(−)-Methyl-3-methyl-7-aza-8-oxatricyclo[4,2,1,0]-nonane-2-carboxylate (8)

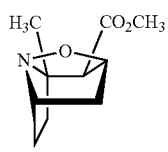

In a 500 mL, oven-dried, single-neck round-bottomed flask equipped with magnetic stirring bar and a rubber septum was placed (7) (0.370 g, 1.876 mmol) in anhydrous toluene (200 mL). To this solution was added aluminum tri-tert-butoxide (0.230 g, 0.938 mmol) and the solution was stirred at room temperature for 6 hours. At this time the reaction mixture was refluxed for 96 hours, cooled to room temperature, and extracted with aqueous 5% HCl solution (4×50 mL). The combined aqueous phases were carefully neutralized by slow addition of solid sodium carbonate until the solution became slightly basic (pH 8). This aqueous solution was extracted with dichloromethane (4×50 mL) and the combined organic phases were washed with brine, dried (over anhydrous magnesium sulfate) and concentrated. Purification by chromatography gave 0.260 g (70%) of a low-melting solid with spectral properties identical to those of the isolated compound in Preparative Example 6.

Preparative Example 8

Methanesulfonate salt of methyl (1S,2R,3R,6S)-(−)-3,7-dimethyl-7-aza-8-oxatricyclo[4,2,1,0]-nonane-2-carboxylate (9)

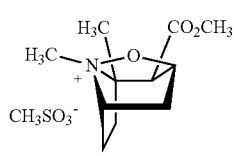

In a 50 mL, oven-dried, single-neck round-bottomed flask equipped with magnetic stirring bar and a reflux condenser was placed (8) (0.06 g, 0.304 mmol) in anhydrous benzene (20 mL) under argon. Methylmethanesulfonate (0.335 g, 3.04 mmol) was added via syringe and the solution was heated at refluxed for 24 hours. At this time the solution was concentrated, the residue was dissolved in H$_2$O (20 mL). This aqueous solution was extracted with CH$_2$Cl$_2$ (3×10 mL) and the aqueous phase was concentrated to give 0.92 g (98%) of a white sticky material; IR (film) 1745 cm$^{-1}$; $[\alpha]^{20}_D$-2.85 (c 0.7, CHCl$_3$); $^1$H NMR (CD$_3$OD) δ 1.45 (s, 3H), 2.12 (dd, J=2.4 Hz, J=12.7 Hz, 1H), 2.28 (m, 2H), 2.50 (m, 1H), 2.58 (m, 1H), 2.62 (s, 3H), 2.77 (m, 1H), 3.42 (s, 3H), 3.50 (s, 1H), 3.71 (s, 3H), 4.43 (tq, J=8.6 Hz, J=2.0 Hz, 1H), 5.36 (d, J=5.2 Hz, 1H); $^{13}$C NMR (CD$_3$OD) δ 18.2, 25.6, 34.1, 39.7, 41.6, 41.7, 53.1, 60.8, 78.3, 84.0, 88.1, 170.2. HRMS calcd for C$_{11}$H$_{18}$NO$_3$ (M$^+$) 212.1281. Found 212.1279.

Preparative Example 8a

Methansulfonate salt of methyl (1S,2R,3R,6S)-(+)-3-propyl-7-methyl-7-aza-8-oxatricyclo[4,2,1,0]-nonane-2-carboxylate (9a)

The title compound was prepared in manner analogous to the method of Preparative Example 8. Sticky solid; IR (film) 1750 cm$^{-1}$; $[\alpha]^{20}_D$+14.28 (c 0.77, CHCl$_3$);
$^1$H NMR (CD$_3$OD) δ 0.87 (t, J=7.3 Hz, 3H), 1.13 (m, 1H), 1.28 (m, 1H), 1.82 (m, 2H), 2.08 (dd, J=12.5 Hz, J=2.7 Hz, 1H), 2.25 (m, 2H), 2.41 (m, 1H), 2.52 (m, 1H), 2.58 (m, 1H), 2.59 (s, 3H), 2.74 (m, 1H), 3.41 (s, 3H), 3.42 (s, 1H), 3.66 (s, 3H), 4.36 (m, 1H), 5.26 (d, J=4.9 Hz, 1H); $^{13}$C NMR (CD$_3$OD) δ 14.8, 19.0, 25.4, 32.9, 34.7, 39.6, 41.7, 41.9, 53.2, 60.0, 78.9, 85.0, 91.5, 171.1. HRMS calcd for C$_{13}$H$_{22}$NO$_3$ (M$^+$) 240.1594. Found 240.1598.

Preparative Example 8b

Methanesulfonate salt of methyl (1S,2R,3R,6S)-(+)-3-ethyl-7-methyl-7-aza-8-oxatricyclo[4,2,1,0]-nonane-2-carboxylate (9b)

The title compound was prepared in manner analogous to the method of Preparative Example 8. Sticky material; $[\alpha]^{20}_D$+10.7169 (c 3.975, MeOH); IR(film) 1748 cm$^{-1}$; $^1$H NMR (CD$_3$OD) δ 0.637 (t, J=7.6 Hz, 3H), 1.69 (m, 2H), 1.89

(dd, J=12.8, 2.7 Hz, 1H), 2.02 (m, 2H), 2.2 (m, 1H), 2.33 (m, 1H), 2.40 (s, 3H), 2.51 (m, 1H), 3.01 (s, 1H), 3.18 (s, 3H), 3.22 (s, 1H), 3.43 (s, 3H), 4.16 (m, 1H), 5.04 (d, J=5.1 Hz, 1H); $^{13}$C NMR (CD$_3$OD) δ 8.8, 25.0, 25.5, 32.4, 39.5, 41.4, 41.8, 53.0, 59.7, 79.0, 84.7, 91.9, 170.9. HRMS calcd for C$_{12}$H$_{20}$NO$_3$ (M+) 226.1443. Found 226.1438.

Preparative Example 8c

Methanesulfonate salt of methyl (1S,2R,3R,6S)-(+)-3-pentyl-7-methyl-7-aza-8-oxatricyclo[4,2,1,0]-nonane-2-carboxylate (9c)

The title compound was prepared in manner analogous to the method of Preparative Example 8. Sticky material; [α]$^{20}_D$+13.868 (c 1.06, MeOH); IR(film) 1748 cm$^{-1}$; $^1$H NMR (CD$_3$OD) δ 0.84 (t, J=7.1 Hz, 3H), 1.20 (m, 6H), 1.81 (dt, J=4.4, 12.5 Hz, 1H), 1.94 (m, 1H), 2.1 (dd, J=2.7, 12.5 Hz, 1H), 2.25 (m, 2H), 2.41 (m, 1H), 2.57 (m, 1H), 2.62 (s, 3H), 2.75 (m, 1H), 3.43 (s, 3H), 3.44 (s, 1H), 4.16 (m, 1H), 3.68 (s, 3H), 4.37 (m, 1H), 5.29 (d, J=5.1 Hz, 1H); $^{13}$C NMR (CD$_3$OD) δ 13.1, 22.3, 24.1, 24.2, 31.6, 31.8, 32.2, 38.4, 40.5, 40.7, 52.1, 58.8, 77.8, 83.8, 90.5, 169.9. HRMS calcd for C$_{15}$H$_{26}$NO$_3$(M+) 268.1907. Found 268.1912.

Preparative Example 8d

Methanesulfonate salt of methyl (1S,2R,3R,6S)-(−)-3-phenyl-7-aza-8-oxatricyclo[4,2,1,0]-nonane-2-carboxylate (9d)

In a 100 mL, oven-dried, single-neck round-bottomed thick walled flask equipped with magnetic stirring bar was placed (−)-isoxazolidine (0.20 g, 0.77 mmol) in anhydrous dichloromethane (30 mL) under argon methylmethanesulfonate (1.69 g, 15.43 mmol) was added to above solution via syringe and heated at refluxed for 72 hours. At this time the solution was concentrated, the residue was dissolved in H$_2$O (50 mL). This aqueous solution was extracted with CH$_2$Cl$_2$ (3×30 mL) and the aqueous phase was concentrated to give 0.27 g (95%) of a white sticky material; [α]$^{20}_D$+38.88 (c 1.62, CH$_3$OH); $^1$H NMR (CD$_3$OD) δ 2.21 (dd, J=12.5 Hz, J=1.7 Hz, 1H), 2.40 (m, 1H), 2.55 (s, 3H), 2.65 (m, 1H), 2.77 (m, 1H), 2.88 (m, 1H), 2.91 (s, 3H), 2.99 (m, 1H), 3.21 (s, 3H), 3.85 (s, 1H), 4.59 (m, 1H), 5.60 (d, J=4.6 Hz, 1H), 7.36 (m, 3H), 7.45 (m, 2H); $^{13}$C NMR (CD$_3$OD) δ 25.8, 31.3, 39.7, 42.7, 42.9, 52.7, 62.9, 80.1, 83.8, 91.8, 129.6, 130.2, 131.9, 133.5, 169.7. HRMS calcd for C$_{16}$H$_{20}$NO$_3$ (M$^+$) 274.1443. Found 274.1440.

Preparative Example 9

Methanesuflonate salt of methyl (1R,2R,3S,5S)-(−)-3-(hydroxy)-8-methyl-8-azabicyclo[3.2.1]octane-2-carboxylate (10)

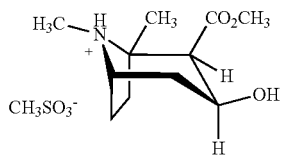

(10)

In a 50 mL, oven-dried, single-neck round-bottomed flask equipped with magnetic stirring bar and a rubber septum was placed (9) (0.030 g, 0.097 mmol) in anhydrous MeOH (10 mL) under H$_2$ gas (1 atm pressure was maintained using a balloon). Pd—C (0.01 g, 5% Pd on carbon) was added and the solution was stirred at room temperature for 48 hours. At this time the catalyst was removed by filtration using a short pad of Celite, the filtrate was concentrated to give 0.03 g (99%) of a white sticky solid; IR (film) 3400, 1750, cm$^{-1}$; [α]$^{20}_D$−24.17 (c 1.17, MeOH); $^1$H NMR (CD$_3$OD) δ 1.38 (s, 3H), 1.99 (m, 1H), 2.07 (m, 4H), 2.28 (m, 1H), 2.63 (s, 3H), 2.71 (s, 3H), 3.12 (d, J=6.8 Hz, 1H), 3.73 (s, 3H), 3.84 (m, 1H), 4.28 (td, J=6.6 Hz, J=11.0 Hz, 1H); $^{13}$C NMR (CD$_3$OD) δ 20.8, 25.3, 32.4, 36.4, 36.5, 39.6, 53.2, 57.0, 63.1, 66.8, 71.8, 175.7. HRMS calcd for C$_{11}$H$_{20}$NO$_3$ 214.1434. Found 214.1434.

Preparative Example 9a

Methanesulfonate salt of methyl (1R,2R,3S,5S)-(+)-1-propyl-3-(hydroxy)-8-methyl-8-azabicyclo[3.2.1]octane-2-carboxylate (10a)

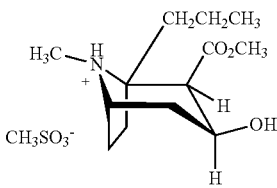

(10a)

The title compound was prepared in manner analogous to the method of Preparative Example 9. Sticky solid; IR (film) 3340, 1745 cm$^{-1}$; [α]$^{20}_D$+1.69 (c 0.82, MeOH); $^1$H NMR (CD$_3$OD) δ 0.85 (t, J=7.3 Hz, 3H), 1.15 (m, 1H), 1.35-1.71 (m, 7H), 1.97 (m, 1H), 2.10 (m, 1H), 2.12 (s, 3H), 2.60 (s, 3H), 2.89 (d, J=6.6 Hz, 1H), 3.17 (m, 1H), 3.57 (s, 3H), 3.88 (m, 1H); $^{13}$C NMR (CD$_3$OD) δ 15.4, 19.5, 27.2, 33.7, 36.6, 37.7, 39.6, 39.9, 51.6, 55.6, 64.3, 65.7, 69.1, 173.6. HRMS calcd for C$_{13}$H$_{24}$NO$_3$ (M$^+$) 242.1751. Found 242.1751.

Preparative Example 9b

Methanesulfonate salt of methyl (1R,2R,3S,5S)-(−)-1-ethyl-3-(hydroxyl)-8-methyl-8-azabicyclo[3.2,1]octane-2-carboxylate (10b)

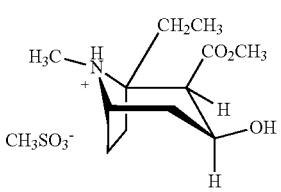

(10b)

The title compound was prepared in manner analogous to the method of Preparative Example 9. Sticky solid; [α]$^{20}_D$−7.595 (c 4.055, MeOH); IR(film) 3380, 1749 cm$^{-1}$; $^1$H NMR (CD$_3$OD) δ 0.94 (t, J=7.6 Hz, 3H), 1.56 (m, 1H), 1.80 (m, 1H), 1.99 (m, 3H), 2.14 (m, 2H), 2.28 (m, 1H), 2.61 (s, 4H), 2.69 (s, 3H), 3.26 (s, 2H), 3.3 (d, J=7.3 Hz, 1H), 3.73 (s, 3H), 3.83 (b, 1H), 4.24 (m, 1H); $^{13}$C NMR (CD$_3$OD) δ 9.2, 24.9, 27.9, 30.2, 36.2, 52.6, 53.1, 63.0, 66.8, 75.1, 175.2. HRMS calcd for C$_{12}$H$_{22}$NO$_3$(M+) 228.1594. Found 228.1592.

Preparative Example 9c

Methanesulfonate salt of methyl (1R,2R,3S,5S)-(+)-1-pentyl-3-(hydroxyl)-8-methyl-8-azabicyclo[3.2,1]octane-2-carboxylate (10c)

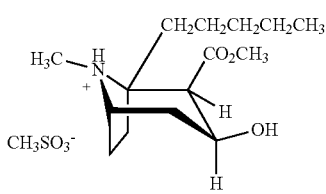

(10c)

The title compound was prepared in manner analogous to the method of Preparative Example 9. Sticky solid; [α]$^{20}_D$+ 3.488 (c 0.43, MeOH); IR(film) 3380, 1749 cm$^{-1}$; $^1$H NMR (CD$_3$OD) δ 0.87 (t, J=7.1 Hz, 3H), 1.35 (b, 6H), 1.61 (m, 1H), 1.73 (m, 1H), 2.07 (b, 5H), 2.31 (b, 1H), 2.65 (s, 3H), 2.73 (s, 3H), 3.32 (d, J=7.1 Hz, 1H), 3.75 (s, 3H), 3.87 (b, 1H), 4.28 (m, 1H); $^{13}$C NMR (CD$_3$OD) δ 14.2, 23.2, 25.1, 25.3, 30.8, 33.0, 35.1, 36.3, 36.5, 39.7, 53.1, 53.5, 63.1, 66.7, 74.7, 175.2. HRMS calcd for C$_{15}$H$_{28}$NO$_3$ (M+) 270.2064. Found 270.2066.

Preparative Example 9d

Methanesulfonate salt of Methyl (1R,2R,3S,5S)-(−)-3-(hydroxy)-1-phenyl-8-methyl-8-azabicyclo[3.2.1]octane-2-carboxylate (10d)

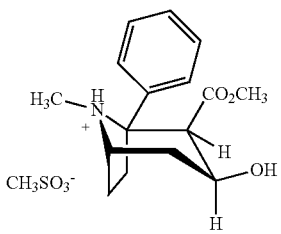

(10d)

In a 50 mL, oven-dried, single-neck round-bottomed flask equipped with magnetic stirring bar, and a rubber septum was placed methanesulfonate salt of methyl (1S,2R,3R,6S)-(+)-3-phenyl-7-aza-8-oxatricyclo[4,2,1,0]-nonane-2-carboxylate (0.160 g, 0.433 mmol) in anhydrous MeOH (10 mL), Pd—C (0.01 g, 5% Pd on Carbon) was added. A hydrogen atmosphere (1 atm) was maintained using a balloon, and the reaction mixture was stirred at rt for 12 hours. At this time the solution was filtered through a short pad of Celite, and concentrated to give 0.159 g (99%) of sticky material. Attempts to purify this material by chromatography (2% MeOH in DCM) proved unsuccessful and the crude mixture was taken on the next step without additional purification.

Example 1

Methyl (1R,2R,3S,5S)-(−)-3-(benzoyloxy)-1,8-dimethyl-8-azabicyclo[3.2.I]octane-2-carboxylate (11)

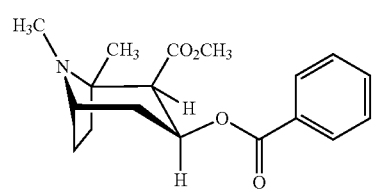

(11)

In a 25 mL, oven-dried, single-neck round-bottomed flask equipped with magnetic stirring bar and a rubber septum was placed (10) (0.03 g, 0.097 mmol) in anhydrous pyridine (1.0 mL) under argon. Benzoyl chloride (0.020 g, 0.145 mmol) was slowly added and the solution was stirred at room temperature for 20 hours. At this time the solvent was removed, and saturated aqueous potassium carbonate (30 mL) was added to the residue and the solution was stirred for 10 minutes. At this time the aqueous solution was extracted with CHCl$_3$ (3 ×20mL), the combined organic phases were dried (MgSO$_4$), and concentrated to give 0.029 g (94%) of a syrupy oil. Chromatography (1% NH$_4$OH in 40% EtOAc/hexanes) gave 0.029 g (94%) of a syrupy oil; IR (film) 1720, 1645 cm$^{-1}$; [α]$^{20}_D$-8.32 (c 1.25, CHCl$_3$); $^1$H NMR (CDCl$_3$) δ 1.27 (s, 3H), 1.72 (m, 1H), 1.81 (m, 2H), 1.89 (m, 1H), 2.14 (m, 1H), 2.26 (s, 3H), 2.50 (dt, J=2.7 Hz, J =12.0 Hz, 1H), 2.94 (d, J=6.8 Hz, 1H), 3.36 (m, 1H), 3.64 (s, 3H), 5.36 (td, J=6.4 Hz, J=11.7 Hz, 1H), 7.40 (m, 2H), 7.54(m, 1H), 7.95(m, 2H); $^{13}$C NMR (CDCl$_3$) δ 22.7, 26.7, 34.2, 34.5, 36.8, 51.1, 55.5, 62.8, 64.9, 68.4, 128.3, 129.5, 130.1, 132.9, 165.9, 170.4. HRMS calcd for C$_{18}$H$_{24}$NO$_4$ (M+H) 318.1705. Found 318.1701.

Example 2

Methyl (1R,2R,3S,5S)-(−)-1-propyl-3-(benzoyloxy)-8-methyl-8-azabicyclo[3.2.1]octane-2-carboxylate (11a)

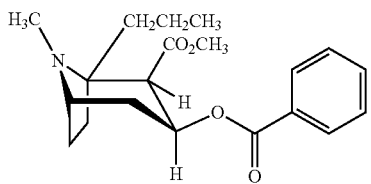

(11a)

The title compound was prepared in manner analogous to the method of Example 1, substituting (10a) for (10). Chromatography (1% NH$_4$OH in 40% EtOAc/hexanes) gave a syrupy oil; IR (film) 1719, 1641 cm$^{-1}$; [α]$^{20}_D$-3.00 (c 0.4, CHCl$_3$); $^1$H NMR (CDCl$_3$) δ 0.94 (t, J=7.3 Hz, 3H), 1.23 (m, 1H), 1.44 (m, 1H), 1.66 (m, 2H), 1.76 (m, 1H), 1.84 (m, 1H), 2.08 (m, 1H), 2.30 (s, 3H), 2.53 (dt, J=12.0 Hz, J=2.4 Hz, 1H), 3.15 (d, J=6.6 Hz, 1H), 3.39 (m, 1H), 3.63 (s, 3H), 5.33 (m, 1H), 7.40 (m, 2H), 7.53 (m, 1H), 7.95 (m, 1H); $^{13}$C NMR (CDCl$_3$) δ 15.0, 18.2; 26.3, 32.9, 33.4, 36.1, 38.5, 51.1, 51.4, 62.4, 67.8, 68.6, 128.3, 129.6, 130.2, 132.9, 165.9, 170.6. HRMS calcd for C$_{20}$H$_{28}$NO$_4$ (M+H) 346.2018. Found 346.2019.

Example 3

Methyl (1R,2R,3S,5S)-(−)-1-ethyl-3-(benzoyloxy)-8-methyl-8-azabicyclo[3.2.1]octane-2-carboxylate (11b)

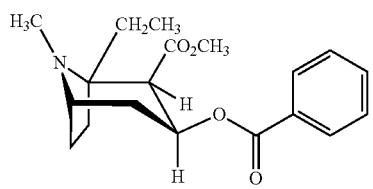

(11b)

The title compound was prepared in manner analogous to the method of Example 1, substituting (10b) for (10). Flash chromatography (1% NH4OH+EtOAc) gave 0.109 g (75%) of oil; [α]$^{20}_D$−1.831 (c 1.365, CHCl$_3$); IR (film) 1721, 1646 cm$^{-1}$; $^1$H NMR (CDCl$_3$) δ 0.99 (t, J=7.6 Hz, 3H), 1.61 (m, 3H), 1.75 (m, 2H), 1.84 (m, 1H), 2.07 (m, 1H), 2.28 (s, 3H), 2.53 (td, J=11.7, 2.7 Hz, 1H), 3.16 (d, J=6.4 Hz, 1H), 3.39 (m, 1H), 3.62 (s, 3H), 5.34 (m, 1H), 7.4 (m, 2H), 7.53 (m, 1H), 7.95 (m, 2H); $^{13}$C NMR (CDCl$_3$) δ 9.2, 26.1, 28.5, 29.6, 32.4, 33.2, 35.9, 50.7, 51.0, 62.5, 68.1, 68.5, 128.2, 129.5, 130.1, 132.9, 165.8, 170.5. HRMS calcd for C$_{19}$H$_{26}$NO$_4$(M+H) 332.1862. Found 332.1858.

Example 4

Methyl (1R,2R,3S,5S)-(+)-1-pentyl-3-(benzoyloxy)-8-methyl-8-azabicyclo[3.2.1]octane-2-carboxylate (11c)

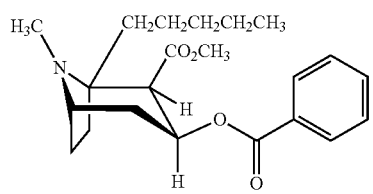

(11c)

The title compound was prepared in manner analogous to the method of Example 1, substituting (10c) for (10). Flash chromatography (1% NH4OH+EtOAc) gave 0.134 g (72%) of oil; [α]$^{20}_D$+6.66 (c 1.2, CHCl$_3$); IR (film) 1721, 1646 cm$^{-1}$; $^1$H NMR (CDCl$_3$) δ 0.89 (t, J=7.1 Hz, 3H), 1.37 (b, 6H), 1.62 (b, 5H), 1.77 (m, 2H), 1.84 (b, 1H), 2.09 (b, 1H), 2.30 (s, 3H), 2.54 (dt, J=2.7, 12.2 Hz, 1H), 3.16 (d, J=6.8 Hz, 1H), 3.39 (b, 1H), 3.62 (s, 3H), 5.34 (m, 1H), 7.41 (m, 2H), 7.52 (m, 1H), 7.96 (m, 2H); $^{13}$C NMR (CDCl$_3$) δ 13.9, 22.4, 24.4, 26.2, 32.6, 32.9, 33.2, 36.0, 36.1, 51.0, 51.3, 62.4, 67.7, 68.6, 128.2, 129.5, 130.1, 132.9, 165.8, 170.5; HRMS calcd for C$_{22}$H$_{32}$NO$_4$(M+H) 374.2331. Found 374.2327.

Example 5

Methyl (1R,2R,3S,5S)-(−)-3-(benzoyloxy)-1-phenyl-8-methyl-8-azabicyclo[3.2.1]octane-2-carboxylate (11d).

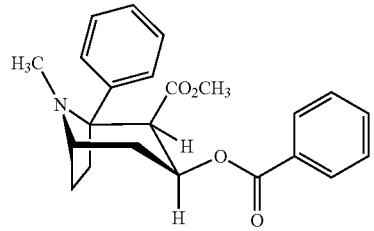

(11d)

The title compound was prepared in manner analogous to the method of Example 1, substituting (10d) for (10). Chromatography (40% EtOAc/hexanes) gave 0.095 g (80%) of a syrupy oil; [α]$^{20}_D$+33.61 (c 1.8, CHCl$_3$); $^1$H NMR (CD$_3$OD) δ 2.31 (m, 1H), 2.44 (m, 1H),2.51(m, 1H), 2.62 (m, 1H), 2.69 (m, 1H), 2.71 (s, 3H), 2.90 (m, 1H), 3.37 (s, 3H), 3.50 (d, J=6.8 Hz, 1H), 4.24 (m, 1H), 5.64 (td, J=11.6 Hz, J=6.3 Hz, 1H), 7.24 (m, 2H), 7.39 (m, 5H), 7.53 (m, 1H), 7.80 (m, 2H); $^{13}$C NMR (CD$_3$OD) δ 24.8, 31.8, 33.3, 39.4, 53.6, 57.1, 66.9, 67.4, 77.5, 128.5, 129.9, 130.4, 130.6, 130.8, 130.9, 135.1, 136.9, 166.3, 173.2. HRMS calcd for C$_{23}$H$_{26}$NO$_4$ (M+H) 380.1862. Found 380.1859.

Example 6

Biochemical Evaluation of the Compounds of the Invention

Cocaine blocks the reuptake of dopamine (DA), serotonin (5-HT) and norephinephrine (NE). It is believed that the dopamine transporter (DAT) is a key receptor for cocaine regarding reinforcing effects of the drug. The natural substrates are DA for DAT, NE for NET, and 5-HT for the serotonin transporter (SERT). However, DA is a substrate for NET with better affinity than NE itself and we have seen no differences in pharmacological profile of NET between [3H]NE and [3H]DA assays.

Cocaine analogs were evaluated for their potency in inhibiting uptake of the substrate [3H]DA for DAT and NET, and [3H]5-HT for the serotonin transporter (SERT). The measurements were made in cells heterologously expressing the cloned human DAT, SERT, or NET, respectively. CFT, fluoxetine and desipramine were included as positive controls for DAT, SERT and NET, respectively. Cocaine was also included in the study.

The uptake of radiolabeled dopamine was monitored into cells expressing the human DAT as described by Chen et al., J. Neurochem. 2004, 89:853-864. The same general methods were used to assay SERT and NET with radiolabeled 5-HT and norepinephrine, respectively. The SERT cells used were those described by Eshleman et al., J. Pharmacol. Exp. Ther. 1995, 274:276-283, and the NET cells were those described by Reith et al., J. Neurosci. Methods 2005, 143:87-94.

The results of the biochemical studies, shown in Table I, indicate that, as compared to cocaine, compounds 11 and 11b had somewhat higher potency with respect to DAT, slightly lower potency with respect to NET and unchanged (11) or lower (11b) potency with respect to SERT. Elongating the length of the substituent from methyl to pentyl (11 to 11c) reduced DAT potency indicating interference from increasing bulk at the C1 position of the tropane ring. This appeared to be the case also for SERT and NET. Compound 11d, the analog with the phenyl substituent, was highly interesting in displaying an increased affinity for DAT compared with cocaine by an order of magnitude, whereas its affinity for SERT and NET was more comparable to that of compounds 11b and 11c, respectively.

TABLE I

Uptake experiments $K_i$ values (nM), as mean ± SEM. Number of experiments is indicated in parenthesis.

| Compound | $R^{1a}$ | DAT (mean) | SERT (mean) | NET (mean) |
|---|---|---|---|---|
| 11 | methyl | 168 ± 23 (n = 8) | 435 ± 77 (n = 8) | 488 ± 101 (n = 7) |
| 11b | ethyl | 95.1 ± 17 (n = 3) | 1,106 ± 112 (n = 3) | 598 ± 179 (n = 3) |
| 11a | n-propyl | 871 ± 205 (n = 4) | 2,986 ± 462 (n = 4) | 796 ± 195 (n = 3) |
| 11c | n-pentyl | 1,272 ± 199 (n = 3) | 1,886 ± 400 (n = 4) | 1596 ± 21 (n = 4) |
| 11d | phenyl | 31.9 ± 5.7 (n = 3) | 974 ± 308 (n = 4) | 1,980 ± 99 (n = 3) |
| cocaine | hydrogen | 326 ± 106 (n = 3) | 513 ± 143 (n = 3) | 358 ± 69 (n = 3) |
| CFT | — | 39.2 ± 7.1 (n = 5)± | — | — |
| fluoxetine | — | — | 27.3 ± 9.2 (n = 3) | — |
| desipramine | — | — | — | 2.74 ± 0.59 (n = 3) |

Example 7

Locomotor Stimulator Activity

Many, but not all, psychostimulants with potent action at DAT, also stimulate locomotor ambulatory activity in rodents. Compounds 11, 11a, 11b and 11c were tested for effect on locomotor ambulatory activity as described by Sershen et al., *Genes Brain Behav.* 2002, 1:156-165. Male C57BL/6 mice were contained in a box equipped with infrared beams, the consecutive interruption of which by horizontal activity by the mouse provided a measure for ambulation. All compounds produced much less locomotor stimulation than cocaine. Administered intraperitoneally at 10 or 30 mg/kg, cocaine dose-dependently increased locomotion, with 10 mg/kg producing a slight elevation above saline, and 30 mg/kg producing a pronounced increase. Tested at 10 mg/kg and 30 mg/kg, 11a, 11b, 11c and 11d produced locomotor activities below those observed with 10 mg/kg of cocaine, whereas 11, even at 30 mg/kg, did not stimulate locomotion to levels above those seen with 10 mg/kg of cocaine. Thus, overall, each of the novel cocaine analogs, even at a dose of 30 mg/kg, did not stimulate locomotion to levels above those seen with 10 mg/kg of cocaine. This finding is particularly remarkable for compounds 11b and 11d, which exhibited greater potency than cocaine in blocking DAT (Table 1, supra), and especially 11d, which is ten-fold more potent than cocaine at blocking DAT.

While cocaine has a stimulatory effect, the above results demonstrate that modifying the C-1 in cocaine has the effect of reducing the centrally stimulatory action from an otherwise cocaine-like compound. This is of importance for the development of non-stimulatory analogs of cocaine, for therapeutic use. Analogs of cocaine prepared to date that have high affinity for DAT generally exhibit pronounced locomotor and central activity.

Example 8

Forced Swim Test

The Forced Swim Test (FST) is a rodent model often used to evaluate the anti-depressive effect of therapeutics. Rats swim under conditions in which escape is not possible. On the first day, rats are forced to swim for 15 minutes. The animals are observed to initially struggle to escape from the water. They then adopt a posture of immobility making only movements necessary to keep their heads above water. The rats are retested 24 hours later. The immobility increases. Treatment with standard antidepressant drugs within the 24 hours between the first exposure to forced swimming and retesting can block facilitated immobility, an effect which is associated with antidepressant efficacy in humans. See Porsolt et al, (1977) *Nature* 266:730-732; Detke et al. (1995) *Psychopharmacology* 121:66-72.

Antidepressant-like activity of compound 11 was tested in the forced swim test model as previously described (Porsolt et al., supra; Castagne et al. (2011) *Curr Protoc Neurosci* 55: Unit 8.10A). Briefly, adult male C57BL/6 mice (N=7-9/group) were placed into individual glass cylinders containing clean 25° C. (±1° C.) water, 15 cm deep for 15 minutes. Mice were removed, dried and returned to their home cages. A second 6-minute swim test was given 24 hours after the first. Saline (3 ml/kg, i.p.), Compound 11 (30 mg/kg, i.p.) or desipramine (10 mg/kg, i.p.; a well-known antidepressant, used as a positive control) were administered 24.5 hours, 5 hours, and 1 hour before the second swim test (i.e., 30 minutes, 19 hours and 23 hours after the first swim). Test sessions were video recorded. Behavior during the 6-minute swim test was scored from the videotapes. The cumulative amount of time that the mouse was immobile in the water during the last 4 minutes of the test was measured, as was the latency for the mouse to show the first bout of immobility behavior. Immobility was defined as the mouse performing no movements except those necessary to keep the head above the water (e.g., no swimming or climbing behaviors). The results are shown in FIG. 1. Compound 11 was as effective as the antidepressant desipramine in reducing immobility time (FIG. 1, left panel; F(2,22)=21.26; P=0.0001). Immobility scores were analyzed by a one-way ANOVA, followed by the Bonferroni post-hoc analysis. Latency to the first episode of immobility was significantly increased over saline, similar to desipramine (FIG. 1, right panel; F(2,22)=20.52; P<0.0001). Together, these results indicate that Compound 11 has antidepressant-like action.

Example 8

Brain Uptake

Figure 2:
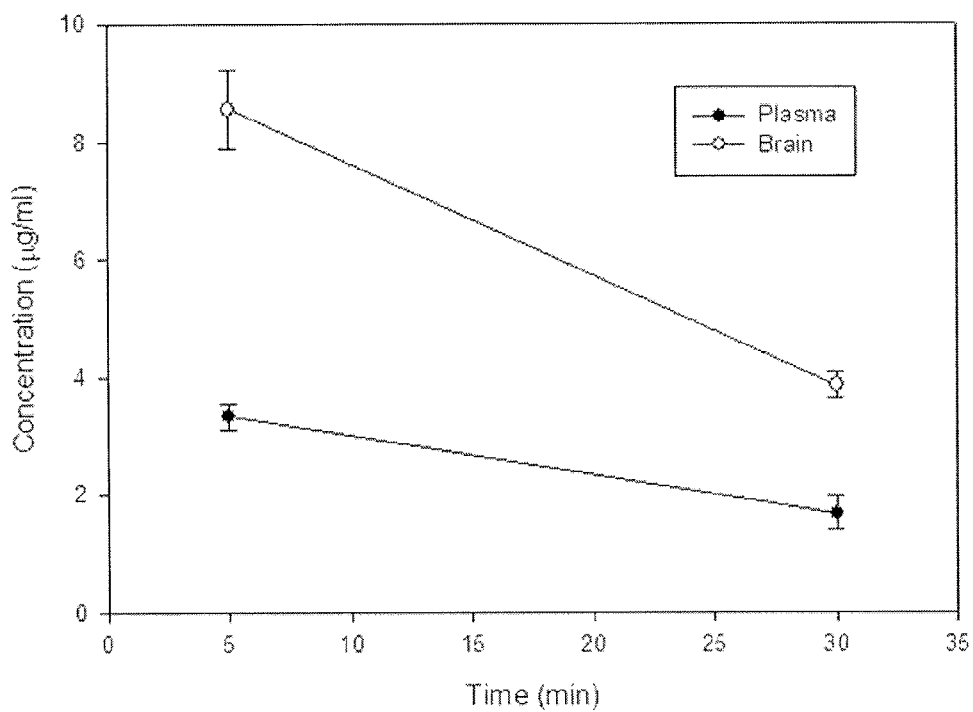
FIG. 2 shows pharmacokinetic data for Compound 11. Six male mice were injected i.p. with 30 mg/kg of Compound 11 and sacrificed at time points of 5 and 30 min (3 animals per time point). Brain and plasma levels of Compound 11 were determined by mass spectrometry. Data shown are mean±SEM (vertical bar).

Pharmacokinetic analysis for brain uptake of compound 11 was performed. Six male CD-1 mice (Charles River Laboratories, NC), age 8 weeks, were injected i.p. with 30 mg/kg of compound 11 and sacrificed at time points of 5 and 30 minutes (3 animals per time point). Brain and plasma levels of 11 were determined by mass spectrometry. The results are shown in FIG. 2. The plasma and brain levels of compound 11 were very close to reported levels after i.p. administration of 25 mg/kg cocaine (Reith et al., (1987) *J Pharmacol Exp Ther* 243:281-287; Benuck et al., (1987) *J Pharmacol Exp Ther* 243:144-149). For brain, the levels of compound 11 and cocaine were 8.6±0.7 and 6.7±1.2 μg/ml, respectively, at 5 minutes, and 3.8±0.2 and 2.3±0.3 μg/ml at 30 minutes; for plasma the respective values were 3.3±0.2 and 1.1±0.1, and 1.7±0.3 and 0.40±0.05 μg/ml (mean±SEM). Thus, similar pharmacokinetics were observed at a similar dose of compound 11 and cocaine, indicating rapid brain entry for the analog. Moreover, the correspondence in brain concentrations of cocaine and compound 11 at the 30-minute time point demonstrates that the two compounds have comparable brain elimination rate constants. This is of particular importance, as it negates the possibility that rapid elimination from the brain (e.g. due to active export from the CNS by efflux transporters at the blood-brain barrier) is responsible for the lack of cocaine-like locomotor stimulant effects exhibited by compound 11.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:
1. A compound of Formula (I):

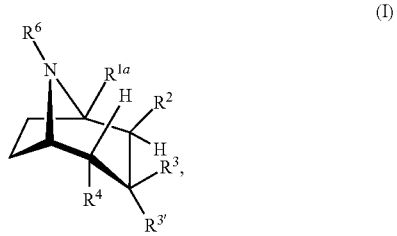

(I)

wherein:
R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, or substituted heterocyclyl;
R$^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;
R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;
R$^{3'}$ is H;
R$^4$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, (C$_{1-6}$) alkoxy, aroxy, or heteroaroxy;
R$^6$ is H, (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, substituted (C$_{2-6}$) alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;
R$^7$ and R$^8$ are independently H, (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl; and
each occurrence of R$^9$ is independently (C$_{1-6}$) alkyl, substituted (C$_{1-6}$) alkyl, (C$_{3-6}$) cycloalkyl, substituted (C$_{3-6}$) cycloalkyl, aryl, substituted aryl, heterocyclyl, or substituted heterocyclyl;
or a salt thereof.

2. The compound of claim 1, wherein R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, substituted (C$_{2-6}$) alkenyl, (C$_{2-6}$) alkynyl, or substituted (C$_{2-6}$) alkynyl.

3. The compound of claim 2, wherein R$^{1a}$ is (C$_{1-6}$) alkyl, substituted (C$_{1-6}$) alkyl, (C$_{3-6}$) cycloalkyl, substituted (C$_{3-6}$) cycloalkyl, (C$_{2-6}$) alkenyl, or substituted (C$_{2-6}$) alkenyl.

4. The compound of claim 3, wherein R$^{1a}$ is (C$_{1-6}$) alkyl, substituted (C$_{1-6}$) alkyl, (C$_{3-6}$) cycloalkyl, or substituted (C$_{3-6}$) cycloalkyl.

5. The compound of claim 4, wherein R$^{1a}$ is (C$_{1-6}$) alkyl or substituted (C$_{1-6}$)alkyl.

6. The compound of claim 5, wherein R$^{1a}$ is methyl.

7. The compound of claim 1, wherein R$^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, or —C(=S)N(OMe)Me.

8. The compound of claim 7, wherein R$^2$ is cyano, —C(=O)H, alkoxycarbonyl, aroxycarbonyl, heterocycloxycarbonyl, —C(=NR$^9$)R$^7$, —C(=O)NR$^7$R$^8$, —C(=S)NR$^7$R$^8$, —C(=O)N(OMe)Me, or —C(=S)N(OMe)Me.

9. The compound of claim 8, wherein R$^2$ is alkoxycarbonyl, aroxycarbonyl, heterocycloxycarbonyl, —C(=O)NR$^7$R$^8$, —C(=S)NR$^7$R$^8$, —C(=O)N(OMe)Me, or —C(=S)N(OMe)Me.

10. The compound of claim 1, wherein R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy.

11. The compound of claim 10, wherein R$^3$ is acyloxy, substituted acyloxy, aroyloxy, substituted aroyloxy, heteroaroyloxy, substituted heteroaroyloxy, —OC(=O)—NR$^7$R$^8$, (C$_{1-6}$) alkoxy, substituted (C$_{1-6}$) alkoxy, (C$_{3-6}$) cycloalkoxy, substituted (C$_{3-6}$) cycloalkoxy, (alkoxycarbonyl)oxy, (aroxycarbonyl)oxy, or (heterocycloxycarbonyl)oxy.

12. The compound of claim 11, wherein $R^3$ is acyloxy, substituted acyloxy, aroyloxy, substituted aroyloxy, heteroaroyloxy, substituted heteroaroyloxy, —OC(=O)—$NR^7R^8$, (alkoxycarbonyl)oxy, (aroxycarbonyl)oxy, or (heterocycloxycarbonyl)oxy.

13. The compound of claim 12, wherein $R^3$ is acyloxy, substituted acyloxy, aroyloxy, substituted aroyloxy, heteroaroyloxy, substituted heteroaroyloxy, or —OC(=O)—$NR^7R^8$.

14. The compound of claim 13, wherein $R^3$ is acyloxy, substituted acyloxy, aroyloxy, or substituted aroyloxy.

15. The compound of claim 1, wherein $R^4$ is H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, substituted heterocyclyl, $(C_{1-6})$ alkoxy, aroxy, or heteroaroxy.

16. The compound of claim 15, wherein $R^4$ is H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl.

17. The compound of claim 16, wherein $R^4$ is H, $(C_{1-6})$ alkyl, substituted $(C_{1-6})$ alkyl, $(C_{3-6})$ cycloalkyl, or substituted $(C_{3-6})$ cycloalkyl.

18. The compound of claim 1, wherein $R^6$ is H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, substituted heterocyclyl, —C(=O)$NR^7R^8$, —$SO_2R^9$, —$SO_2NR^7R^8$, —P(=O)$(OR^9)_2$, alkoxycarbonyl, aroxycarbonyl, heterocycloxycarbonyl, acyl, aroyl, or heterocycloyl.

19. The compound of claim 18, wherein $R^6$ is H, $(C_{1-6})$ alkyl, substituted $(C_{1-6})$ alkyl, $(C_{3-6})$ cycloalkyl, substituted $(C_{3-6})$ cycloalkyl, —C(=O)$NR^7R^8$, —$SO_2R^9$, —$SO_2NR^7R^8$, —P(=O)$(OR^9)_2$, alkoxycarbonyl, aroxycarbonyl, heterocycloxycarbonyl, acyl, aroyl, or heterocycloyl.

20. The compound of claim 19, wherein $R^6$ is H, $(C_{1-6})$ alkyl, substituted $(C_{1-6})$ alkyl, $(C_{3-6})$ cycloalkyl, substituted $(C_{3-6})$ cycloalkyl, —C(=O)$NR^7R^8$, —$SO_2R^9$, —$SO_2NR^7R^8$, alkoxycarbonyl, aroxycarbonyl, heterocycloxycarbonyl, acyl, aroyl, or heterocycloyl.

21. The compound of claim 1 which is methyl (1R,2R,3S,5S)-(−)-3-(benzoyloxy)-1,8-dimethyl-8-azabicyclo[3.2.1]octane-2-carboxylate, or a salt thereof.

22. The compound of claim 1 which is methyl (1R,2R,3S,5S)-(−)-1-propyl-3-(benzoyloxy)-8-methyl-8-azabicyclo[3.2.1]octane-2-carboxylate, methyl (1R, 2R, 3S, 5S)-(−)-1-ethyl-3-(benzoyloxy)-8-methyl-8-azabicyclo[3.2.1]octane-2-carboxylate, methyl (1R,2R,3S,5S)-(+)-1-pentyl-3-(benzoyloxy)-8-methyl-8-azabicyclo[3.2.1]octane-2-carboxylate, methyl (1R,2R,3S,5S)-(−)-3-(benzoyloxy)-1-phenyl-8-methyl-8-azabicyclo[3.2.1]octane-2-carboxylate, or a salt thereof.

23. A method of providing anesthesia to a subject in need thereof, wherein the method comprises administering to the subject a therapeutically effective amount of a pharmaceutical formulation comprising a compound of Formula (I):

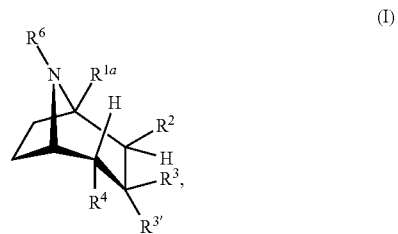

wherein:
$R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;

$R^2$ is cyano, —C(=O)H, alkoxycarbonyl, aroxycarbonyl, heterocycloxycarbonyl, acyl, aroyl, heterocycloyl, —C(=$NR^9$)$R^7$, —C(=O)$NR^7R^8$, —C(=S)$NR^7R^8$, —C(=O)N(OMe)Me, —C(=S)N(OMe)Me, —$SO_2R^9$, —$SO_2NR^7R^8$, or —P(=O)$(OR^9)_2$;

$R^3$ is acyloxy, substituted acyloxy, aroyloxy, substituted aroyloxy, heteroaroyloxy, substituted heteroaroyloxy, —OC(=O)—$NR^7R^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;

$R^{3'}$ is H;

$R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)$NR^7R^8$, —$SO_2R^9$, —$SO_2NR^7R^8$, —P(=O)$(OR^9)_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

24. The method of claim 23, wherein the pharmaceutical formulation is administered to the subject by parenteral, topical, oral or intranasal route.

25. The method of claim 23, wherein the compound of Formula (I) is methyl (1R,2R,3S,5S)-(−)-3-(benzoyloxy)-1,8-dimethyl-8-azabicyclo[3.2.1]octane-2-carboxylate, or a salt thereof.

26. (withdrawn; currently amended) The method of claim 23, wherein the compound of Formula (I) is methyl (1R,2R,3S,5S)-(−)-1-propyl-3-(benzoyloxy)-8-methyl-8-azabicyclo[3.2.1]octane-2-carboxylate, methyl (1R, 2R, 3S, 5S)-(−)-1-ethyl-3-(benzoyloxy)-8-methyl-8-azabicyclo[3.2.1]octane-2-carboxylate, methyl (1R,2R,3S,5S)-(+)-1-pentyl-3-(benzoyloxy)-8-methyl-8-azabicyclo[3.2.1]octane-2-carboxylate, methyl (1R,2R,3S,5S)-(−)-3-(benzoyloxy)-1-phenyl-8-methyl-8-azabicyclo[3.2.1]octane-2-carboxylate, or a salt thereof.

27. The method of claim 23, wherein the subject is human.

28. A method of blocking uptake of a monoamine neurotransmitter in a subject in need thereof, wherein the neurotransmitter is selected from the group consisting of serotonin, norepinephrine and dopamine, wherein the method comprises administering to the subject a therapeutically effective amount of a pharmaceutical formulation comprising a compound of Formula (I):

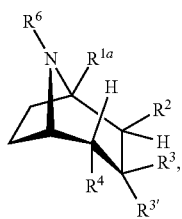

(I)

wherein:
- $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;
- $R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;
- $R^3$ is acyloxy, substituted acyloxy, aroyloxy, substituted aroyloxy, heteroaroyloxy, substituted heteroaroyloxy, —OC(=O)—NR$^7$R$^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;
- $R^{3'}$ is H;
- $R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;
- $R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;
- $R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and
- each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

29. The method of claim 28, wherein the neurotransmitter is serotonin.

30. The method of claim 28, wherein the neurotransmitter is norepinephrine.

31. The method of claim 28, wherein the neurotransmitter is dopamine.

32. The method of claim 28, wherein the pharmaceutical formulation is administered to the subject by parenteral, topical, oral or intranasal route.

33. The method of claim 28, wherein the compound of Formula (I) is methyl (1R,2R,3S,5S)-(−)-3-(benzoyloxy)-1,8-dimethyl-8-azabicyclo[3.2.I]octane-2-carboxylate, or a salt thereof.

34. The method of claim 28, wherein the compound of Formula (I) is methyl (1R,2R,3S,5S)-(−)-1-propyl-3-(benzoyloxy)-8-methyl-8-azabicyclo[3.2.1]octane-2-carboxylate, methyl (1R, 2R, 3S, 5S)-(−)-1-ethyl-3-(benzoyloxy)-8-methyl-8-azabicyclo[3.2.1]octane-2-carboxylate, methyl (1R,2R,3S,5S)-(+)-1-pentyl-3-(benzoyloxy)-8-methyl-8-azabicyclo[3.2.1]octane-2-carboxylate, methyl (1R,2R,3S,5S)-(−)-3-(benzoyloxy)-1-phenyl-8-methyl-8-azabicyclo[3.2.1]octane-2-carboxylate, or a salt thereof.

35. The method of claim 28, wherein the subject is human.

36. A method of treating depression in a subject in need thereof, wherein the method comprises administering to the subject a therapeutically effective amount of a pharmaceutical formulation comprising a compound of Formula (I):

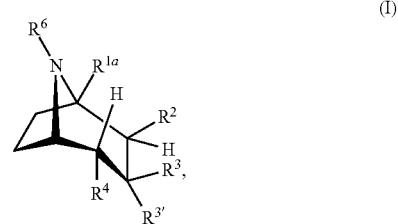

(I)

wherein:
- $R^{1a}$ is $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, or substituted heterocyclyl;
- $R^2$ is cyano, —C(=O)H, alkoxycarbonyl, aroxycarbonyl, heterocycloxycarbonyl, acyl, aroyl, heterocycloyl, —C(=NR$^9$)R$^7$, —C(=O)NR$^7$R$^8$, —C(=S)NR$^7$R$^8$, —C(=O)N(OMe)Me, —C(=S)N(OMe)Me, —SO$_2$R$^9$, —SO$_2$NR$^7$R$^8$, or —P(=O)(OR$^9$)$_2$;
- $R^3$ is acyloxy, substituted acyloxy, aroyloxy, substituted aroyloxy, heteroaroyloxy, substituted heteroaroyloxy, —OC(=O)—NR$^7$R$^8$, $(C_{1-6})$ alkoxy, substituted $(C_{1-6})$ alkoxy, $(C_{3-6})$ cycloalkoxy, substituted $(C_{3-6})$ cycloalkoxy, aroxy, substituted aroxy, heterocycloxy, substituted heterocycloxy, (alkoxycarbonyl)oxy, (aroxycarbonyl)oxy, or (heterocycloxycarbonyl)oxy;
- $R^{3'}$ is H;
- $R^4$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, $(C_{1-6})$ alkoxy, aroxy, or heteroaroxy;

$R^6$ is H, $(C_{1-6})$ alkyl, substituted $(C_{1-6})$ alkyl, $(C_{3-6})$ cycloalkyl, substituted $(C_{3-6})$ cycloalkyl, $(C_{2-6})$ alkenyl, substituted $(C_{2-6})$ alkenyl, $(C_{2-6})$ alkynyl, substituted $(C_{2-6})$ alkynyl, aryl, substituted aryl, heterocyclyl, substituted heterocyclyl, —C(=O)NR$^7$R$^8$, —SO$_2$R$^9$, —SO$_2$NR$^7$R$^8$, —P(=O)(OR$^9$)$_2$, alkoxycarbonyl, aroxycarbonyl, heterocycloxycarbonyl, acyl, aroyl, or heterocycloyl;

$R^7$ and $R^8$ are independently H, $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl; and each occurrence of $R^9$ is independently $(C_{1-6})$ alkyl, substituted $(C_{1-6})$ alkyl, $(C_{3-6})$ cycloalkyl, substituted $(C_{3-6})$ cycloalkyl, aryl, substituted aryl, heterocyclyl, or substituted heterocyclyl;

or a salt thereof.

37. The method of claim 36, wherein the pharmaceutical formulation is administered to the subject by parenteral, topical, oral or intranasal route.

38. The method of claim 36, wherein the compound of Formula (I) is methyl (1R,2R,3S,5S)-(−)-3-(benzoyloxy)-1,8-dimethyl-8-azabicyclo[3.2.1]octane-2-carboxylate, or a salt thereof.

39. The method of claim 36, wherein the compound of Formula (I) is
methyl (1R,2R,3S,5S)-(−)-1-propyl-3-(benzoyloxy)-8-methyl-8-azabicyclo[3.2.1]octane-2-carboxylate,
methyl (1R, 2R, 3S, 5S)-(−)-1-ethyl-3-(benzoyloxy)-8-methyl-8-azabicyclo[3.2.1]octane-2-carboxylate,
methyl (1R,2R,3S,5S)-(+)-1-pentyl-3-(benzoyloxy)-8-methyl-8-azabicyclo[3.2.1]octane-2-carboxylate,
methyl (1R,2R,3S,5S)-(−)-3-(benzoyloxy)-1-phenyl-8-methyl-8-azabicyclo[3.2.1]octane-2-carboxylate, or
a salt thereof.

40. The method of claim 36, wherein the subject is human.

41. The compound of claim 1, wherein:
$R^{1a}$ is $(C_{1-6})$ alkyl, substituted $(C_{1-6})$ alkyl, $(C_{3-6})$ cycloalkyl, substituted $(C_{3-6})$ cycloalkyl, aryl or substituted aryl;
$R_2$ is C(=O)H, alkoxycarbonyl or aroxycarbonyl;
$R_3$ is aroyloxy or substituted aroyloxy;
$R^4$ is H, $(C_{1-6})$ alkyl, substituted $(C_{1-6})$ alkyl, $(C_{3-6})$ cycloalkyl, or substituted $(C_{3-6})$ cycloalkyl; and
$R^6$ is H, $(C_{1-6})$ alkyl, substituted $(C_{1-6})$ alkyl, $(C_{3-6})$ cycloalkyl, substituted $(C_{3-6})$ cycloalkyl, aryl or substituted aryl; or
a salt thereof.

42. The compound of claim 41, wherein:
$R^{1a}$ is $(C_{1-6})$ alkyl, substituted $(C_{1-6})$ alkyl or phenyl;
$R_2$ is alkoxycarbonyl;
$R_3$ is aroyloxy,
$R^4$ is H, $(C_{1-6})$ alkyl or substituted $(C_{1-6})$ alkyl; and
$R^6$ is H, $(C_{1-6})$ alkyl or substituted $(C_{1-6})$ alkyl; or
a salt thereof.

43. The method of claim 23, wherein in the compound of Formula (I):
$R^{1a}$ is $(C_{1-6})$ alkyl, substituted $(C_{1-6})$ alkyl, $(C_{3-6})$ cycloalkyl, substituted $(C_{3-6})$ cycloalkyl, aryl or substituted aryl;
$R_2$ is C(=O)H, alkoxycarbonyl or aroxycarbonyl;
$R_3$ is aroyloxy or substituted aroyloxy,
$R^4$ is H, $(C_{1-6})$ alkyl, substituted $(C_{1-6})$ alkyl, $(C_{3-6})$ cycloalkyl, or substituted $(C_{3-6})$ cycloalkyl; and
$R^6$ is H, $(C_{1-6})$ alkyl, substituted $(C_{1-6})$ alkyl, $(C_{3-6})$ cycloalkyl, substituted $(C_{3-6})$ cycloalkyl, aryl or substituted aryl; or
a salt thereof.

44. The method of claim 43, wherein in the compound of Formula (I):
$R^{1a}$ is $(C_{1-6})$ alkyl, substituted $(C_{1-6})$ alkyl or phenyl;
$R_2$ is alkoxycarbonyl;
$R_3$ is aroyloxy,
$R^4$ is H, $(C_{1-6})$ alkyl or substituted $(C_{1-6})$ alkyl; and
$R^6$ is H, $(C_{1-6})$ alkyl or substituted $(C_{1-6})$ alkyl; or
a salt thereof.

45. The method of claim 28, wherein in the compound of Formula (I):
$R^{1a}$ is $(C_{1-6})$ alkyl, substituted $(C_{1-6})$ alkyl, $(C_{3-6})$ cycloalkyl, substituted $(C_{3-6})$ cycloalkyl, aryl or substituted aryl;
$R_2$ is C(=O)H, alkoxycarbonyl or aroxycarbonyl;
$R_3$ is aroyloxy or substituted aroyloxy,
$R^4$ is H, $(C_{1-6})$ alkyl, substituted $(C_{1-6})$ alkyl, $(C_{3-6})$ cycloalkyl, or substituted $(C_{3-6})$ cycloalkyl; and
$R^6$ is H, $(C_{1-6})$ alkyl, substituted $(C_{1-6})$ alkyl, $(C_{3-6})$ cycloalkyl, substituted $(C_{3-6})$ cycloalkyl, aryl or substituted aryl; or
a salt thereof.

46. The method of claim 45, wherein in the compound of Formula (I):
$R^{1a}$ is $(C_{1-6})$ alkyl, substituted $(C_{1-6})$ alkyl or phenyl
$R_2$ is alkoxycarbonyl;
$R_3$ is aroyloxy,
$R^4$ is H, $(C_{1-6})$ alkyl or substituted $(C_{1-6})$ alkyl; and
$R^6$ is H, $(C_{1-6})$ alkyl or substituted $(C_{1-6})$ alkyl; or
a salt thereof.

47. The method of claim 36, wherein in the compound of Formula (I):
$R^{1a}$ is $(C_{1-6})$ alkyl, substituted $(C_{1-6})$ alkyl, $(C_{3-6})$ cycloalkyl, substituted $(C_{3-6})$ cycloalkyl, aryl or substituted aryl;
$R_2$ is C(=O)H, alkoxycarbonyl or aroxycarbonyl;
$R_3$ is aroyloxy or substituted aroyloxy,
$R^4$ is H, $(C_{1-6})$ alkyl, substituted $(C_{1-6})$ alkyl, $(C_{3-6})$ cycloalkyl, or substituted $(C_{3-6})$ cycloalkyl; and
$R^6$ is H, $(C_{1-6})$ alkyl, substituted $(C_{1-6})$ alkyl, $(C_{3-6})$ cycloalkyl, substituted $(C_{3-6})$ cycloalkyl, aryl or substituted aryl; or
a salt thereof.

48. The method of claim 47, wherein in the compound of Formula (I):
$R^{1a}$ is $(C_{1-6})$ alkyl, substituted $(C_{1-6})$ alkyl or phenyl;
$R_2$ is alkoxycarbonyl;
$R_3$ is aroyloxy,
$R^4$ is H, $(C_{1-6})$ alkyl or substituted $(C_{1-6})$ alkyl; and
$R^6$ is H, $(C_{1-6})$ alkyl or substituted $(C_{1-6})$ alkyl; or
a salt thereof.

* * * * *